(12) United States Patent
Ross

(10) Patent No.: US 11,083,881 B2
(45) Date of Patent: *Aug. 10, 2021

(54) METHOD FOR INCREASING PERMEABILITY OF A CELLULAR LAYER OF EPITHELIAL CELLS

(71) Applicant: Sorrento Therapeutics, Inc., San Diego, CA (US)

(72) Inventor: Russell Frederick Ross, Jacksonville Beach, FL (US)

(73) Assignee: SORRENTO THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/422,195

(22) Filed: May 24, 2019

(65) Prior Publication Data

US 2019/0275310 A1    Sep. 12, 2019

Related U.S. Application Data

(63) Continuation of application No. 15/413,475, filed on Jan. 24, 2017, now Pat. No. 10,342,965, which is a continuation of application No. 13/641,500, filed as application No. PCT/IB2011/051863 on Apr. 27, 2011, now Pat. No. 9,586,044.

(60) Provisional application No. 61/435,963, filed on Jan. 25, 2011, provisional application No. 61/411,085, filed on Nov. 8, 2010, provisional application No. 61/328,723, filed on Apr. 28, 2010.

(51) Int. Cl.
| | |
|---|---|
| *A61M 37/00* | (2006.01) |
| *A61N 1/30* | (2006.01) |
| *A61K 9/00* | (2006.01) |
| *A61K 38/17* | (2006.01) |

(52) U.S. Cl.
CPC ....... *A61M 37/0015* (2013.01); *A61K 9/0021* (2013.01); *A61K 38/1793* (2013.01); *A61N 1/306* (2013.01); *A61M 2037/003* (2013.01); *A61M 2037/0007* (2013.01); *A61M 2037/0023* (2013.01); *A61M 2037/0053* (2013.01); *A61M 2037/0061* (2013.01); *A61M 2205/0244* (2013.01)

(58) Field of Classification Search
None
See application file for complete search history.

(56) References Cited

U.S. PATENT DOCUMENTS

| | | |
|---|---|---|
| 3,797,494 A | 3/1974 | Zaffaroni |
| 3,964,482 A | 6/1976 | Gerstel |
| 4,031,894 A | 6/1977 | Urquhart |
| 4,051,840 A | 10/1977 | Kantrowitz |
| 4,201,211 A | 5/1980 | Chandrasekaran |
| 4,379,454 A | 4/1983 | Campbell |
| 4,436,741 A | 3/1984 | Urquhart |
| 4,588,580 A | 5/1986 | Gale |
| 4,615,699 A | 10/1986 | Gale |
| 4,661,105 A | 4/1987 | Gale |
| 4,681,584 A | 7/1987 | Gale |
| 4,698,062 A | 10/1987 | Gale |
| 4,725,272 A | 2/1988 | Gale |
| 4,832,953 A | 5/1989 | Campbell |
| 4,880,633 A | 11/1989 | Loper |
| 4,908,027 A | 3/1990 | Enscore |
| 5,004,610 A | 4/1991 | Osborne |
| 5,310,559 A | 5/1994 | Shah |
| 5,328,470 A | 7/1994 | Nabel |
| 5,342,623 A | 8/1994 | Enscore |
| 5,344,656 A | 9/1994 | Enscore |
| 5,364,630 A | 11/1994 | Osborne |
| 6,132,755 A | 10/2000 | Eicher |
| 6,312,612 B1 | 11/2001 | Sherman |
| 6,334,856 B1 * | 1/2002 | Allen ............. A61B 5/14514 604/191 |
| 6,375,978 B1 | 4/2002 | Kleiner |
| 6,451,240 B1 | 9/2002 | Sherman |
| 6,471,993 B1 | 10/2002 | Shastri |
| 6,561,143 B2 | 5/2003 | Holtzman |
| 6,569,143 B2 | 5/2003 | Alchas |
| 6,591,124 B2 | 7/2003 | Sherman |
| 6,611,707 B1 | 8/2003 | Prausnitz |
| 6,656,147 B1 | 12/2003 | Gertsek |
| 6,663,820 B2 | 12/2003 | Arias |

(Continued)

FOREIGN PATENT DOCUMENTS

| | | |
|---|---|---|
| EP | 2100850 A1 | 9/2009 |
| WO | 1999045860 A1 | 9/1990 |

(Continued)

OTHER PUBLICATIONS

Al-Qallafetal. "Optimizing Microneedle Arrays to Increase Skin Permeability for Transdermal Drug Delivery" 2009.*
Al-Qallaf et al. "Optimizing Microneedle Arrays to Incrrease Skin Permeability for Transdermal Drug Delivery". (2009).
Ahmed et al; "Bis(diacetylene)s I: Langmuir-Blodgett films", Thin Solid Films 187: 141-153; 1990.
Ainslie et al., "Microfabricated implants for applications in therapeutic delivery, tissue engineering, and biosensing." Royal Society of Chemistry. 8. (2008): 1864-1878.

(Continued)

*Primary Examiner* — Danah Al-Awadi
(74) *Attorney, Agent, or Firm* — Armstrong Teasdale LLP

(57) ABSTRACT

A method for increasing permeability of a cellular layer of epithelial cells includes contacting the cellular layer with a nanostructured surface including a plurality of first nanostructures arranged thereon and projecting outward therefrom. A fractal dimension of the plurality of nanostructures is greater than 1. The permeability of the cellular layer by a compound is increased as compared to the permeability of the cellular layer prior to contact with the surface.

14 Claims, 29 Drawing Sheets

(56) References Cited

U.S. PATENT DOCUMENTS

| | | |
|---|---|---|
| 6,767,341 B2 | 7/2004 | Cho |
| 6,881,203 B2 | 4/2005 | Delmore |
| 6,908,453 B2 | 6/2005 | Fleming |
| 6,926,953 B2 | 8/2005 | Nealey |
| 6,979,347 B1 | 12/2005 | Wu |
| 6,980,855 B2 | 12/2005 | Cho |
| 6,995,336 B2 | 2/2006 | Hunt |
| 7,048,723 B1 | 5/2006 | Frazier |
| 7,108,681 B2 | 9/2006 | Gartstein |
| 7,115,108 B2 | 10/2006 | Wilkinson |
| 7,129,554 B2 | 10/2006 | Lieber |
| 7,131,987 B2 | 11/2006 | Sherman |
| 7,185,663 B2 | 3/2007 | Koch |
| 7,189,435 B2 | 3/2007 | Tuominen |
| 7,226,439 B2 | 6/2007 | Prausnitz |
| 7,250,037 B2 | 7/2007 | Shermer |
| 7,285,113 B2 | 10/2007 | Yeshurun |
| 7,315,758 B2 | 1/2008 | Kwiatkowski |
| 7,332,339 B2 | 2/2008 | Canham |
| 7,374,864 B2 | 5/2008 | Guo |
| 7,416,541 B2 | 8/2008 | Yuzhakov |
| 7,429,258 B2 | 9/2008 | Angel |
| 7,449,200 B2 | 11/2008 | Sung |
| 7,473,244 B2 | 1/2009 | Frazier |
| 7,531,120 B2 | 5/2009 | Van Rijn |
| 7,537,590 B2 | 5/2009 | Santini, Jr. |
| 7,544,770 B2 | 6/2009 | Haynie |
| 7,556,615 B2 | 7/2009 | Pettis |
| 7,563,451 B2 | 7/2009 | Lin |
| 7,572,405 B2 | 8/2009 | Sherman |
| 7,578,954 B2 | 8/2009 | Gartstein |
| 7,582,069 B2 | 9/2009 | Laurent |
| 7,588,552 B2 | 9/2009 | Yeshurun |
| 7,611,481 B2 | 11/2009 | Cleary |
| 7,627,938 B2 | 12/2009 | Kim |
| 7,658,728 B2 | 2/2010 | Yuzhakov |
| 7,753,888 B2 | 7/2010 | Mukerjee |
| 7,785,301 B2 | 8/2010 | Yuzhakov |
| 7,803,574 B2 | 9/2010 | Desai |
| 7,828,827 B2 | 11/2010 | Gartstein |
| 7,846,488 B2 | 12/2010 | Johnson |
| 7,901,387 B2 | 3/2011 | Stemme |
| 7,914,480 B2 | 3/2011 | Cleary |
| 7,914,813 B2 | 3/2011 | Adachi |
| 7,918,814 B2 | 4/2011 | Prausnitz |
| 7,972,616 B2 | 7/2011 | Dubrow |
| 7,981,346 B2 | 7/2011 | Griss |
| 7,997,274 B2 | 8/2011 | Baska |
| 8,052,633 B2 | 11/2011 | Kendall |
| 8,057,842 B2 | 11/2011 | Choi |
| 8,088,321 B2 | 1/2012 | Ferguson |
| 8,097,456 B2 | 1/2012 | Borenstein |
| 8,118,753 B2 | 2/2012 | Cho |
| 8,137,697 B1 | 3/2012 | Sung |
| 8,137,736 B2 | 3/2012 | Zhu |
| 8,162,901 B2 | 4/2012 | Gonnelli |
| 8,238,995 B2 | 8/2012 | Chandrasekaran |
| 8,366,677 B2 | 2/2013 | Kaspar |
| 8,389,205 B2 | 3/2013 | Duerig |
| 8,419,708 B2 | 4/2013 | Tokumoto |
| 8,506,530 B2 | 8/2013 | Laermer |
| 8,574,615 B2 | 11/2013 | Tenney |
| 8,690,838 B2 | 4/2014 | Ozawa |
| 8,696,637 B2 | 4/2014 | Ross |
| 8,747,886 B2 | 6/2014 | Amsden |
| 8,915,957 B2 | 12/2014 | Arney |
| 8,944,804 B2 | 2/2015 | Robeson |
| 9,028,409 B2 | 5/2015 | Yodfat |
| 2002/0082543 A1 | 6/2002 | Park |
| 2002/0133129 A1 | 9/2002 | Arias |
| 2002/0183688 A1 | 12/2002 | Lastovich |
| 2004/0028875 A1 | 2/2004 | Van Rijn |
| 2004/0063100 A1 | 4/2004 | Wang |
| 2004/0087992 A1 | 5/2004 | Gartstein |
| 2004/0106904 A1 | 6/2004 | Gonnelli |
| 2004/0176732 A1 | 9/2004 | Frazier |
| 2005/0049625 A1 | 3/2005 | Shaya |
| 2005/0112135 A1 | 5/2005 | Cormier |
| 2005/0112636 A1 | 5/2005 | Hurt |
| 2005/0118388 A1 | 6/2005 | Kingsford |
| 2005/0119723 A1 | 6/2005 | Peacock |
| 2005/0124967 A1 | 6/2005 | Kaestner |
| 2005/0137531 A1* | 6/2005 | Prausnitz ........... A61B 5/14514 604/173 |
| 2005/0143713 A1 | 6/2005 | Delmore |
| 2005/0178760 A1 | 8/2005 | Chang |
| 2005/0187521 A1 | 8/2005 | Fleming |
| 2005/0203613 A1 | 9/2005 | Arney |
| 2006/0024358 A1 | 2/2006 | Santini |
| 2006/0025848 A1 | 2/2006 | Weber |
| 2006/0051404 A1 | 3/2006 | Yeshurun |
| 2006/0264893 A1 | 11/2006 | Sage, Jr. |
| 2007/0066934 A1 | 3/2007 | Etheredge |
| 2007/0078376 A1 | 4/2007 | Smith |
| 2007/0081977 A1 | 4/2007 | Horstmann |
| 2007/0088248 A1 | 4/2007 | Glenn |
| 2007/0110810 A1 | 5/2007 | Smith |
| 2007/0112309 A1 | 5/2007 | Zucker |
| 2007/0112548 A1 | 5/2007 | Dickerson |
| 2007/0191761 A1 | 8/2007 | Boone |
| 2007/0249552 A1 | 10/2007 | Khalili |
| 2007/0250018 A1 | 10/2007 | Adachi |
| 2007/0276318 A1 | 11/2007 | Henley |
| 2007/0282247 A1* | 12/2007 | Desai ................. A61L 27/54 604/19 |
| 2008/0088066 A1 | 4/2008 | Ferguson |
| 2008/0091226 A1 | 4/2008 | Yeshurun |
| 2008/0097352 A1 | 4/2008 | Beck |
| 2008/0108958 A1 | 5/2008 | Carter |
| 2008/0195035 A1 | 8/2008 | Frederickson |
| 2008/0200883 A1 | 8/2008 | Tomono |
| 2008/0208076 A1 | 8/2008 | Cho |
| 2008/0217180 A1 | 9/2008 | Doye |
| 2008/0221408 A1 | 9/2008 | Hoarau |
| 2008/0262416 A1 | 10/2008 | Duan |
| 2008/0269666 A1 | 10/2008 | Wang |
| 2008/0269685 A1 | 10/2008 | Singh |
| 2008/0305989 A1 | 12/2008 | Wen |
| 2008/0311172 A1 | 12/2008 | Schapira |
| 2008/0312610 A1 | 12/2008 | Binks |
| 2009/0012494 A1 | 1/2009 | Yeshurun |
| 2009/0043279 A1 | 2/2009 | Kaspar |
| 2009/0069788 A1 | 3/2009 | Yeshurun |
| 2009/0093776 A1 | 4/2009 | Yue |
| 2009/0093871 A1 | 4/2009 | Rea |
| 2009/0093879 A1 | 4/2009 | Wawro |
| 2009/0099427 A1 | 4/2009 | Jina |
| 2009/0099502 A1 | 4/2009 | Tokumoto |
| 2009/0099537 A1 | 4/2009 | DeVoe |
| 2009/0118662 A1 | 5/2009 | Schnall |
| 2009/0137926 A1 | 5/2009 | Srinivasan |
| 2009/0177273 A1 | 7/2009 | Piveteau |
| 2009/0187167 A1 | 7/2009 | Sexton |
| 2009/0198189 A1 | 8/2009 | Simons |
| 2009/0232870 A1 | 9/2009 | Srivastava |
| 2010/0004733 A1 | 1/2010 | Atanasoska |
| 2010/0021464 A1 | 1/2010 | Archambeau |
| 2010/0076035 A1 | 3/2010 | Carter |
| 2010/0121307 A1 | 5/2010 | Lockard |
| 2010/0168506 A1 | 7/2010 | Moon |
| 2010/0215580 A1 | 8/2010 | Hanes |
| 2010/0226943 A1* | 9/2010 | Brennan .................. A61L 2/02 424/400 |
| 2010/0256568 A1 | 10/2010 | Frederickson |
| 2010/0274203 A1 | 10/2010 | Lee |
| 2011/0021996 A1 | 1/2011 | Lee |
| 2011/0046557 A1 | 2/2011 | Lee |
| 2011/0059150 A1 | 3/2011 | Kendall |
| 2011/0144591 A1 | 6/2011 | Ross |
| 2011/0160069 A1 | 6/2011 | Corrie |
| 2011/0270221 A1 | 11/2011 | Ross |
| 2011/0276003 A1 | 11/2011 | Luttge |
| 2012/0089117 A1* | 4/2012 | Junginger ........... A61B 17/205 604/506 |

(56) References Cited

U.S. PATENT DOCUMENTS

| | | | |
|---|---|---|---|
| 2012/0109065 | A1 | 5/2012 | Backes |
| 2012/0114734 | A1 | 5/2012 | Desai |
| 2012/0128932 | A1 | 5/2012 | Veith |
| 2013/0144217 | A1 | 6/2013 | Ross |
| 2013/0144257 | A1 | 6/2013 | Ross |
| 2013/0158505 | A1 | 6/2013 | Ross |
| 2013/0165861 | A1 | 6/2013 | Ross |
| 2013/0211310 | A1 | 8/2013 | Bommarito |
| 2013/0331792 | A1 | 12/2013 | Karp |
| 2014/0112921 | A1 | 4/2014 | Ross |
| 2014/0287019 | A1 | 9/2014 | Ollerenshaw |
| 2014/0343532 | A1 | 11/2014 | Ross |

FOREIGN PATENT DOCUMENTS

| | | | |
|---|---|---|---|
| WO | 2001075164 | A2 | 10/2001 |
| WO | 2002030506 | A2 | 4/2002 |
| WO | 2002032480 | A2 | 4/2002 |
| WO | 2003020359 | A2 | 3/2003 |
| WO | 2003024508 | A2 | 3/2003 |
| WO | 2003092785 | A1 | 11/2003 |
| WO | 2005049128 | A1 | 6/2005 |
| WO | 2006062974 | A2 | 6/2006 |
| WO | 2007012114 | A1 | 2/2007 |
| WO | 2007070004 | A2 | 6/2007 |
| WO | 2007081876 | A2 | 7/2007 |
| WO | WO 2007081876 | * | 7/2007 |
| WO | 2007112309 | A2 | 10/2007 |
| WO | 2008003564 | A1 | 1/2008 |
| WO | 2008024141 | A2 | 2/2008 |
| WO | 2009079589 | A2 | 6/2009 |
| WO | 2009113856 | A1 | 9/2009 |
| WO | 2010070628 | A1 | 6/2010 |
| WO | 2010087971 | A2 | 8/2010 |
| WO | 2010126640 | A2 | 11/2010 |
| WO | 2011116388 | A1 | 9/2011 |
| WO | 2011135531 | A1 | 11/2011 |
| WO | 2012006677 | A1 | 1/2012 |
| WO | 2012046149 | A1 | 4/2012 |

OTHER PUBLICATIONS

Ainslie et al., "Microfabricated Devices for Enhanced Bioadhesive Drug Delivery: Attachment to and Small-Molecule Release Through a Cell Monolayer Under Flow." Small. (2009).

Berkarde, lil Gercek. "Biomimetic Apatite-coated PCL Scaffolds: Effect of Surface Nanotopography on Cellular Functions." Journal of Bioactive and Compatible Polymers . 24.6 (2009): 507-524.

Berry et al., "The interaction of human bone marrow cells with nanotopographical features in three dimensional constructs." Journal of Biomedical Materials Research Part A. 79A.2 (2006): 431-439.

Biehl et al., "Proliferation of Mouse Embryonic Stem Cell Progeny and the Spontaneous Contractile Activity of Cardiomyocytes Are Affected by Microtopography." Developmental Dynamics . 238. (2009): 1964-1973.

Brunauer et al., "Adsorption of Gases in Multimolecular Layers." Journal of the American Chemical Society. 60. (1938): 309-319.

Chandler, David L., "PhysOrg.com." Harnessing nanopatterns: Tiny textures can produce big differences. N.p., Sep. 24, 2009. Web. Dec. 1, 2009, <http://www.physorg.com/news173004362.html>.

Choi et al. "Cell interaction with three-dimensional sharp-tip nanotopography." Biomaterials. 28.9 (2007): 1672-1679.

Chun et al., "The role of polymer nanosurcace roughness and the submicron pores in improving bladder urothelial cell density and inhibiting calcium oxalate stone formation." Nanotechnology. 20.8 (2009): 85104.

Citi, S., "Protein Kinase Inhibitors Prevent Junction Dissociation Induced by Low Extracellular Calcium in MDCK Epithelial Cells", J Cell Biology, 1992, 117(1) 169-178.

Cohn, Abby. "Drug Delivery, Nanoscale." Innovations. 3.4 (2009).

Curtis et al., "Cell signaling arising from nanotopography: implicatinos for nanomedicaldevices." Nanomedicine. 1.1 (2006): 67-72.

Dalby, Matthew J. "Nanostructured surfaces: cell engineering and cell biology." Nanomedicine. 4.2 (2009): 247-248.

Dalby et al., "Attempted endocytosis of nano-environment produced by colloidal lithography by human fibroblasts." Experimental Cell Research. 295. (2004): 387-394.

Dalby et al., "Nano-Topography Induces Mechanotransduction in Human Fibroblasts." European Cells and Materials . 6.2 (2003): 31.

Dalby et al., "Increasing Fibroblast Response to Materials Using Nanotopography: Morphological and Genetic measurements of Cell Response to 13-nm-High Polymer Demixed Islands." Experimental Cell Research. 276.1 (2002): 1-9.

Fischer et al., "Biomimetic Nanowire Coatings for Next Generation Adhesive Drug Delivery Systems." Nano Letters. 9.2 (2009): 716-720.

Geiger & Ayalon, "Cadherins", Annu Rev Cell Biol, 1992, 8:307-32.

Gumbiner & Simons, "A Functional Assay for Proteins Involved in Establishing an Epithelial Occluding Barrier: Identification of an Uvomorulin-like Polypeptide", J. Cell Biology, 1986, 102: 457-468.

Hart et al., "Filapodial Sensing of Nanotopography in Osteoprogenitor Cells." European Cells and Materials . 10.2 (2005): 65.

He, et al., "The anatase phase of nanotopography titania plays an important role on osteoblast cell morphology and proliferation", Journal of Mater. Sci: Mater Med (2008), 19:3465-3472.

Hirano et al., "Calcium-dependent Cell-Cell Adhesion Molecules (Cadherins): Subclass Specificities and Possible Involvement of Actin Bundles", J. Cell Biology, 1987, 105(6): 2501-2510.

Hu et al., "Surface Energy Induced Patterning of Polymer Nanostructures for Cancer Diagnosis and Therapy." IEEE Nano 2007 Conference Paper. (2007).

Kaushal et al, Influence of Piperline on Transcutaneous Permeation of Repaglinide in Rats and on Tight Junction Proteins in HaCaT Cells: Unveiling the Mechanisms for Enhanced Permeation; Sci. Pharm. 2009; 77; 877-897.

Kitner, C., "Regulation of embryonic cell adhesion by the cadherin cytoplasmic domain", Cell, 1992, 69(2):225-36.

Korhonen et al., "Nitric oxide production and signaling in inflammation", Curr Drug Targets Inflamm Allergy 4(4): 471-9, 2005.

Langeler et al., "Norepinephrine and iloprost improve barrier function of human endothelial cellmonolayers: role of cAMP", Am J Physio Cell Physiol, 1991, vol. 260(5), C1052-C1059.

Lim et al., "Huma foetal ostoblastic cell response to polymer-demixed nanotopographic interfaces." Journal of the Royal Society Interface. 2.2 (2005): 97-108.

Madara, JL, "Regulation of the movement of solutes across tight junctions", Annu Rev Physiol, 1998, 60:143-59.

Mandavi et al., "A biodegradable and biocompatible gecko-inspired tissue adhesive." PNAS. 105.7 (2008): 2307-2312.

Martinez-Palomo et al., "Experimental Modulation of Occluding Junctions in a Cultured Transporting Epithelium", J. Cell Biology, 1980, 87: 736-745.

Meirelles et al., "The effect of chemical and nanotopographical modifications on the early stages of osseointegration." International Journal of Oral and Maxillofacial Implants. 23.4 (2008): 641-647.

Mendelsohn et al., "Inorganic Nanoporous Membranes for Immunoisolated Cell-Based Drug Delivery." Therapeutic Applications of Cell Microencapsulation.

Nagafuchi & Takechi, "Cell binding function of E-cadherin is regulated by the cytoplasmic domain", EMBO Journal, 1988, 7(12): 3679-3684.

Ng et al., "Study of substrate topographical effects on epithelial cell behavior using etched alpha—particle tracks on PADC films." Nuclear Instruments and Methods in Physics Research Section B: Beam Interactions with Materials and Atoms. 266.14 (2008): 3247-3256.

Ojakian, GK, "Tumor promotor-induced changes in the permeability of epithelial cell tight junctions", Cell, 1981, 23(1): 95-103.

Orr et al., "Submicrometer and Nanoscale Inorganic Particles Exploit the Actin Machinery to Be Propelled along Microvilli-likestructures into Alveolar Cells." American Chemical Society Nano. 1.5 (2007): 463-475.

(56) References Cited

OTHER PUBLICATIONS

Ozawa et al., "The cytoplasmic domain of the cell adhesion molecule uvomorulin associates with three independnet proteins structurally related in different species", EMBO Journal, 1989, 8(6): 1711-1717.

Ozawa et al., "Uvomorulin-catenin complex formation is regulated by specific domain in the cytoplasmic region of the cell adhesion molecule", Dev Biology, 1990, 87: 4246-4250.

Peng et al., "Long-Term Small Molecule and Protein Elution from TiO2 Nanotubes." Nano Letters. 9.5 (2009): 1932-1936.

Peng et al., "The effect of TiO2 nanotubes on endothelial function and smooth muscle proliferation." Journal of Biomaterials. 30. (2009): 1268-1272.

Rubin et al., "A Cell Culture Model of the Blood-Brain Barrier", J. Cell Biology, 1991, 115:1725-1735.

Rubin, LL, "Endothelial cells: adhesion and tight junctions", Curr Opin Cell Biol, 1992, 4(5):830-3.

Rutten et al., "Electrical resistance and macromolecular permeability of brain endothelial monolayer cultures", Brain Res, 1987, 425(2):301-10.

Sapra et al., "Transdermal Delivery of Carvedilol Containing Glycyrrhizin and Chitosan as Permeation Enhancers: Biochemical, Biophysical, Microscopic and Pharmacodynamic Evaluation." Drug Delivery. 15.7 (2008): 443-454.

Sapra et al., "Transdermal delivery of carvedilol in rats: proving the percutaneous permeation enhancement mechanism of soybean extract-chitosan mixture." Drug Delivery. 35.10 (2009): 1230-1241.

Sapra et al., "Effect of Asparagus racemous Extract on Transdermal Delivery of Carvedilol: A Mechanistic Study" American Association of Pharmaceutical Scientists PharmSciTech. 10.1 (2009): 199.

Schubert et al, "Sliding-induced adhesion of stiff polymer microfibre arrays. II. Microscale behavior", J Royal Society; Jan. 2008, 5, 845-853.

Stappert et al., "A short core region of E-cadherin is essential for certain binding and is highly phosphorylated", 1993, Cell Adhes Commun, 2(4):319-27.

Stelzner et al., "Role of cyclic adenosine monophosphate in the induction of endothelial barrier properties", J. Cell Physiol, 1989, 139(1):157-66.

Teo et al. "The effect of micro and nanotopography on endocytosis in drug and gene delivery systems", Biomaterials, 32 (2011), 9866-9875.

Thakar et al., "Contractility-Dependent Modulation of Cell Proliferation and Adhesion by Microscale Topographical Cues." Small. 4.9 (2008): 1416-1424.

Valenta et al., "The use of polymers for dermal and transdermal delivery." European Journal of Pharmaceutics and Biopharmaceutics. 58.2 (2004): 279-289.

Wang et al., "Nano patterned PDMS for periodontal ligament fibroblast culture." Surface and Coatings Technology. 204.4 (2009): 525-530.

Wei et al., "Protein adsorption on materials surfaces with nanotopography." Chinese Science Bulletin. 52.23 (2007): 3169-3173.

Wood, M.A. "Colloidal lithography and current fabrication techniques producing in-plane nanotopography for biological applications." Journal of the Royal Society Interface. 4.12 (2007): 1-17.

Yao et al., "Nano-Surface Modification on Titanium Implants for Drug Delivery." Materials Research Society. (2007).

Yim et al., "Nanopattern-induced changes in morphology and motility of smooth muscle cells." Journal of Biomaterials. 58.1 (2005).

Abstract of Japanese Patent—JP2008237673, Oct. 9, 2008, 1 page.

Abstract of Japanese Patent—JP2009207733, Sep. 17, 2009, 1 page.

Abstract of Japanese Patent—JPH08337521, Dec. 24, 1996, 2 pages.

Inkyu Park et al., Towards the silicon nanowire-based sensor for intracellular biochemical detection, 6 pages, Apr. 1, 2007, Biosensors and Bioelectronics, vol. 22, No. 9-10.

Abstract of Japanese Patent—JP2001238964, Sep. 4, 2001, 1 page.

Berliner et al., "Impact of Transdermal Fentanyl on Quality of Life in Rheumatoid Arthritis", Clinical Journal of Pain, 2007, 23(6): 530-534.

Biggs et al., "Interactions with nanoscale topography: Adhesion quantification and signal transduction in cells of osteogenic and multipotent lineage," Journal of Biomedical Materials Research Part A, 2008 Wiley Periodicals, Inc., pp. 195-208.

Kumar et al. "Transdermal Drug Delivery System: An Overview." International Journal of Pharmaceutical Sciences Review and Research. 3.2 (2010): 49-54.

Verma et al., "Development of Transdermal Drug Dosage Formulation for the Anti-Rheumatic Ayurvedic Medicinal Plants", Ancient Sci. Life, 2007; 11:66-9.

International Search Report and Written Opinion for International Application No. PCT/IB2011/051863, dated Jan. 18, 2012, 4 pages.

Abstract of Japanese Patent—JP2008511382, Apr. 17, 2008, 2 pages.

Abstract of WIPO Patent—WO2006/075689, Jul. 20, 2006, 1 page.

\* cited by examiner square packing hexagonal packing

FIG. 25A
DN1
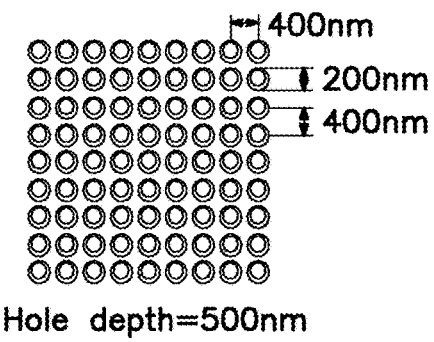
Hole depth=500nm
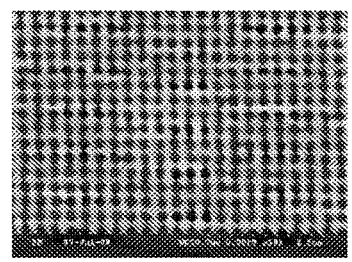
FIG. 25B
DN2
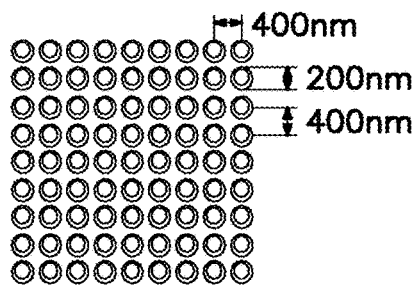
Hole depth=500nm
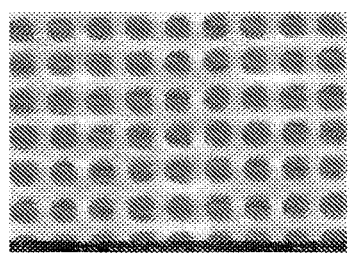
FIG. 25C
DN3
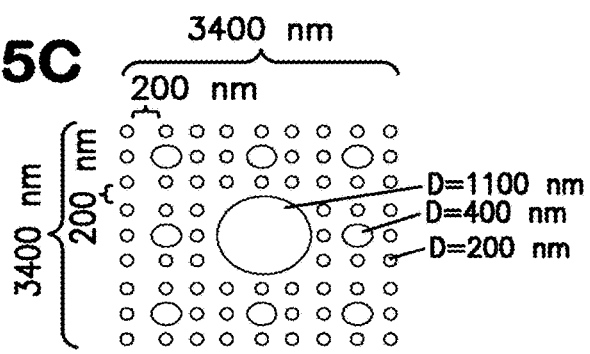
Hole depth=500nm
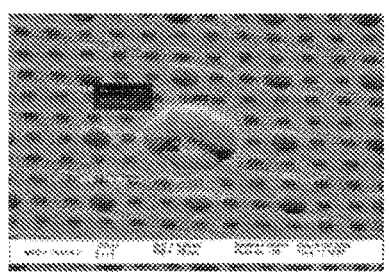
FIG. 25D
DN4
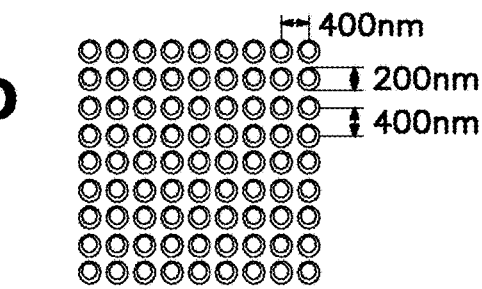
Hole depth=400–500nm
(Random Variation)
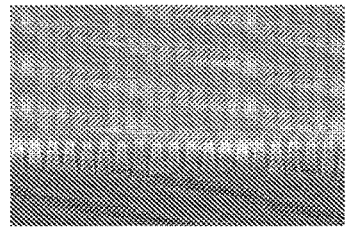

FIG. 25E
NTTAT2
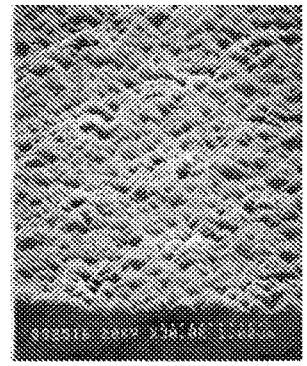
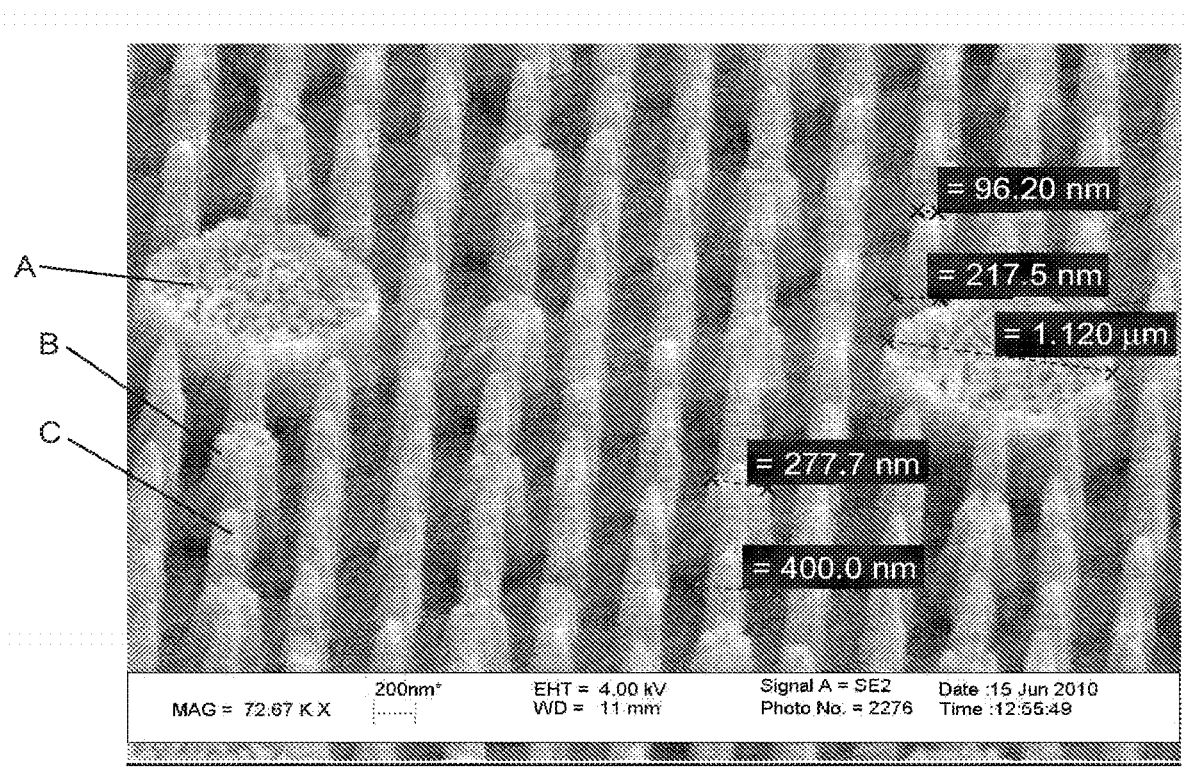
FIG. 26

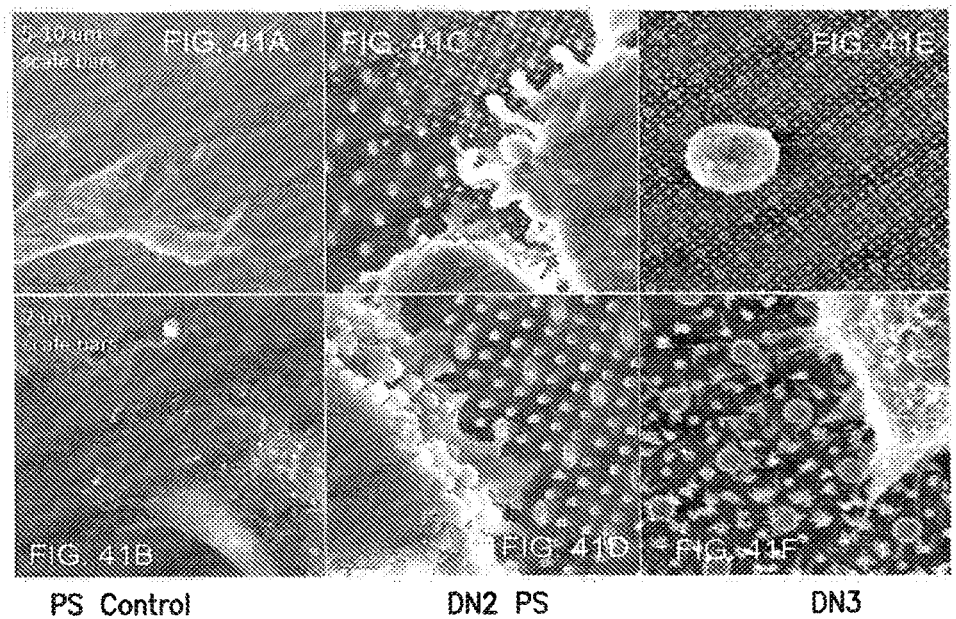
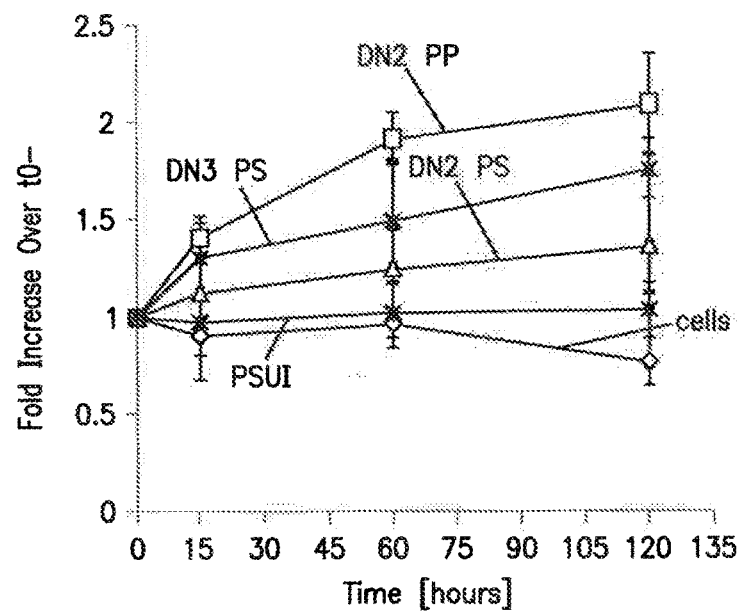
FIG. 42

METHOD FOR INCREASING PERMEABILITY OF A CELLULAR LAYER OF EPITHELIAL CELLS

CROSS-REFERENCE TO RELATED APPLICATIONS

This application is a continuation application of U.S. patent application Ser. No. 15/413,475, filed on Jan. 24, 2017, the entire contents and disclosure of which are hereby incorporated by reference herein in its entirety. U.S. patent application Ser. No. 15/413,475 is a continuation application of U.S. patent application Ser. No. 13/641,500, filed on Feb. 22, 2013 (now U.S. Pat. No. 9,586,044), the entire contents and disclosure of which are hereby incorporated by reference herein in its entirety. U.S. patent application Ser. No. 13/641,500 is a National Stage Entry of International Patent Application No. PCT/IB2011/051863, filed Apr. 27, 2011, which claims priority to U.S. Provisional Patent Application No. 61/328,723, filed on Apr. 28, 2010, U.S. Provisional Patent Application No. 61/411,085, filed on Nov. 8, 2010, and U.S. Provisional Patent Application No. 61/435,963, filed on Jan. 25, 2011, the entire contents and disclosure of which all are hereby incorporated by reference herein in their entirety.

BACKGROUND

Targeted drug delivery in which an agent (e.g., a drug or a therapeutic) is provided in an active state to a specific cell or tissue type at effective concentrations is a long sought goal. Many difficulties must be overcome to reach this goal. For instance, an agent must first be successfully delivered to the desired target. Primary delivery methods presently used include oral delivery and injections. However, injections are painful and both methods tend to provide bursts of agents rather than a preferred steady-state delivery. Additionally, the human body has developed many systems to prevent the influx of foreign substances, one of the most successful being a variety of structural components that prevent the free movement of compounds across barriers formed of epithelial tissue, e.g., the skin.

Transdermal delivery materials have been developed in an attempt to provide a painless route for delivery of active agents over a sustained period. In order to be successful, a transdermal scheme must deliver an agent across the epidermis, which has evolved with a primary function of keeping foreign substances out. The outermost layer of the epidermis, the stratum corneum, has structural stability provided by overlapping corneocytes and crosslinked keratin fibers held together by coreodesmosomes and embedded within a lipid matrix, all of which provides an excellent barrier function. Beneath the stratum corneum is the stratum granulosum, within which tight junctions are formed between keratinocytes. Tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in internal epithelium (e.g., the intestinal epithelium, the blood-brain barrier) as well as in the stratum granulosum of the skin. Beneath both the stratum corneum and the stratum granulosum lies the stratum spinosum. The stratum spinosum includes Langerhans cells, which are dendritic cells that may become fully functioning antigen-presenting cells and may institute an immune response and/or a foreign body response to an invading agent.

In spite of the difficulties of crossing the natural boundaries, progress has been made in attaining delivery of active agents across epithelial barriers. Unfortunately, transdermal delivery methods are presently limited to delivery of low molecular weight agents that have a moderate lipophilicity and no charge. Even upon successful crossing of the natural boundary, problems still exist with regard to maintaining the activity level of delivered agents and avoidance of foreign body and immune response.

The utilization of supplementary methods to facilitate transdermal delivery of active agents has improved this delivery route. For instance, microneedle devices have been found to be useful in transport of material into or across the skin. In general, a microneedle device includes an array of needles that may penetrate the stratum corneum of the skin and reach an underlying layer. Examples of microneedle devices have been described in U.S. Pat. No. 6,334,856 to Allen, et al. and U.S. Pat. No. 7,226,439 to Prausnitz, et al., both of which are incorporated herein by reference.

Researchers have gained understanding of the molecular world in which delivery activities occur in an attempt to improve transdermal delivery. For instance, chitosan has been found to be effective in opening tight junctions in the intestinal epithelium (see, e.g., Sapra, et al., *AAPS Pharm. Sci. Tech.*, 10(1), March, 2009; Kaushal, et al., *Sci. Pharm.*, 2009; 77; 877-897). In addition, the nanotopography of a surface adjacent to a cell has been found to affect adhesive characteristics between the two as well as to effect cell behavior including morphology, motility, cytoskeleton architecture, proliferation, and differentiation (see, e.g., Hart, et al., European Cells and Materials, Vol. 10, Suppl. 2, 2005; Lim, et al., J R Soc Interface, Mar. 22, 2005, 2(2), 97-108; Yim, et al., Biomaterials, September, 2005, 26(26), 5405-5413). As an extension of this initial research, nanotopography of supporting substrates has been examined for use in tissue engineering (see, e.g., U.S. Patent Application Publication Nos. 2008/0026464 to Borenstein, et al. and 2008/0311172 to Schapira, et al.).

While the above describe improvements in the art, further room for improvement exists. For instance, devices and methods that provide efficient delivery of active agents across a cellular barrier including epithelial tissue would be beneficial.

SUMMARY

In one aspect, a method for increasing permeability of a cellular layer of epithelial cells includes contacting the cellular layer with a nanostructured surface including a plurality of first nanostructures arranged thereon and projecting outward therefrom. A fractal dimension of the plurality of nanostructures is greater than 1. The permeability of the cellular layer by a compound is increased as compared to the permeability of the cellular layer prior to contact with the surface.

In another aspect, a method for increasing permeability of a cellular layer of epithelial cells includes contacting the cellular layer with a nanostructured surface comprising a plurality of nanostructures arranged thereon and projecting outward therefrom. A fractal dimension of the plurality of nanostructures is greater than 1. The permeability of the cellular layer to a compound having a molecular weight of greater than 400 Da is increased at least one-fold as compared to the permeability of the cellular layer prior to contact with the surface.

In yet another aspect, a method for transdermal delivery of a drug compound includes contacting a cellular layer with a nanostructured surface including a plurality of nanostructures arranged thereon and projecting outward therefrom. A fractal dimension of the plurality of nanostructures is greater than 1. The method also includes further contacting the cellular layer with a compound having a molecular weight of greater than 400 Da. The compound permeates across the cellular layer to provide a blood serum concentration of the compound of between about 500 nanograms and about 1000 nanograms per milliliter per square centimeter of nanostructured surface area.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIGS. 25A-25E illustrate several nanotopography patterns as described herein.

FIG. 26 is an SEM of a film including a nanopatterned surface.

FIGS. 41A-41F are scanning electron microscopy (SEM) images of cells cultured on nanopatterned surfaces as described herein.

FIG. 42 illustrates the effects on permeability to etanercept in a monolayer of cells on polypropylene or polystyrene films patterns with nanopatterns as described herein.

FIG. 47A is a cross section of skin that was in contact with a transdermal device defining a nanotopography thereon, and FIG. 47B is a cross section of skin that was in contact with a transdermal device including no pattern of nanotopography formed thereon.

DETAILED DESCRIPTION OF REPRESENTATIVE EMBODIMENTS

Figure 1:
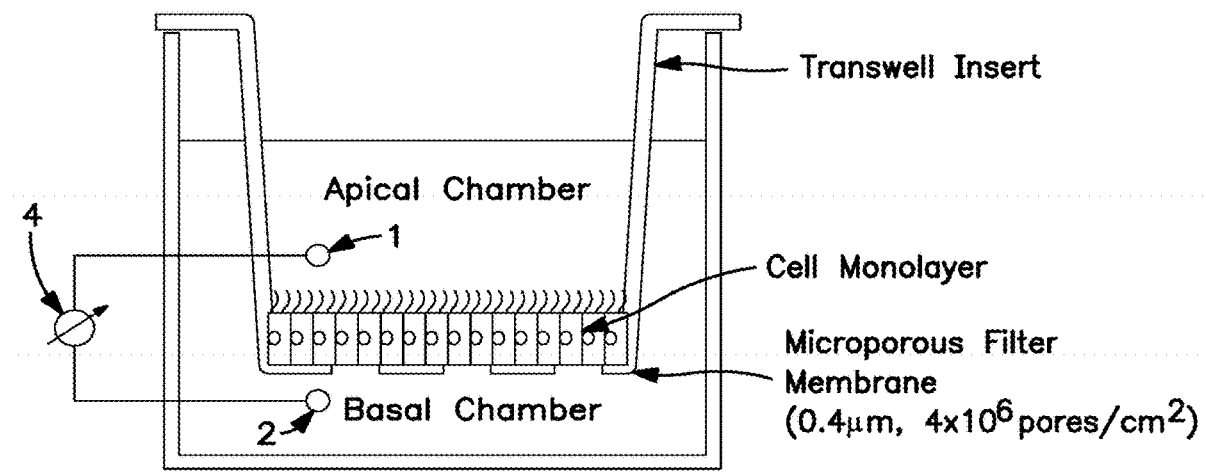
FIG. 1 illustrates a method for determining the TEER of a cellular layer.

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

In general, a method is disclosed for increasing the permeability of a cellular barrier that includes epithelial tissue. For instance, methods may increase the permeability of the epithelial tissue of the skin and may thus encourage transdermal delivery of a compound. While not wishing to be bound by any particular theory, it is believed that disclosed methods may affect both paracellular and transcellular transport across a cellular barrier layer. For example, it is believed that disclosed methods may affect formation and maintenance of cell/cell junctions including tight junctions and/or desmosomes. Opening of the tight junctions may provide a paracellular route for improved delivery of active agents, particularly large molecular weight active agents and/or agents that exhibit high or low lipophilicity that have previously been blocked from transdermal delivery. Additionally, it is believed that interaction between cells and a device may encourage transcellular transport through the cells and across the barrier.

According to one embodiment, the increased permeability of a cellular layer may be determined through determination of the transepithelial electrical resistance (TEER, also referred to herein as transepithelial resistance or TER) across the layer. As in generally known, a decrease in TEER across a cellular layer is a good indication of an increase in the permeability of a cell layer due to, for instance, the lack of formation or the opening of tight junctions of a cell layer. It is clear that in endothelia and certain epithelia, the ability of tight junctions to restrict paracellular flux is not immutable. Rather, this gate function of tight junctions is capable of dynamic regulation (Madara, 1988; Rubin, 1992). In particular, the activation of signal transduction pathways either by receptor ligands or specific membrane-permeant modulators may have striking effects on the permeability of the paracellular pathway. For example, protein kinase C activation causes a substantial increase in the permeability of tight junctions in MDCK cells (Ojakian, 1981), an epithelial cell line. Cyclic AMP elevation decreases permeability in brain endothelial cells in culture, a model system for the study of the blood-brain barrier (Rubin et al., 1991). Cyclic AMP also decreases tight junction permeability in peripheral endothelial cells (Stelzner et al., 1989; Langeier et al., 1991).

The permeability properties of the tight junction also depend upon the integrity of the adherens junction. Disruption of the adherens junction by removal of extracellular $Ca^{2+}$ leads to an opening of tight junctions in MDCK cells (see Martinez-Palomo et al., 1980; Gumbiner and Simons, 1986) and in endothelial cells (Rutten et al., 1987). Protein kinases appear to be involved in this indirect modulation of tight junctional integrity in MDCK cells (Citi, 1992). The Ca2+-sensitive components of the adherens junction complex are the cadherins (reviewed by Geiger and Avalon, 1992). These transmembrane proteins mediate intercellular adhesiveness in a $Ca^{2+}$-dependent, homophilic manner via their extracellular domains. The cytoplasmic domain of the cadherins associates with three further proteins termed α-, β- and γ-catenin (Ozawa et al., 1989), which link the cadherins to the actin cytoskeleton and are required for cadherin adhesiveness (Hirano et al., 1987; Nagaruchi and Takeichi, 1988; Ozawa et al., 1990; Kintner, 1992; see Stappert and Kemler, 1993).

Contact between an epithelial layer and a device surface that includes a pattern of structures fabricated on the surface, at least a portion of which are fabricated on a nanometer scale, may increase the permeability and decrease the TEER of the epithelial layer. For instance, the TEER of an epithelial layer may drop to less than about 95%, less than about 85%, or less than about 70% of its initial value following contact between the layer and a nanopatterned surface for a period of time. By way of example, following about 30 minutes of contact between an epithelial layer and a surface including a pattern of nanostructures thereon, the TEER across the layer may be between about 90% and about 95% of its initial value. Following 60 minutes, the TEER across the layer may be between about 80% and about 90% of its initial value, and following 120 minutes, the TEER across the layer may be between about 60% and about 75% of its initial value.

FIG. 1 illustrates one method for determining the TEER across an epithelial layer. In this embodiment, a cell layer, for instance an epithelial cell monolayer, may be grown or otherwise located at the base of an apical chamber. The base of the apical chamber may be a microporous filter membrane, as shown, to allow flow between the two chambers and prevent individual cells from passing into the basal chamber. By way of example, the microporous filter membrane may include pores of about 0.4 micrometers at a density of about $4 \times 10^6$ pores per centimeter. Of course, the specific parameters of the various system components are not critical, and may be varied as is known in the art. The apical chamber may be defined by a transwell insert that may fit into a larger well, as shown, thereby defining the basal chamber of the system. During use a first electrode 1 and a second electrode 2 may be located on either side of the epithelial cell monolayer and an ohmmeter 4 may be connected between the two electrodes. The ohmmeter 4 may provide the TEER across the cell monolayer. Systems for determining the TEER across a cell layer are known, for instance, the Millicell™ electrical resistance system (available from Millipore of Bedford, Mass.) may be utilized.

Contact between an epithelial cell layer and a surface including nanostructures fabricated thereon may lead to a drop in TEER, which indicates an increase in layer permeability. Accordingly, following contact between an epithelial layer and a nanostructured surface, the ability to transport compounds across the layer may be greatly increased. This may improve transdermal delivery of compounds that previously could not be delivered efficiently in this fashion. For example, the transdermal delivery of high molecular weight compounds, lipophilic compounds and/or charged compounds may be improved through utilization of disclosed methods and devices.

The device may include a plurality of nano-sized structures fabricated on the surface intended to contact an epithelial layer. As utilized herein, the term 'fabricated' generally refers to a structure that has been specifically designed, engineered, and/or constructed so as to exist a surface of the device and is not to be equated with a surface feature that is merely an incidental product of the device formation process. Thus, there will be a predetermined pattern of nanostructures on the surface of the microneedles.

Devices include those intended for use in contact with an epithelial layer, for instance transdermal patches and the like. The device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon-based materials such as silicon dioxide, and polymers may be utilized. Typically, the device may be formed of a biocompatible material that is capable of carrying a pattern of structures as described herein on a surface. The term "biocompatible" generally refers to a material that does not substantially adversely affect the cells or tissues in the area where the device is to be delivered. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with polyethylene glycol, polyanhydrides, poly(ortho)esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluorethylene, and polyesters. The device may likewise be non-porous or porous in nature, may be homogeneous or heterogeneous across the device with regard to materials, geometry, solidity, and so forth, and may have a rigid fixed or a semi-fixed shape.

Regardless of the materials employed, the device may be used for interaction with epithelial tissue, such as in delivery of a bioactive agent across a barrier layer. For example, the device may be used to transport a substance across one or more layers of the skin. During use, the device may interact with surrounding biological components and regulate or modulate (i.e., change) intracellular and/or intercellular signal transduction associated with cell/cell interactions. For instance, through interaction between the nanotopography on a surface of the device and surrounding biological materials or structures, the device may regulate and/or modulate membrane potential, membrane proteins, and/or intercellular junctions (e.g., tight junctions, gap junctions, and/or desmasomes) so as to increase the permeability of the layer.

In addition, the device may be utilized for transdermal delivery without instigating a foreign body or immune response.

The device may be a patch that defines a nanotopography at the skin contacting surface thereof, for example a transdermal patch. A patch is not limited to a transdermal patch, however. For instance, a patch may be useful in transport of material across epithelial barriers in addition to or alternative to the skin, such as the blood-brain barrier, mucosal tissues, gastric tissues, blood and lymph vessels, and so forth.

Figure 2:
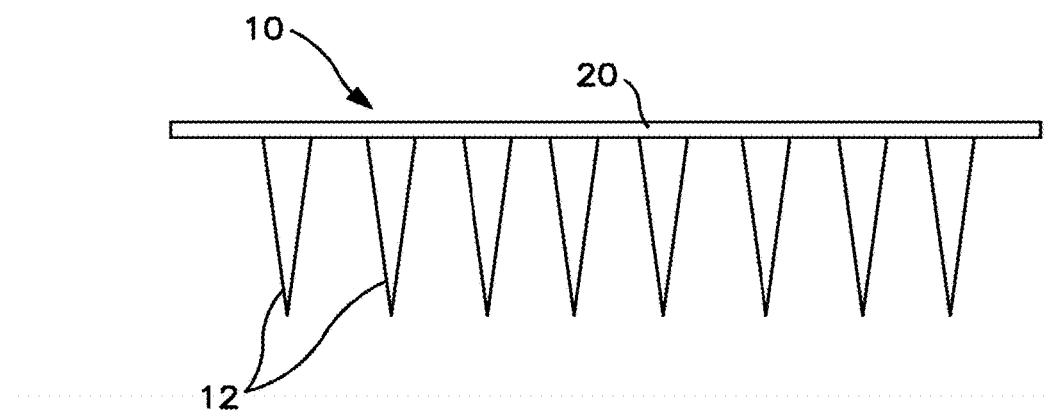
FIG. 2 illustrates one embodiment of a microneedle device.
Figure 3:
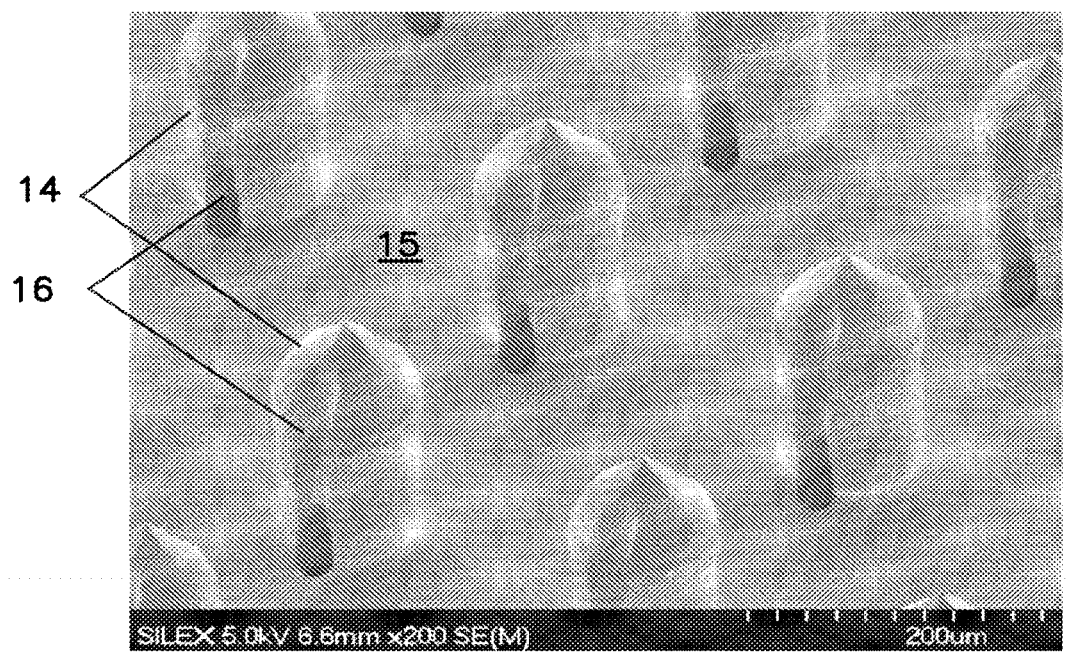
FIG. 3 illustrates another embodiment of a microneedle device.

In one embodiment, the device may include a microneedle. For example, the device may be a transdermal patch that defines a plurality of microneedles on the skin contacting surface of the device. FIG. 2 illustrates a typical microneedle device 10. As may be seen, the device includes an array of individual needles 12; each formed to a size and shape so as to penetrate a biological barrier without breakage of the individual microneedles. Microneedles 12 may be solid, as in FIG. 2, porous, or may include a hollow portion. A microneedle may include a hollow portion, e.g., an annular bore that may extend throughout all or a portion of the needle, extending parallel to the direction of the needle or branching or exiting at a side of the needle, as appropriate. For example, FIG. 3 illustrates an array of microneedles 12 each including a channel 16 in a side of the needles as may be utilized for, e.g., delivery of an agent to a subdermal location. For instance, a channel 16 may be in at least partial alignment with an aperture in base 15 so as to form a junction between the aperture and channel 16 allowing the passage of a substance through the channel 16.

The dimensions of the channel 16, when present, may be specifically selected to induce capillary flow of a drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

An individual microneedle may have a straight or a tapered shaft. In one embodiment, the diameter of a microneedle may be greatest at the base end of the microneedle and taper to a point at the end distal the base. A microneedle may also be fabricated to have a shaft that includes both a straight (untapered) portion and a tapered portion.

A microneedle may be formed with a shaft that is circular or non-circular in cross-section. For example, the cross-section of a microneedle may be polygonal (e.g. star-shaped, square, triangular), oblong, or any other shape. The shaft may have one or more bores and/or channels.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The length of a microneedle will generally depend upon the desired application. For instance, a microneedle may be between about 1 micrometer and about 1 millimeter in length, for instance about 500 micrometers or less, or between about 10 micrometers and about 500 micrometers, or between about 30 micrometers and about 200 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

Referring again to FIG. 2, microneedles may be held on a substrate 20 (i.e., attached to or unitary with a substrate) such that they are oriented perpendicular or at an angle to the substrate. In one embodiment, the microneedles may be oriented perpendicular to the substrate and a larger density of microneedles per unit area of substrate may be provided. However, an array of microneedles may include a mixture of microneedle orientations, heights, materials, or other parameters. The substrate 20 may be constructed from a rigid or flexible sheet of metal, ceramic, plastic or other material. The substrate 20 may vary in thickness to meet the needs of the device, such as about 1000 micrometers or less, in some embodiments from about 1 to about 500 micrometers, and in some embodiments, from about 10 to about 200 micrometers.

A microneedle surface may define a nanotopography thereon in a random or organized pattern so as to contact an epithelial tissue and increase the permeability of the tissue.

Figure 4:
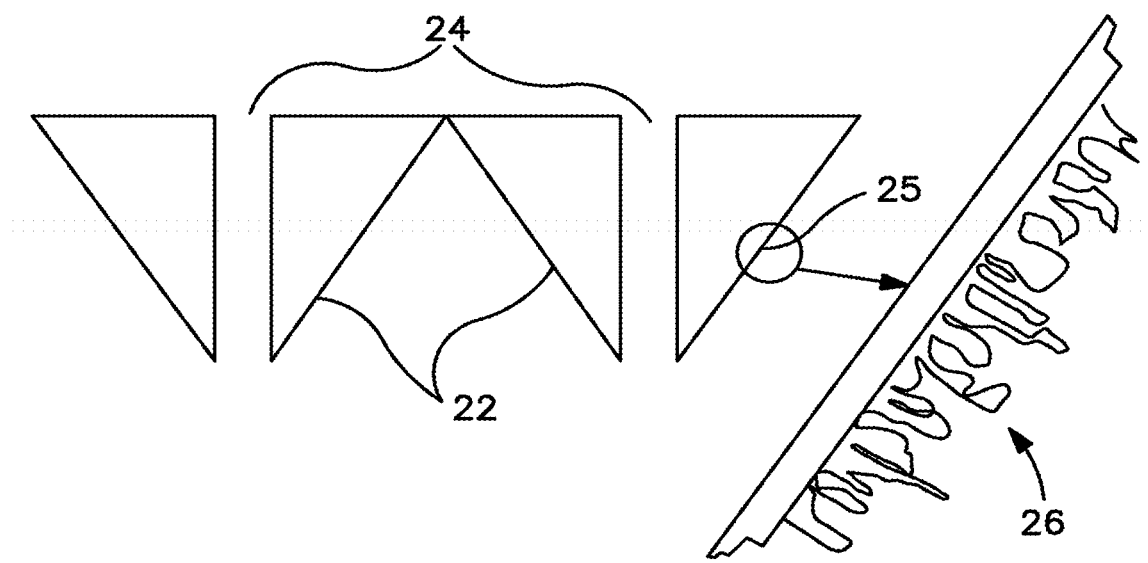
FIG. 4 illustrates one embodiment of a microneedle including a surface that defines a nanotopography.

FIG. 4 schematically illustrates the ends of two representative microneedles 22 defining a nanotopography thereon. In this particular embodiment, microneedles 22 define a central bore 24 as may be used for delivery of an agent via the microneedles 22. The surface 25 of microneedle 22 may define nanotopography 26. In this particular embodiment, the nanotopography 26 defines a random pattern on the surface 25 of the microneedle 22.

The device may include a plurality of identical structures formed on a surface or may include different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

By way of example, a transdermal patch surface defining a complex nanotopography may include structures of the same general shape (e.g., pillars) and the pillars may be formed to different scales of measurement (e.g., nano-scale pillars as well as micro-scale pillars). In another embodiment, a patch may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures may generally be greater than about 5 nanometers, for instance greater than about 10 nanometers, or greater than about 20 nanometers. For example, the nanostructures may define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

Figure 5:
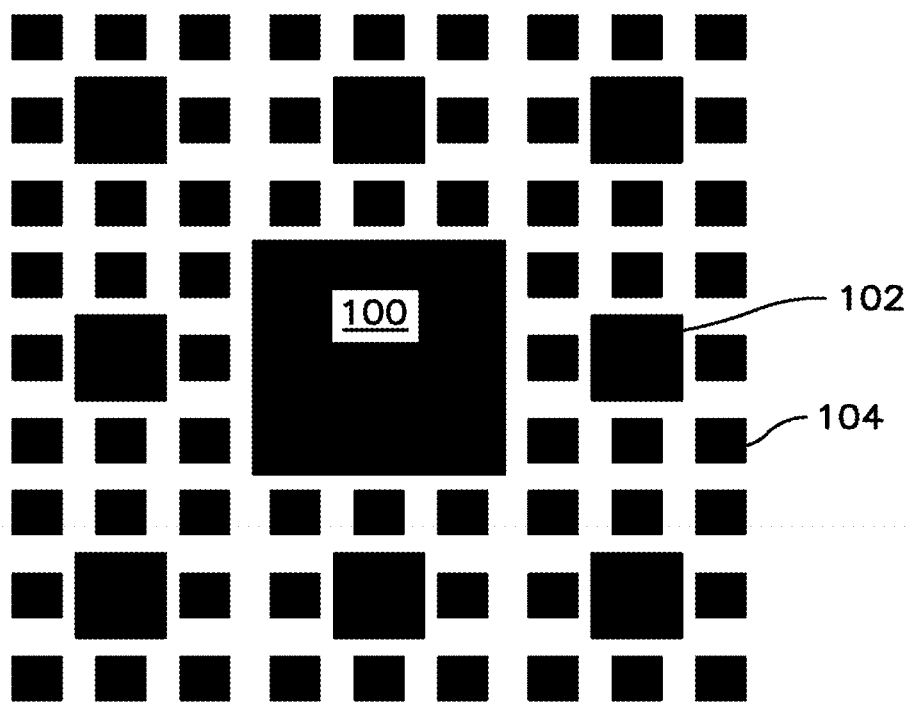
FIG. 5 illustrates one embodiment of a complex pattern that may be formed on a device surface.

FIG. 5 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes may include larger structures having a cross-sectional dimension formed on a larger scale, e.g., microstructures having a cross-sectional dimension greater than about 500 nanometers in combination with smaller nanostructures. In one embodiment, microstructures of a complex nanotopography may have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 5 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 5 have a cross-sectional dimension of about 400 nanometers, and pillars 104 have a cross-sectional dimension of about 200 nanometers.

A nanotopography may be formed of any number of different elements. For instance, a pattern of elements may include two different elements, three different elements, an example of which is illustrated in FIG. 5, four different elements, or more. The relative proportions of the recurrence of each different element may also vary. In one embodiment, the smallest elements of a pattern will be present in larger numbers than the larger elements. For instance in the pattern of FIG. 5, there are eight pillars 104 for each pillar 102, and there are eight pillars 102 for the central large pillar 100. As elements increase in size, there may generally be fewer recurrences of the element in the nanotopography. By way of example, a first element that is about 0.5, for instance between about 0.3 and about 0.7 in cross-sectional dimension as a second, larger element may be present in the topography about five times or more than the second element. A first element that is approximately 0.25, or between about 0.15 and about 0.3 in cross-sectional dimension as a second, larger element may be present in the topography about 10 times or more than the second element.

The spacing of individual elements may also vary. For instance, center-to-center spacing of individual structures may be between about 50 nanometers and about 1 micrometer, for instance between about 100 nanometers and about 500 nanometers. For example, center-to-center spacing between structures may be on a nano-sized scale. For instance, when considering the spacing of nano-sized structures, the center-to-center spacing of the structures may be less than about 500 nanometers. This is not a requirement of a topography, however, and individual structures may be farther apart. The center-to-center spacing of structures may vary depending upon the size of the structures. For example, the ratio of the average of the cross-sectional dimensions of two adjacent structures to the center-to-center spacing between those two structures may be between about 1:1 (e.g., touching) and about 1:4, between about 1:1.5 and about 1:3.5, or between about 1:2 and about 1:3. For instance, the center to center spacing may be approximately double the average of the cross-sectional dimensions of two adjacent structures. In one embodiment, two adjacent structures each having a cross-sectional dimension of about 200 nanometers may have a center-to-center spacing of about 400 nanometers. Thus, the ratio of the average of the diameters to the center-to-center spacing in this case is 1:2.

Structure spacing may be the same, i.e., equidistant, or may vary for structures in a pattern. For instance, the smallest structures of a pattern may be spaced apart by a first distance, and the spacing between these smallest structures and a larger structure of the pattern or between two larger structures of the pattern may be the same or different as this first distance.

For example, in the pattern of FIG. 5, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures may be equidistant from one another or any variation in distances. In one embodiment, different structures may be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, nanostructures may have an aspect ratio falling within any of these ranges.

Figure 6:
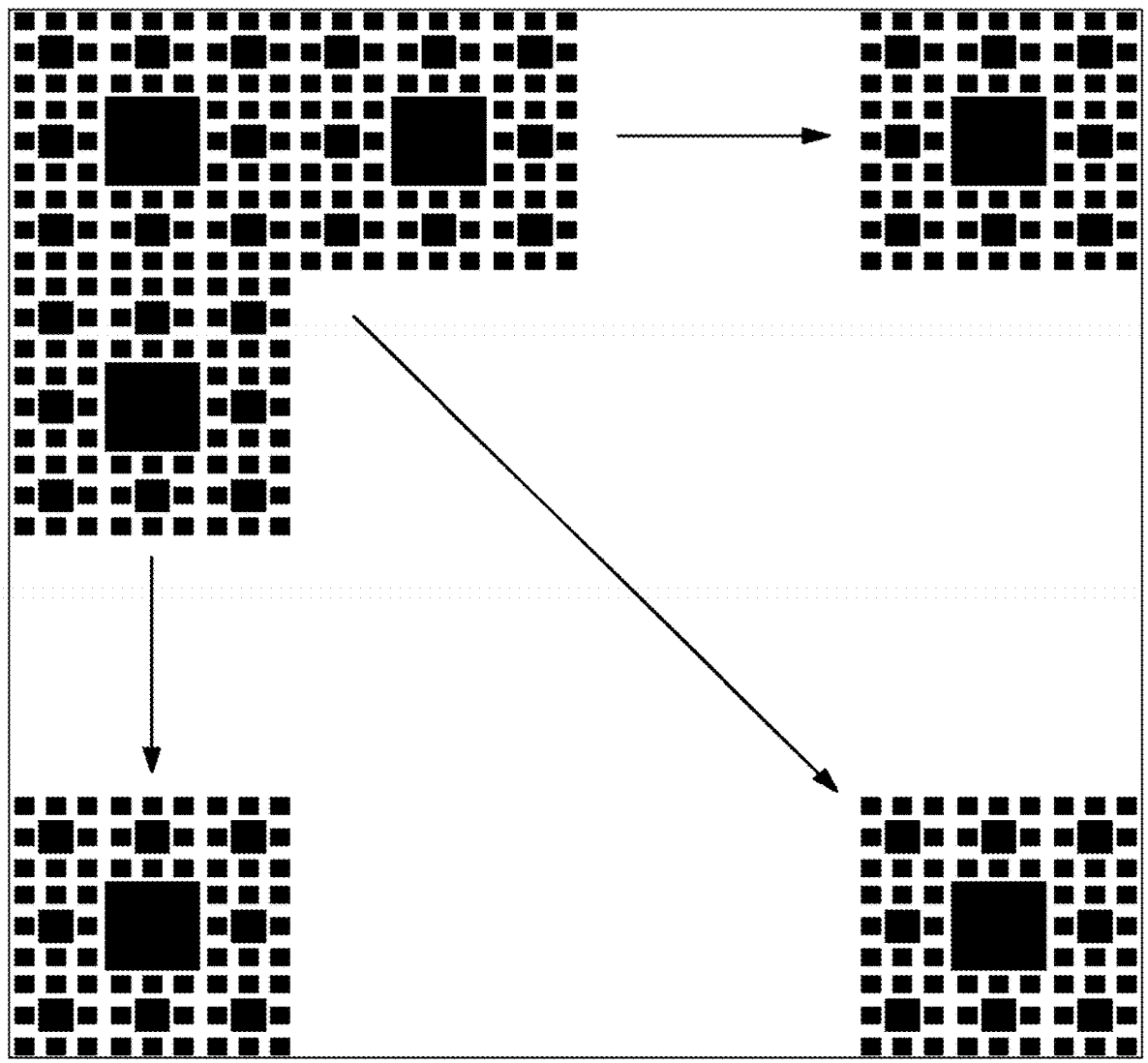
FIG. 6 illustrates a pattern including multiple iterations of the complex pattern of FIG. 5.

The device surface may include a single instance of a pattern, as shown in FIG. 5, or may include multiple iterations of the same or different patterns. For example, FIG. 6 illustrates a surface pattern including the pattern of FIG. 5 in multiple iterations over a surface.

While not wishing to be bound to any particular theory, it is believed that the increase in permeability of a contacting epithelial surface may be brought about due to the physical characteristics of a contacting surface including fabricated nanostructures as compared to a contacting surface that does not include the fabricated nanostructures. For example, the fabrication of nanotopography on a surface may increase the surface area without a corresponding increase in volume, which may affect the interaction of the surface with surrounding epithelial cells and increase the permeability of the cellular layer. For instance, increase in the surface area to volume ratio is believed to encourage mechanical interaction between the nanotopography and surrounding proteins, e.g., extracellular matrix (ECM) proteins and/or plasma membrane proteins. As utilized herein, the term "protein" generally refers to a molecular chain of amino acids that is capable of interacting structurally, enzymatically or otherwise with other proteins, polypeptides or any other organic or inorganic molecule.

In general, the surface area to volume ratio of a nanopatterned surface may be greater than about 10,000 cm$^{-1}$, greater than about 150,000 cm$^{-1}$, or greater than about 750,000 cm$^1$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference.

The BET surface area may be less than about 5 m$^2$/g, in one embodiment, or between about 0.1 m$^2$/g and about 4.5 m$^2$/g. Values for surface area and volume may also be estimated from the geometry of molds used to form a surface, according to standard geometric calculations. For example, the volume may be estimated according to the calculated volume for each pattern element and the total number of pattern elements in a given area, e.g., over the surface of a single microneedle.

For a device that defines a complex pattern nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

Figure 7:
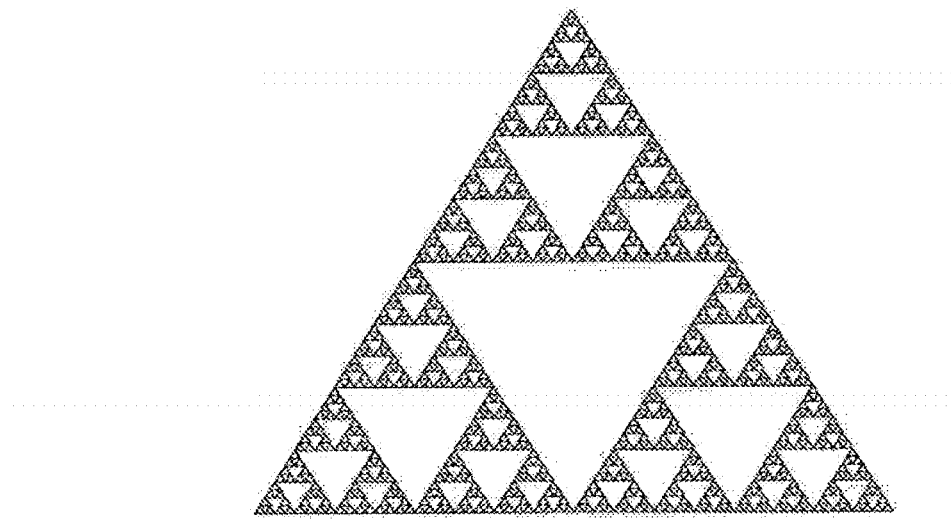
FIG. 7 illustrates a Sierpinski triangle fractal.

For example, when considering the 2 dimensional fractal known as the Sierpenski triangle illustrated in FIG. 7, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 5 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

Figures 8A, 8B:
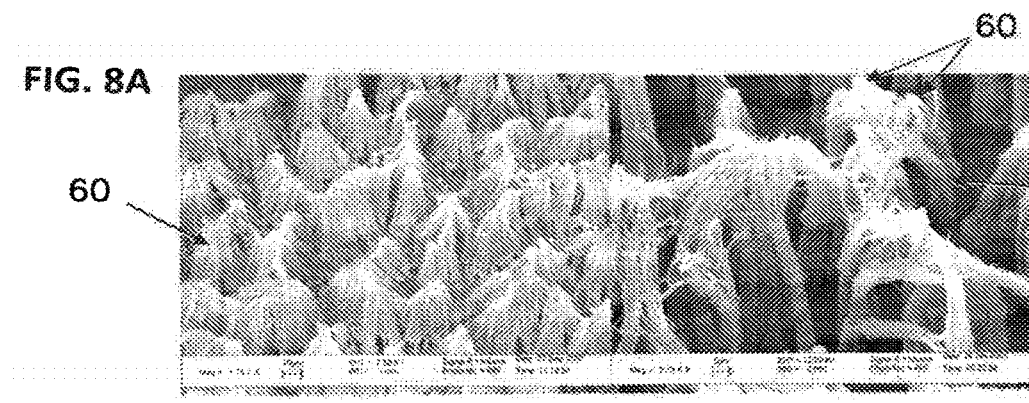
FIGS. 8A-8D illustrate complex fractal and fractal-like nanotopographies.

FIGS. 8A and 8B illustrate increasing magnification images of another example of a complex nanotopography. The nanotopography of FIGS. 8A and 8B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 8A and 8B). Structures formed on a surface that have an aspect ratio greater than about 1 may be flexible, as are the structures illustrated in FIGS. 8A and 8B, or may be stiff.

Figures 8C, 8D:
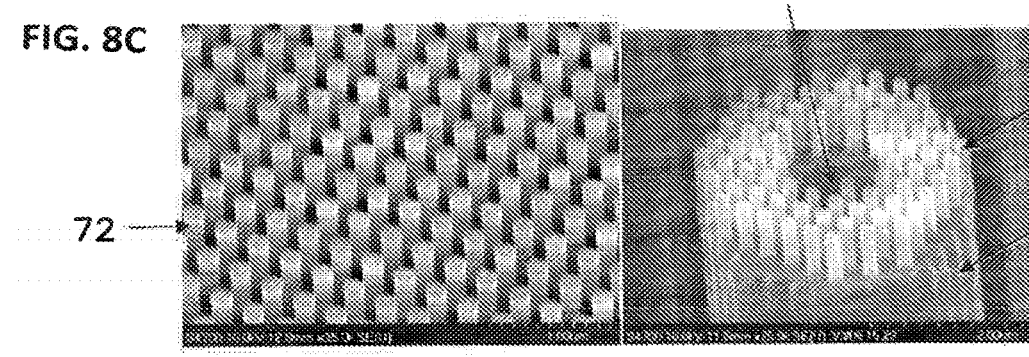

FIGS. 8C and 8D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 8C and 8D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 9:
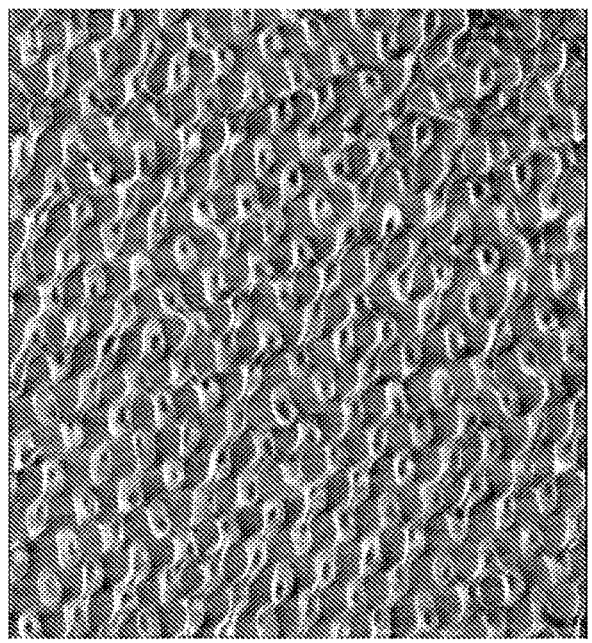
FIG. 9 illustrates another complex pattern that may be formed on a device surface.

FIG. 9 illustrates another pattern including nano-sized structures as may be formed on the device surface. As may be seen, in this embodiment, individual pattern structures may be formed at the same general size, but with different orientations and shapes from one another.

In addition to or alternative to the examination of surface area to volume ratio and/or fractal dimension, the device surface including a nanotopography thereon may be characterized by other methods including, without limitation, surface roughness, elastic modulus, surface energy, and so forth.

Methods for determining the surface roughness are generally known in the art. For instance, an atomic force microscope process in contact or non-contact mode may be utilized according to standard practice to determine the surface roughness of a surface. Surface roughness that may be utilized to characterize a nanopatterned surface may include the average roughness ($R_A$), the root mean square roughness, the skewness, and/or the kurtosis. In general, the average surface roughness (i.e., the arithmetical mean height of the surface area roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The device may be characterized by the elastic modulus of the nanopatterned surface, for instance by the change in elastic modulus upon the addition of a nanotopography to a surface. In general, the addition of a plurality of structures forming nanotopography on a surface may decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the device including nanotopography thereon may exhibit a decrease in elastic modulus of between about 35% and about 99%, for instance between about 50% and about 99%, or between about 75% and about 80%. By way of example, the effective compression modulus of a nanopatterned surface may be less than about 50 MPa, or less than about 20 MPa. In one embodiment the effective compression modulus may be between about 0.2 MPa and about 50 MPa, between about 5 MPa and about 35 MPa, or between about 10 MPa and about 20 MPa. The effective shear modulus may be less than about 320 MPa, or less than about 220 MPa. For instance, the effective shear modulus may be between about 4 MPa and about 320 MPa, or between about 50 MPa and about 250 MPa, in one embodiment.

The device including nanotopography thereon may also exhibit an increase in surface energy as compared to a similar device that does not have a surface defining a pattern of nanotopography thereon. For instance, a surface including a nanotopography formed thereon may exhibit an increase in surface energy as compared to a similar surface of the same materials and formed according to the same methods, but for the inclusion of a pattern of nanotopography on the surface. For instance, the water contact angle of a surface including a nanotopography thereon may be greater than about 80°, greater than about 90°, greater than about 100°, or greater than about 110°. For example, the water contact angle of a surface may be between about 80° and about 150°, between about 90° and about 130°, or between about 100° and about 120°, in one embodiment.

Figure 10A:
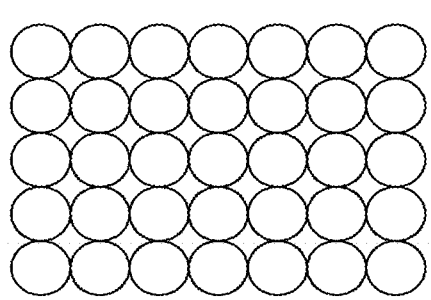
FIGS. 10A-10C illustrate exemplary packing densities as may be utilized for nano-sized structures as described herein including a square packing design (FIG. 10A), a hexagonal packing design (FIG. 10B), and a circle packing design (FIG. 10C).
Figure 10B:
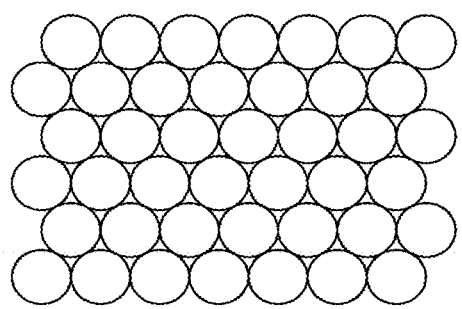
Figure 10C:
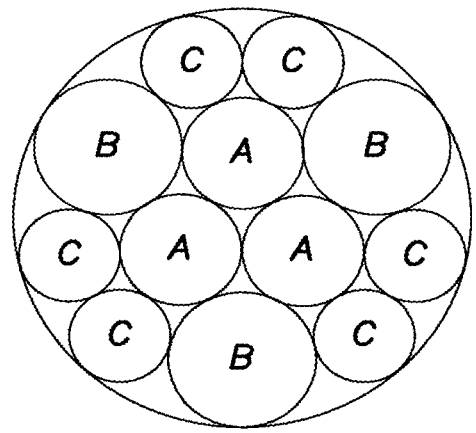

When forming nanostructures on the surface of the device, the packing density of the structures may be maximized. For instance, square packing (FIG. 10A), hexagonal packing (FIG. 10B), or some variation thereof may be utilized to pattern the elements on a substrate. When designing a pattern in which various sized elements of cross sectional areas A, B, and C are adjacent to one another on a substrate, circle packing as indicated in FIG. 10C may be utilized. Of course, variations in packing density and determination of associated alterations in characteristics of a surface are well within the abilities of one of skill in the art.

During use, the device may interact with one or more components of the contacting epithelial tissue to increase permeability of the tissue. Epithelial tissue is one of the primary tissue types of the body. Epithelial tissue as may be rendered more permeable according to the present disclosure may include both simple and stratified epithelium, including both keratinized epithelium and transitional epithelium. In addition, epithelial tissue encompassed herein may include any cell types of an epithelial layer including, without limitation, keratinocytes, squamous cells, columnar cells, cuboidal cells and pseudostratified cells.

The nanotopography of the device may provide improved interaction between the device and biological components of the epithelial tissue of the delivery area. For instance, microneedles of a transdermal device may interact directly with ECM proteins and/or individual cells such as keratinocytes. Longer needles on transdermal devices may be utilized to access epithelial components of the dermis, for instance blood cells of the capillary bed. In addition to increasing permeability of an epithelial layer, and due to the improved interaction between the device and local biological components, the surrounding tissue may be less likely to exhibit a foreign body response, which may decrease local inflammation and improve delivery of active agents. In one embodiment, the device may play a more active role in agent delivery. For instance, interaction between a nanotopography and the surrounding biological components may encourage delivery of high molecular weight materials, for instance through opening of tight junctions in the stratum granulosum.

While not wishing to be held to any particular theory, it is believed that the fabricated nanotopography facilitates improved interaction with biological components through two mechanisms. According to one mechanism, a nanotopography may facilitate the ability of the device to mimic the ECM at a delivery site. For instance, the nanotopography of the device may mimic one or more components of the epithelial tissue at a delivery site. In use, an epithelial cell may contact the nanotopography of the device and react in a similar fashion to typical contact with a natural structure (e.g., a basement membrane protein) that the nanotopography mimics. Accordingly, the device may directly interact with a cell to regulate or modulate (i.e., change) cell behavior, e.g., cell signal transduction, thereby improving delivery of an agent across natural barriers.

According to a second mechanism, a nanotopography may interact with non-cellular biological components of the local epithelial tissue such as ECM proteins. For instance, ECM proteins may be adsorbed and desorbed from the surface of the device. The adsorption/desorption of ECM proteins may alter the chemistry of the local environment, which may lead to alterations in cell behavior. According to this second mechanism, the device may indirectly affect the behavior of an epithelial cell. For example, the adsorption of one or more ECM proteins at the surface of the device may indirectly regulate or modulate intracellular and/or intercellular signal transduction.

Due to improved interaction with surrounding biological components, the devices may facilitate improved uptake of a delivered agent. For example, the pharmacokinetic (PK)

profile (i.e., the profile of absorption through the epithelial membranes) of a protein therapeutic may be enhanced through utilization of a device including a pattern of nanotopography. By way of example, a protein therapeutic having a molecular weight of over 100 kDa, for instance between about 100 kDa and about 200 kDa, or about 150 kDa, may be delivered transdermally via a patch defining a nanotopography thereon. In one embodiment, a patch may be utilized to deliver a single dose of the protein therapeutic, for instance between about 200 and about 500 µL, or about 250 µL. Following attachment of the transdermal patch to the skin, the recipient may exhibit a PK profile that reflects a rapid rise in blood serum concentration up to between about 500 and about 1000 nanograms therapeutic per milliliter per square centimeter of patch area, for instance between about 750 and about 850 nanograms therapeutic per milliliter per square centimeter of patch area, within about 1 to about 4 hours of administration. This initial rapid rise in blood serum level, which reflects rapid uptake of the therapeutic across the dermal barrier, may be followed by a less rapid decline of blood serum concentration over between about 20 and about 30 hours, for instance over about 24 hours, down to a negligible blood serum concentration of the therapeutic. Moreover, the rapid uptake of the delivered therapeutic may be accompanied by little or no inflammation. Specifically, in addition to promoting improved delivery of an agent across a transdermal barrier, the devices may also limit foreign body response and other undesirable reactions, such as inflammation. Use of previously known devices, such as transdermal patches with no nanotopography defined at the skin contacting surface, often led to local areas of inflammation and irritation.

Structures of the nanotopography may mimic and/or interact with one or more ECM protein such as collagen, laminin, fibronectin, etc. This may directly or indirectly alter a cell membrane protein with regard to one or more characteristics such as conformation, free energy, and local density, which may in turn alter the interaction of the cell with neighbors and affect formation or maintenance of junctions between the cells, thereby increasing permeability of the cellular layer.

More specifically, interaction of the device with components of an epithelial layer is believed to modulate (i.e., change) the structure of intercellular junctions of the layer, and increase paracellular transport across the layer. An intracellular junction may be at least one junction selected from the group consisting of tight junctions, gap junctions, and desmasomes. By way of example, interaction between biological components and structures of a nanotopography may modulate proteins of a cellular network so as to induce the opening of tight junctions of the stratum granulosum, thereby providing improved delivery of an active agent across the epidermis, and in one particular embodiment, a high molecular weight active agent.

The device may increase permeability of an epithelial cell layer through alteration in the focal adhesion of the cells. Focal adhesions are large assemblies of materials that may include 100 or more different proteins at any one time. They are dynamic in most cell types and provide a route for the transmission of information, both mechanical and chemical, from the ECM to the inner cell. Modification of focal adhesions takes place upon changes in the molecular composition, the physical structure, as well as physical forces present in the ECM.

Focal adhesions allow connection between the cytoskeleton and the ECM and are generally considered to be a signaling hub for both mechanical force and chemical signal transmission. The bulk of focal adhesions are beneath the cellular membrane, with connection to the ECM generally via integrins, though communication may also be via other transmembrane materials including hyaluronan and heparin-sulfate binding proteins.

Primary proteins within focal adhesions that may be affected by the presence of a nanotopography in the area of the cell surface include vinculin, paxilin, talin, α-actinin, and zyxin. The focal adhesion proteins transmit information to the cytoskeleton, for instance via interaction with actin, and throughout the cytoplasm. Focal adhesions are in a constant state of flux, however, and proteins are continually associating and disassociating with the complex, relating information from the ECM to other parts of the cell.

Interaction between individual cells and structures of the nanotopography may induce the passage of an agent through a barrier cell and encourage transcellular transport. For instance, interaction with keratinocytes of the stratum corneum may encourage the partitioning of an agent into the keratinocytes, followed by diffusion through the cells and across the lipid bilayer. While an agent may cross a cellular barrier according to both paracellular and transcellular routes, the transcellular route may be predominate for highly hydrophilic molecules, though, of course, the predominant transport path may vary depending upon the nature of the agent, hydrophilicity being only one defining characteristic.

Cells in the local area surrounding the device may also maintain an anti-inflammatory microenvironment as the device may better mimic the local environment either directly or indirectly due to protein adsorption at the surface. Thus, materials may be delivered by use of the device without development of a foreign body or immune response.

Specific cell types that may be directly or indirectly affected by the presence of a microneedle may include cells of the surrounding dermal connective tissue. For instance, a microneedle surface defining nanotopography may be located in an area that includes Langerhans cells, macrophages, and/or T-cells without triggering a foreign body or immune response. Langerhans cells may take up and process an antigen to become a fully functional antigen presenting cell. Macrophages and T-cells play a central role in the initiation and maintenance of the immune response. Once activated by pathological or immunogenic stimuli, for instance via a Langerhans cell, T-cells may release IL-2, IL-4, INF-α, and other inflammatory cytokines. Macrophages respond in the process by releasing a host of inflammatory mediators, including TNF-α, IL-1, IL-8, IL-11, IL-12, nitric oxide, IL-6, GM-CSF, G-CSF, M-CSF, IFN-α, IFN-β and others. Released cytokines activate other immune cells and some may also act as independent cytotoxic agents. Excessive release of macrophage and T-cell derived inflammatory mediators may lead to damage of normal cells and surrounding tissues.

Without wishing to be bound to any particular theory, it is believed that through interaction with a nanopatterned substrate, individual cells may up- or down-regulate the production of certain cytokines, including certain chemokines. Through that alteration in expression profile, cellular response to a drug delivery device may be minimized. For example, inflammation and/or foreign body response may be minimized through upregulation of one or more anti-inflammatory cytokines and/or down-regulation of one or more pro-inflammatory cytokines. Many cytokines have been characterized according to effect on inflammation. Pro-inflammatory cytokines that may demonstrate altered expression profiles when expressing cells are affected by the presence of a device including a nanotopography fabricated thereon may include, without limitation, IL-la, IL-1β, IL-2, IL-6, IL-8, IL-10, IL-12, IL16, MIG, MIP-1α, MIP-1β, KC, MCP-1, TNF-α, GM-CSI, VEGF, and the like. Anti-inflammatory cytokines that may demonstrate an altered expression profile may include, without limitation, IL-1ra, IL-4, IL-10, IL-13, and the like. Cytokines associated with foreign body response that may demonstrate an altered expression profile may include, without limitation, IL-4, IL-10, IL-13, and so forth.

The device may be formed according to a single-step process, i.e., the surface is formed with the nanostructures on the surface at the time of formation. Alternatively, a multi-step process may be used, in which a pattern of nanostructures are fabricated on a pre-formed surface. For example, an array of microneedles may be first formed and then a random or non-random pattern of nanostructures may be fabricated on the surface of the formed microneedles. In either the single-step or two-step process, the nano-sized structures may be fabricated on the microneedle surface or on a mold surface according to any suitable nanotopography fabrication method including, without limitation, nanoimprinting, injection molding, lithography, embossing molding, and so forth.

In one embodiment, the nanostructures may be fabricated on the surface of a microneedle. In general, a microneedle may be formed according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

An electrochemical etching process may be utilized in which electrochemical etching of solid silicon to porous silicon is used to create extremely fine (on the order of 0.01 μm) silicon networks that may be used as piercing structures, i.e., microneedles. This method may use electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure may be achieved. The material not etched (i.e. the silicon remaining) forms the microneedles.

Plasma etching may also be utilized, in which deep plasma etching of silicon is carried out to create microneedles with diameters on the order of 0.1 micrometer or larger. Needles may be fabricated indirectly by controlling the voltage (as in electrochemical etching).

Lithography techniques, including photolithography, e-beam lithography, X-ray lithography, and so forth may be utilized for primary pattern definition and formation of a master die. Replication may then be carried out to form the device including a nanotopography thereon. Common replication methods include, without limitation, solvent-assisted micromolding and casting, embossing molding, injection molding, and so forth. Self-assembly technologies including phase-separated block copolymer, polymer demixing and colloidal lithography techniques may also be utilized in forming a nanotopography on a surface.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer de-mixing techniques.

Structure diameter, shape, and pitch may be controlled via selection of appropriate materials and methods. For example, etching of metals initially evaporated onto colloidal-patterned substrates followed by colloidal lift-off generally results in prism-shaped pillars. An etching process may then be utilized to complete the structures as desired. Ordered non-spherical polymeric nanostructures may also be fabricated via temperature-controlled sintering techniques, which form a variety of ordered trigonal nanometric features in colloidal interstices following selective dissolution of polymeric nanoparticles. These and other suitable formation processes are generally known in the art (see, e.g., Wood, J R Soc Interface, 2007 Feb. 22; 4(12): 1-17, incorporated herein by reference).

Figure 11A:
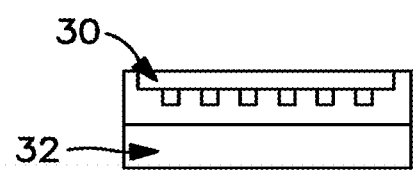
FIGS. 11A-11C schematically illustrate a nanoimprinting method as may be utilized in one embodiment in forming a device.
Figure 11B:
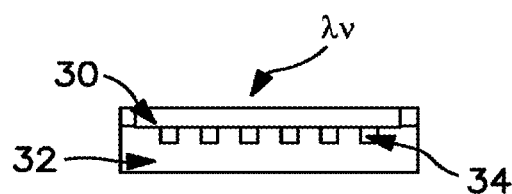
Figure 11C:
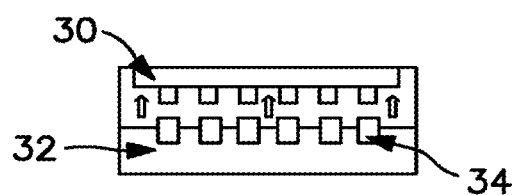

Other methods as may be utilized in forming the device including a fabricated nanotopography on a surface include nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 11A-11C. During fabrication, a hybrid mold 30 imprints into a substrate 32 via applied pressure to form features on a resist layer (FIG. 11A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 11B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below $T_g$ of the substrate and polymer (FIG. 11C).

To facilitate the release of the nanoimprinted substrate 32 including fabricated features 34 from the mold 30, as depicted in FIG. 11C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane ($F_{13}$-TCS).

A nanoimprinting process is a dynamic one which includes filling a mold followed by detachment of a formed polymer from the mold. To fill the mold features, the polymer temperature must be raised to a level high enough to initiate flow under the applied pressure. The higher the temperature, the lower the polymer viscosity, and the faster and easier the mold will fill. A higher pressure will also improve the fill rate and overall fill for better mold replication. To release the nanoimprinted substrate from the mold, the substrate temperature may be lowered to a point where the yield strength exceeds the adhesional forces exerted by the mold. By varying the temperature it is also possible to draw the polymer features during detachment to obtain different structures, for instance structures as illustrated in FIG. 9.

Structures may also be formed according to chemical addition processes. For instance, film deposition, sputtering, chemical vapor deposition (CVD), epitaxy (vapor phase, liquid phase, and molecular beam), electroplating, and so forth may be utilized for building structures on a surface.

Self-assembled monolayer processes as are known in the art may be utilized to form a pattern of structures on a surface. For instance, the ability of block copolymers to self-organize may be used to form a monolayer pattern on a surface. The pattern may then be used as a template for the growth of desired structures, e.g., colloids, according to the pattern of the monolayer.

By way of example, a two-dimensional, cross-linked polymer network may be produced from monomers with two or more reactive sites. Such cross-linked monolayers have been made using self-assembling monolayer (SAM) (e.g., a gold/alkyl thiol system) or Langmuir-Blodgett (LB) monolayer techniques (Ahmed et al., Thin Solid Films 187: 141-153 (1990)) as are known in the art. The monolayer may be crosslinked, which may lead to formation of a more structurally robust monolayer.

The monomers used to form a patterned monolayer may incorporate all the structural moieties necessary to affect the desired polymerization technique and/or monolayer formation technique, as well as to influence such properties as overall solubility, dissociation methods, and lithographic methods. A monomer may contain at least one and more often at least two, reactive functional groups.

A molecule used to form an organic monolayer may include any of various organic functional groups interspersed with chains of methylene groups. For instance a molecule may be a long chain carbon structure containing methylene chains to facilitate packing. The packing between methylene groups may allow weak Van der Waals bonding to occur, enhancing the stability of the monolayer produced and counteracting the entropic penalties associated with forming an ordered phase. In addition, different terminal moieties, such as hydrogen-bonding moieties may be present at one terminus of the molecules, in order to allow growth of structures on the formed monolayer, in which case the polymerizable chemical moieties may be placed in the middle of the chain or at the opposite terminus. Any suitable molecular recognition chemistry may be used in forming the assembly. For instance, structures may be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule may be utilized to form the template. This additional molecule may have appropriate functionality at one of its termini in order to form a SAM. For example, on a gold surface, a terminal thiol may be included. There are a wide variety of organic molecules that may be employed to effect replication. Topochemically polymerizable moieties, such as dienes and diacetylenes, are particularly desirable as the polymerizing components. These may be interspersed with variable lengths of methylene linkers.

For an LB monolayer, only one monomer molecule is needed because the molecular recognition moiety may also serve as the polar functional group for LB formation purposes. Lithography may be carried out on a LB monolayer transferred to a substrate, or directly in the trough. For example, an LB monolayer of diacetylene monomers may be patterned by UV exposure through a mask or by electron beam patterning.

Monolayer formation may be facilitated by utilizing molecules that undergo a topochemical polymerization in the monolayer phase. By exposing the assembling film to a polymerization catalyst, the film may be grown in situ, and changed from a dynamic molecular assembly to a more robust polymerized assembly.

Any of the techniques known in the art for monolayer patterning may be used for patterning of the monolayer. Techniques useful in patterning a monolayer include, but are not limited to, photolithography, e-beam techniques, focused ion-beam techniques, and soft lithography. Various protection schemes such as photoresist may be used for a SAM-based system. Likewise, block copolymer patterns may be formed on gold and selectively etched to form patterns. For a two-component system, patterning may also be achieved with readily available techniques.

Soft lithography techniques may be utilized to pattern the monolayer in which ultraviolet light and a mask may be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer may be achieved by various growth mechanisms, such as through appropriate reduction chemistry of a metal salts and the use of seed or template-mediated nucleation. Using the recognition elements on the monolayer, inorganic growth may be catalyzed at this interface by a variety of methods. For instance inorganic compounds in the form of colloids bearing the shape of the patterned organic monolayer may be formed. For instance calcium carbonate or silica structures may be templated by various carbonyl functionalities such as carboxylic acids and amides. By controlling the crystal growth conditions, it is possible to control the thickness and crystal morphology of the mineral growth. Titanium dioxide may also be templated.

Templated electroless plating techniques may be used to synthesize metals using existing organic functional groups. In particular, by chelating metal atoms to the carbonyl moieties of the organic pattern, electroless metal deposition may be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art may be utilized, for example a method as described in U.S. Pat. No. 7,189,435 Tuominen, et al., which is incorporated herein by reference, may be utilized. According to this method, a conducting or semiconducting substrate (for example, a metal, such as gold) may be coated with a block copolymer film (for example, a block copolymer of methylmethacrylate and styrene), where one component of the copolymer forms nanoscopic cylinders in a matrix of another component of the copolymer. A conducting layer may then be placed on top of the copolymer to form a composite structure. Upon vertically orientation of the composite structure, some of the first component may be removed, for instance by exposure to UV radiation, an electron beam, or ozone, degradation, or the like to form nanoscopic pores in that region of the second component.

In another embodiment, described in U.S. Pat. No. 6,926,953 to Nealey, et al., incorporated herein by reference, copolymer structures may be formed by exposing a substrate with an imaging layer thereon, for instance an alkylsiloxane or an octadecyltrichlorosilane self-assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) may then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nanometers or less.

The device surface may include a random distribution of fabricated nanostructures. Optionally, the surface may include additional materials, in conjunction with the fabricated nanostructures. For example, a transdermal patch surface may have fabricated thereon an electrospun fibrous layer, and a random or non-random pattern of structures may be fabricated on this electrospun layer.

Electrospinning includes of the use of a high voltage supplier to apply an electrical field to a polymer melt or solution held in a capillary tube, inducing a charge on the individual polymer molecules. Upon application of the electric field, a charge and/or dipolar orientation will be induced at the air-surface interface. The induction causes a force that opposes the surface tension. At critical field strength, the electrostatic forces will overcome surface tension forces, and a jet of polymer material will be ejected from the capillary tube toward a conductive, grounded surface. The jet is elongated and accelerated by the external electric field as it leaves the capillary tube. As the jet travels in air, some of the solvent may evaporate, leaving behind charged polymer fibers which may be collected on the surface. As the fibers are collected, the individual and still wet fibers may adhere to one another, forming a nonwoven web on the surface. A pattern of nanostructures may then be fabricated on the electrospun surface, for instance through an embossing technique utilizing a mold defining the desired nanostructures. Applying the mold to the microneedle surface at suitable temperature and pressure may transfer the pattern to the microneedle surface. A surface of random electrospun nano-sized fibers may further improve the desirable characteristics of a microneedle surface, e.g., one or more of surface area to volume ratio, surface roughness, surface energy, and so forth, and may provide associated benefits.

The surface of the device may be further functionalized for improved interaction with tissues or individual cells during use. For instance, one or more biomolecules such as polynucleotides, polypeptides, entire proteins, polysaccharides, and the like may be bound to a structured surface prior to use.

In some embodiments, a surface including structures formed thereon may already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a patterned device may include ECM proteins such as laminins, tropoelastin or elastin, Tropocollagen or collagen, fibronectin, and the like. Short polypeptide fragments may be bound to the surface of a patterned device such as an RGD sequence, which is part of the recognition sequence of integrin binding to many ECM proteins. Thus, functionalization of a microneedle surface with RGD may encourage interaction of the device with ECM proteins and further limit foreign body response to the device during use.

Devices may be associated with an agent for delivery via the device. For instance, a transdermal patch may be utilized to increase permeability of the epithelial layer and for delivery of materials beneath the stratum corneum to the stratum spinosum or the stratum germ inativum, or even deeper into the dermis. In one embodiment, an agent may be transported across the stratum corneum in conjunction with a microneedle, e.g., within the microneedle or at the surface of the microneedle.

The transdermal patch may include a reservoir, e.g., a vessel, a porous matrix, etc., that may store an agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

Figure 12A:
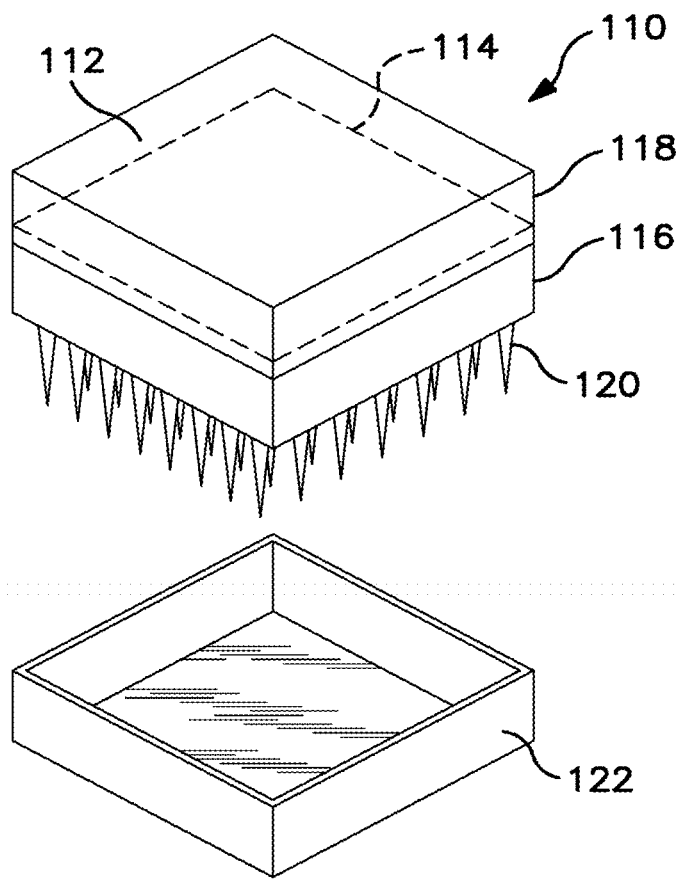
FIGS. 12A-12B schematically illustrate one embodiment of a device.
Figure 12B:
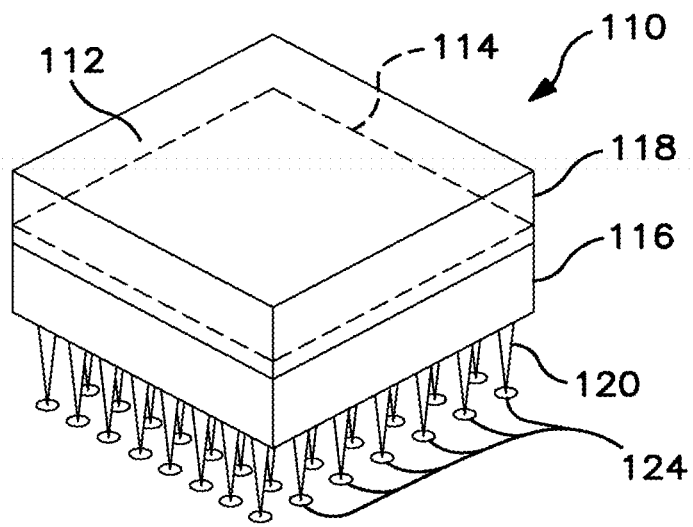

FIGS. 12A and 12B are perspective views of a device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120 including nanostructures formed on a surface 124. A release liner 122 may be removed prior to use of the device to expose microneedles 120.

A formulation including one or more agents may be retained within the reservoir 112. Materials suitable for use as impermeable backing layer 114 may include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 14 and the microneedle array 116, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the substrate upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single agent formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

Figure 13:
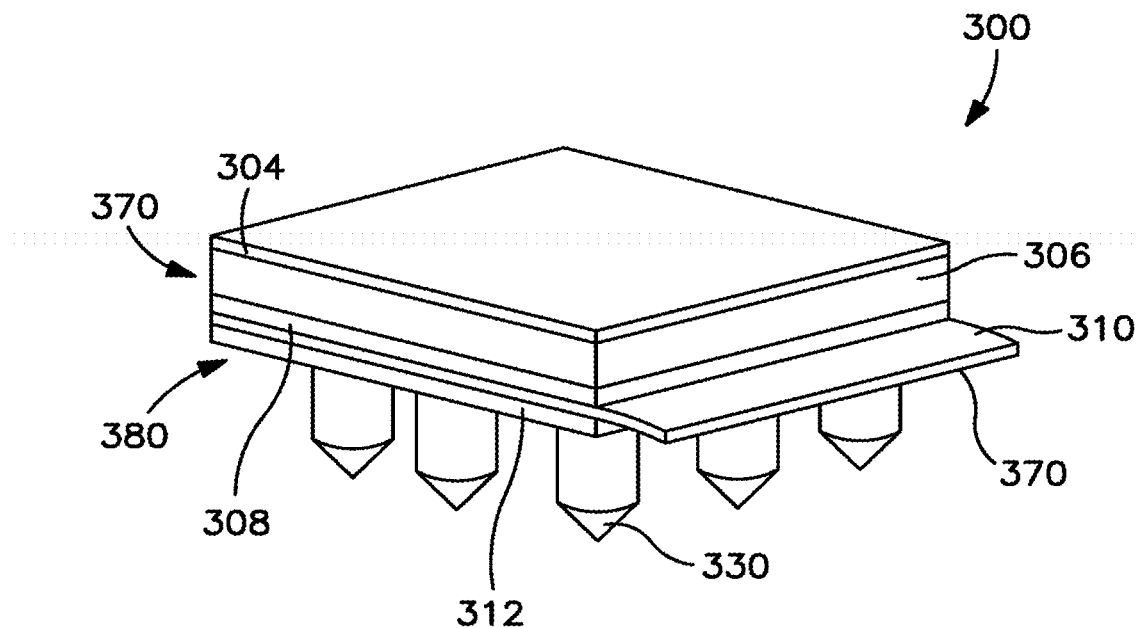
FIG. 13 is a perspective view of one embodiment of a transdermal patch prior to delivery of a drug compound.
Figure 14:
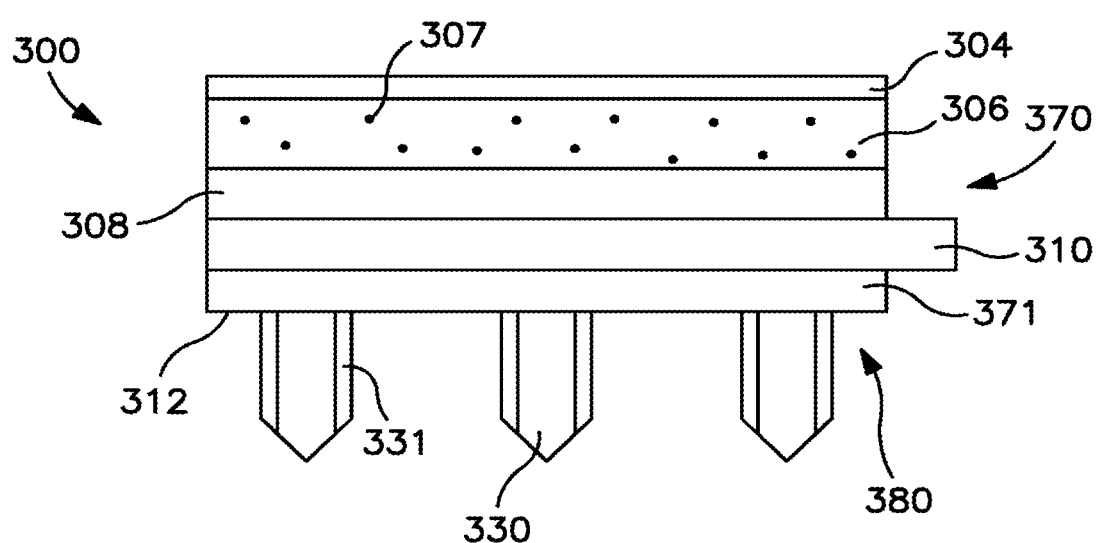
FIG. 14 is a front view of the patch of FIG. 13.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 13-18, one embodiment of a release member is shown that is configured to be detached from a transdermal patch to initiate the flow of a drug compound. More particularly, FIGS. 13-14 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 13-14, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 13-14) that extends at least partly beyond the perimeter of the patch 300 to facilitate the ability of a user to grab onto the member and pull it in the desired direction. In its "inactive" configuration as shown in FIGS. 13-14, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 15:
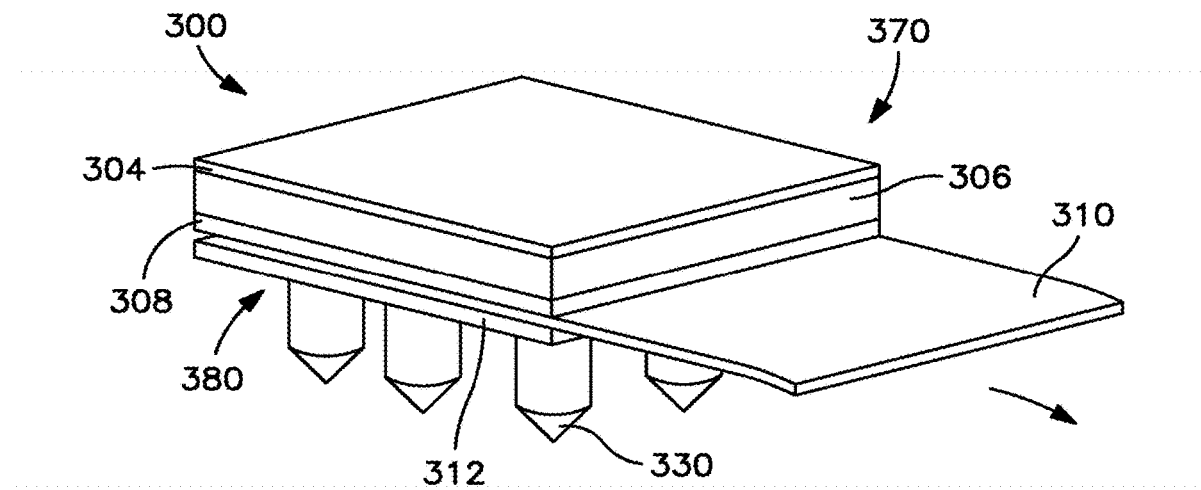
FIG. 15 is a perspective view of the patch of FIG. 13 in which the release member is partially withdrawn from the patch.
Figure 16:
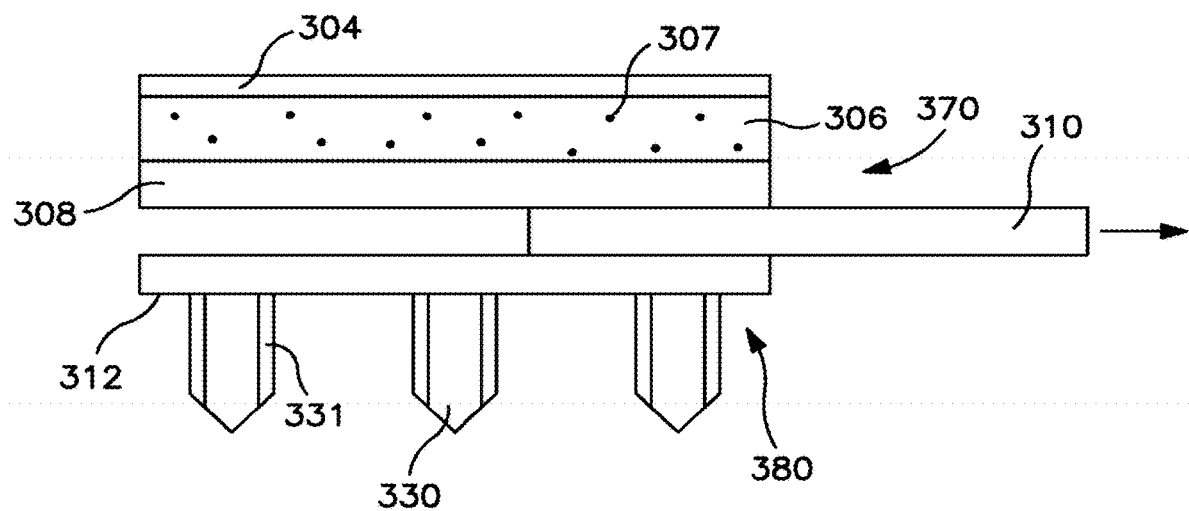
FIG. 16 is a front view of the patch of FIG. 13.
Figure 17:
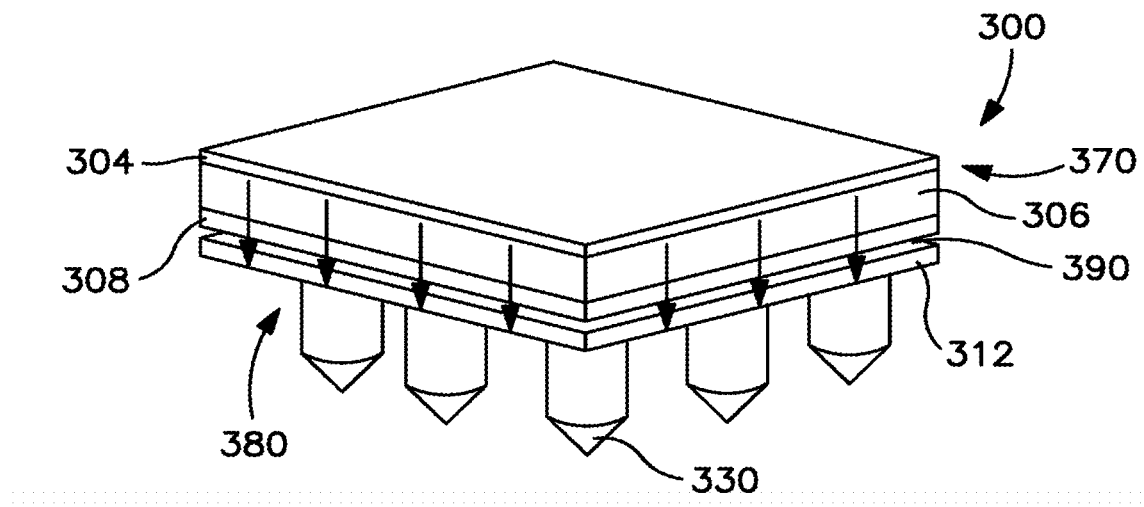
FIG. 17 is a perspective view of the transdermal patch of FIG. 13 after removal of the release member and during use.
Figure 18:
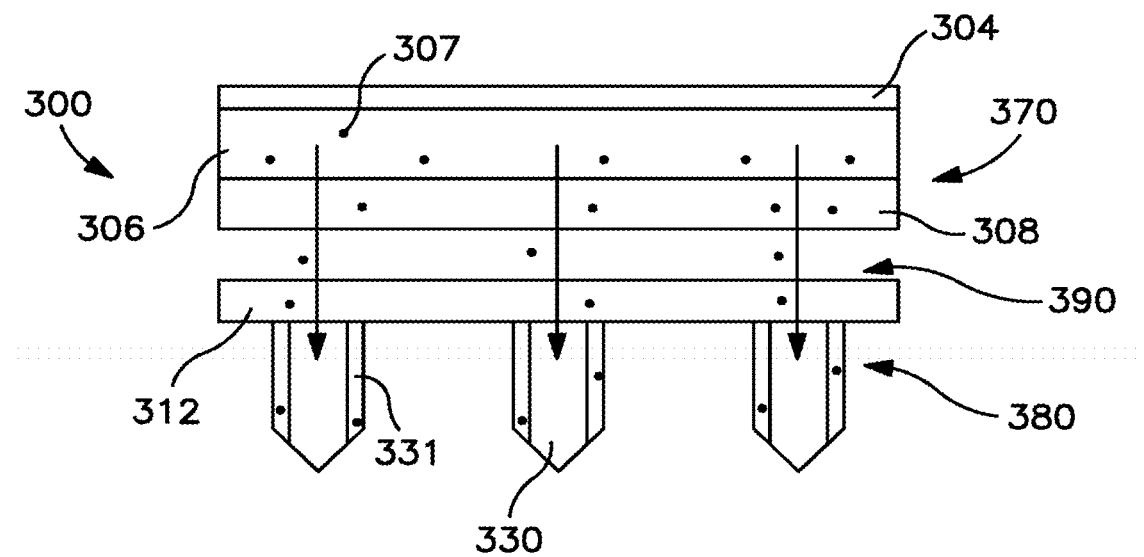
FIG. 18 is a front view of the patch of FIG. 17.

Referring to FIGS. 15-16, one embodiment for activating the patch 300 is shown in which the release member 310 is pulled in a longitudinal direction. The entire release member 310 may be removed as shown in FIGS. 17-18, or it may simply be partially detached as shown in FIGS. 15-16. In either case, however, the seal previously formed between the release member 310 and the aperture (not shown) of the support 312 is broken. In this manner, a drug compound 307 may begin to flow from the drug delivery assembly 370 and into the channels 331 of the microneedles 330 via the support 312. An exemplary illustration of how the drug compound 307 flows from the reservoir 306 and into the channels 331 is shown in FIGS. 17-18. Notably, the flow of the drug compound 307 is passively initiated and does not require any active displacement mechanisms (e.g., pumps).

In the embodiments shown in FIGS. 13-18, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 19:
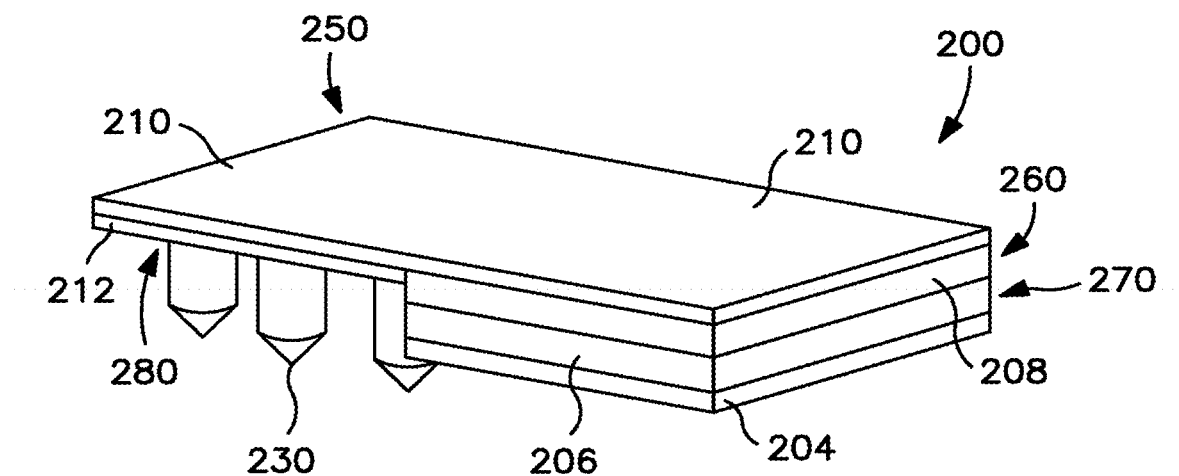
FIG. 19 is a perspective view of another embodiment of a transdermal patch prior to delivery of a drug compound.
Figure 20:
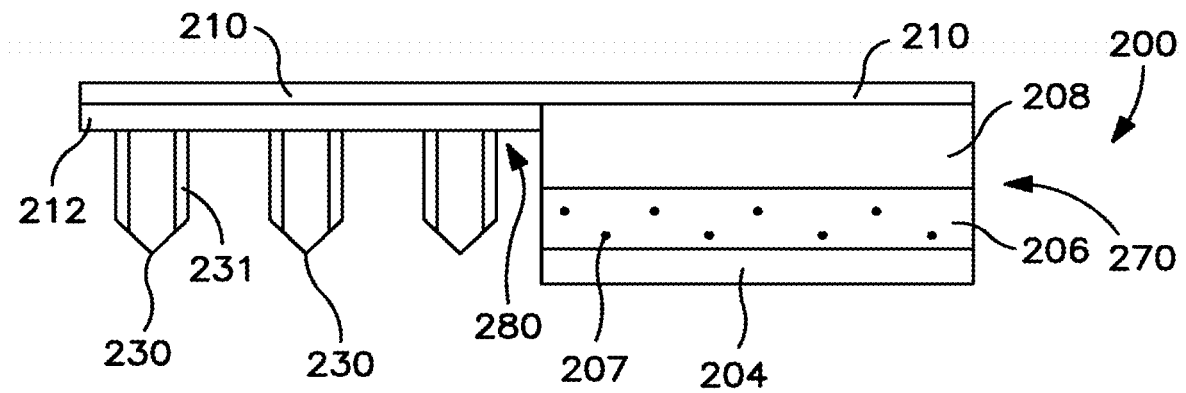
FIG. 20 is a front view of the patch of FIG. 19.

Referring to FIGS. 19-24, for example, one particular embodiment of a patch 200 is shown. FIGS. 19-20 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 21:
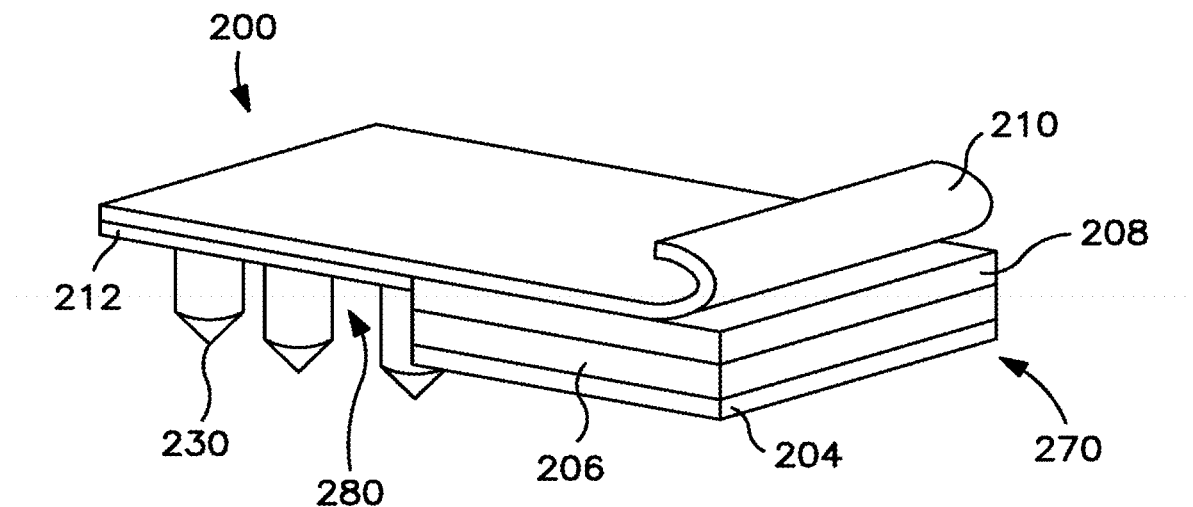
FIG. 21 is a perspective view of the patch of FIG. 19 in which the release member is partially peeled away from the patch.
Figure 22:
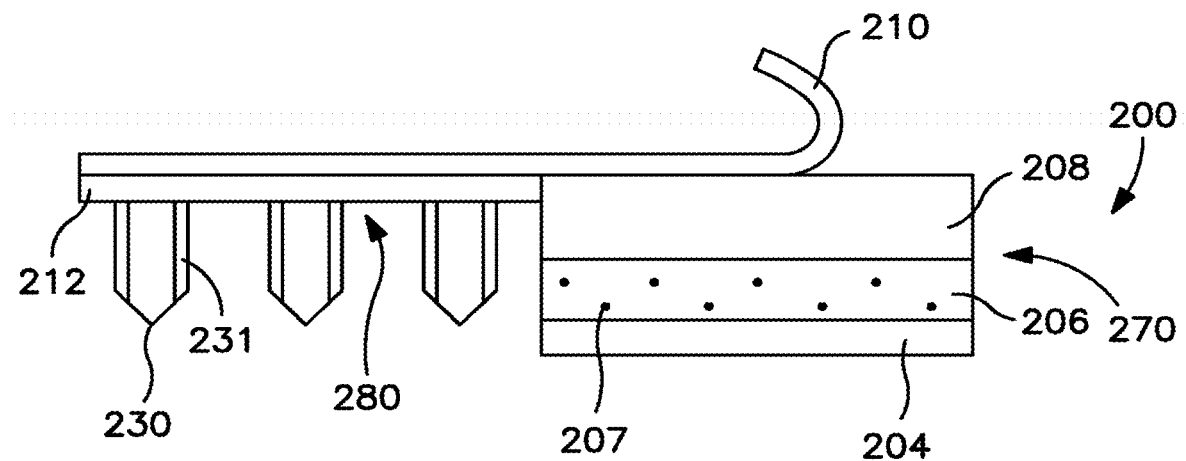
FIG. 22 is a front view of the patch of FIG. 21.
Figure 23:
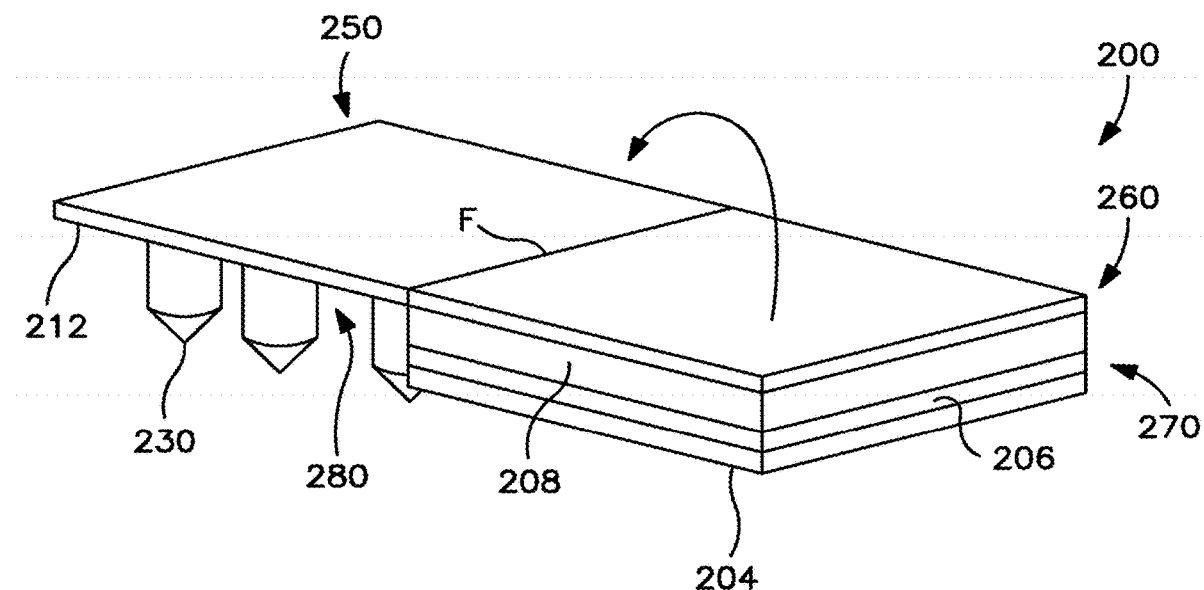
FIG. 23 is a perspective view of the patch of FIG. 19 in which the release member is completely peeled away from the patch.
Figure 24:
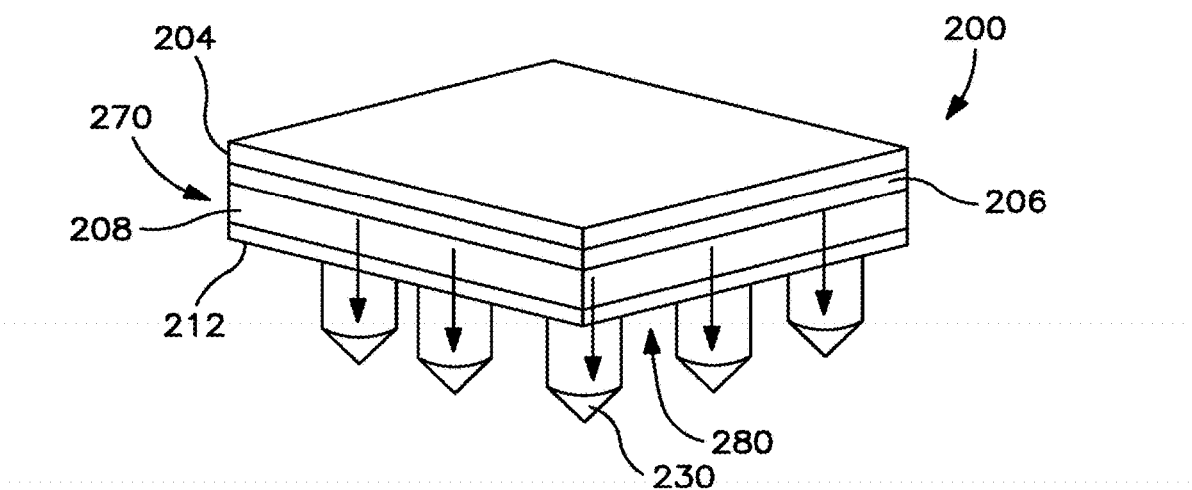
FIG. 24 is a perspective view of the transdermal patch of FIG. 19 after removal of the release member and during use.
Figure 27A:
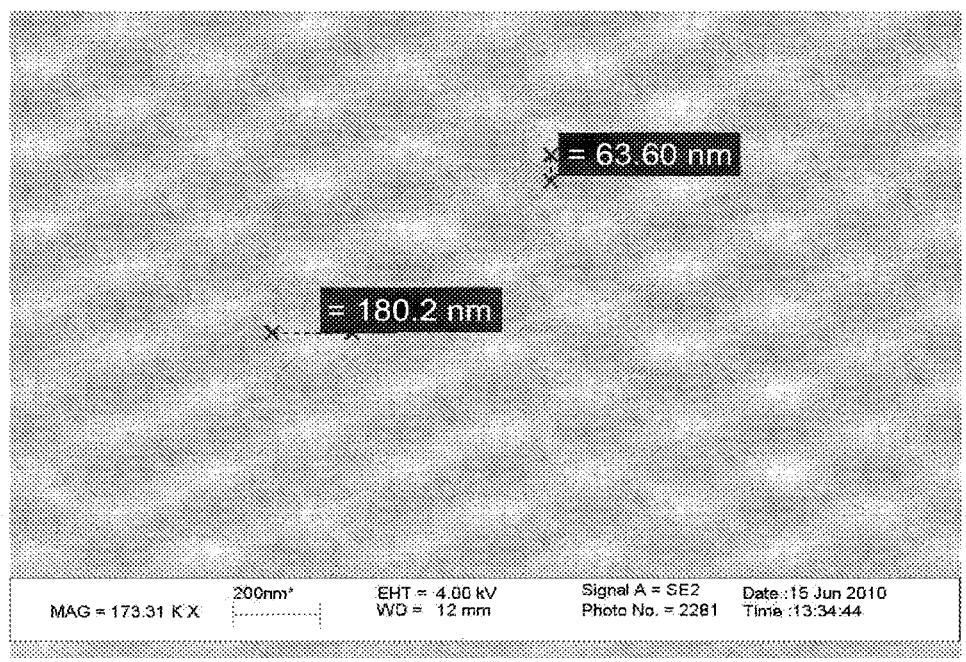
FIGS. 27A and 27B are two SEM of a film including another nanopatterned surface.
Figure 27B:
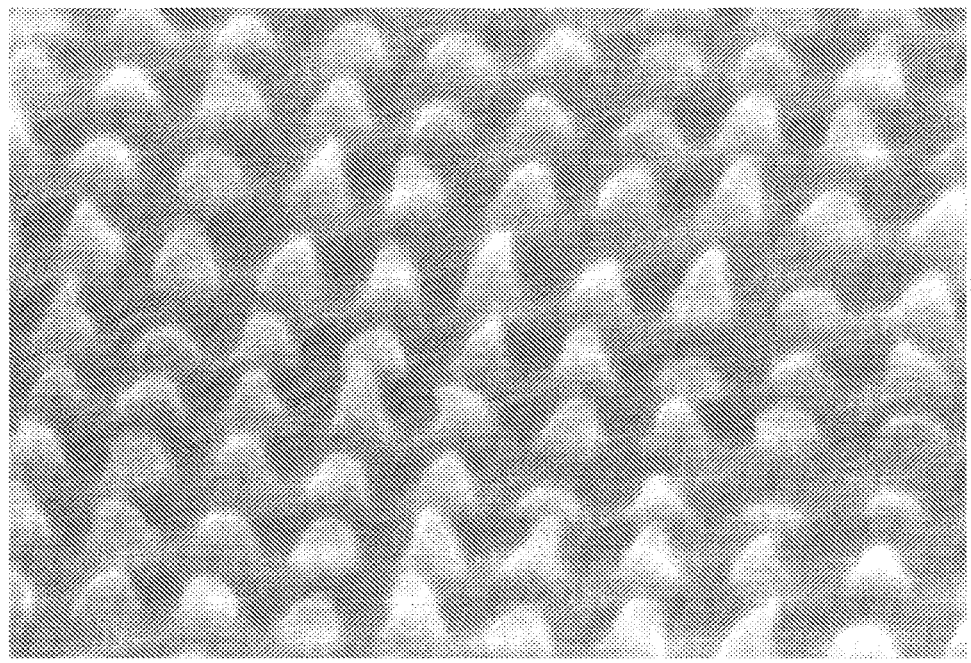
Figure 28:
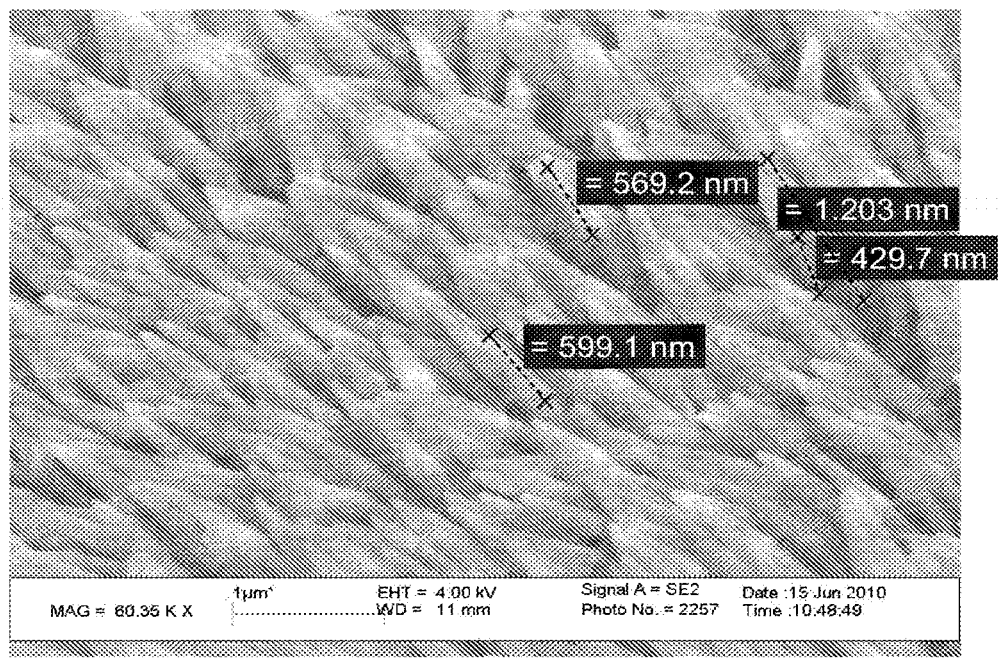
FIG. 28 is an SEM of a film including another nanopatterned surface.
Figure 29:
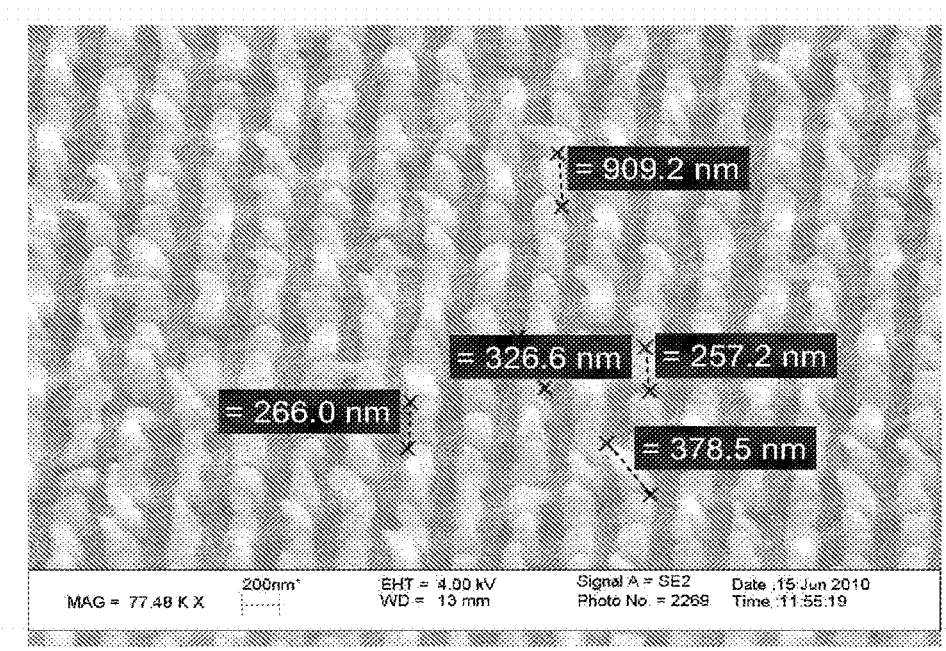
FIG. 29 is an SEM of a film including another nanopatterned surface.
Figure 30:
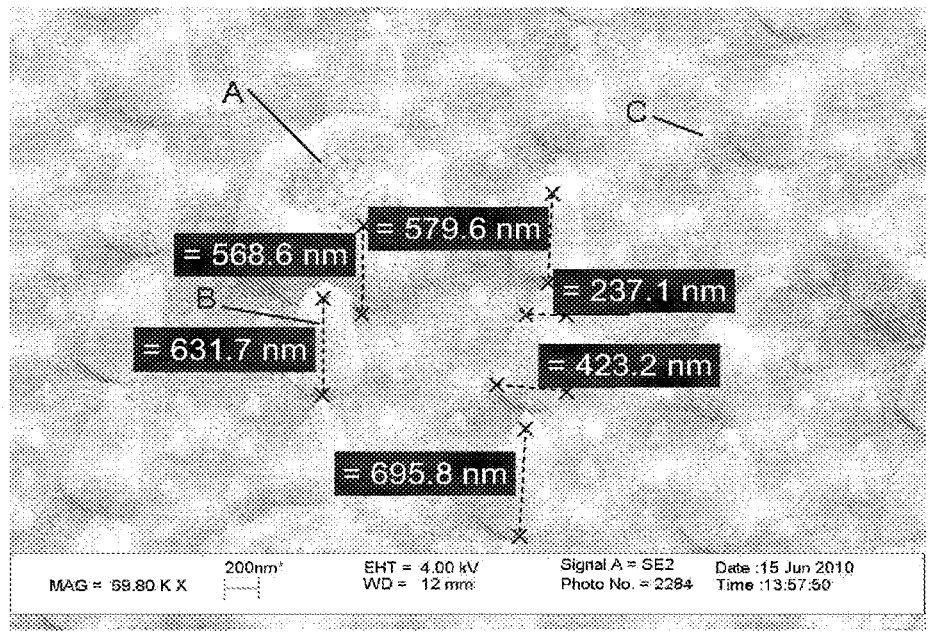
FIG. 30 is an SEM of a film including another nanopatterned surface.
Figure 31:
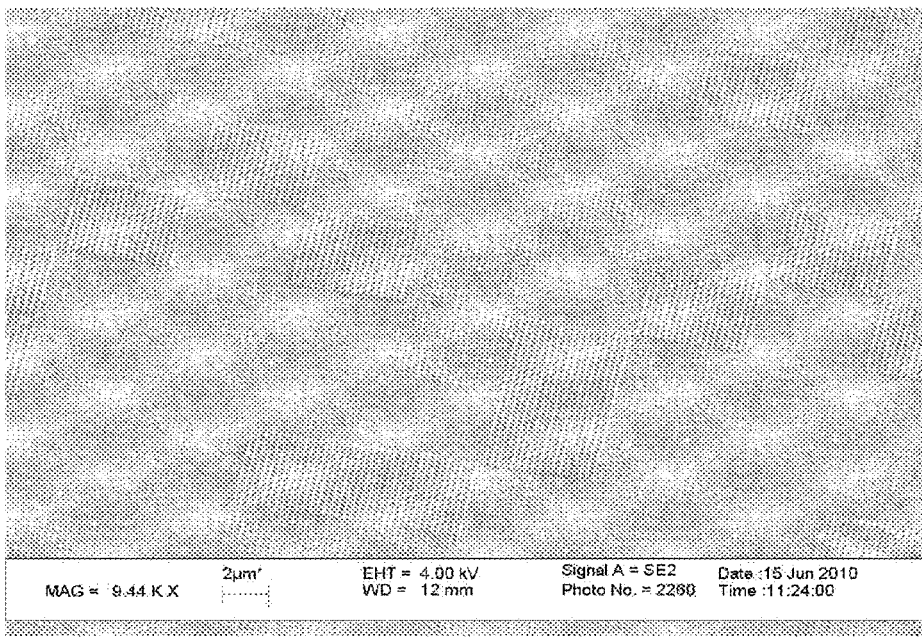
FIG. 31 is an SEM of a film including another nanopatterned surface.
Figure 32:
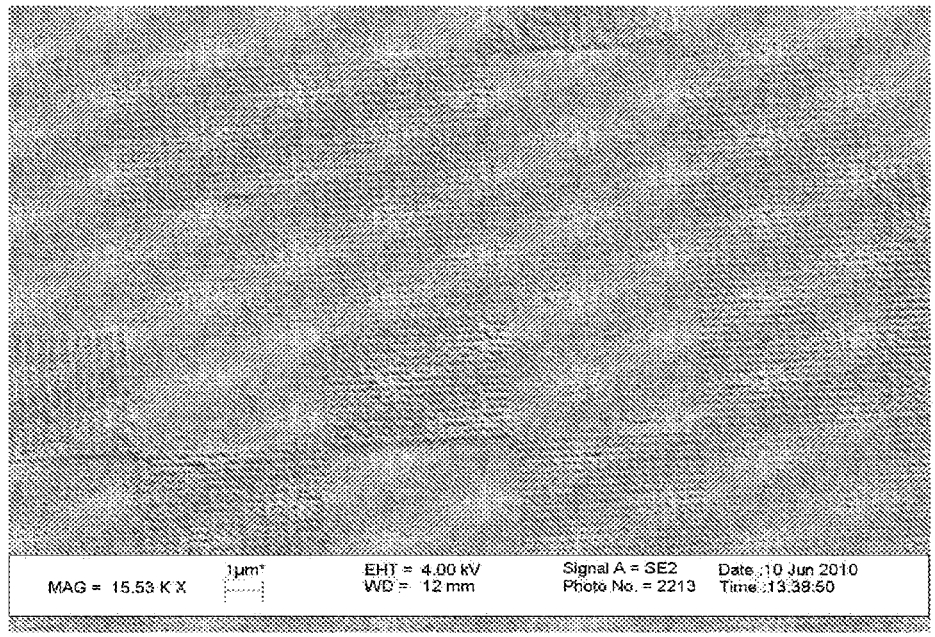
FIG. 32 is an SEM of a film including another nanopatterned surface.
Figure 33:
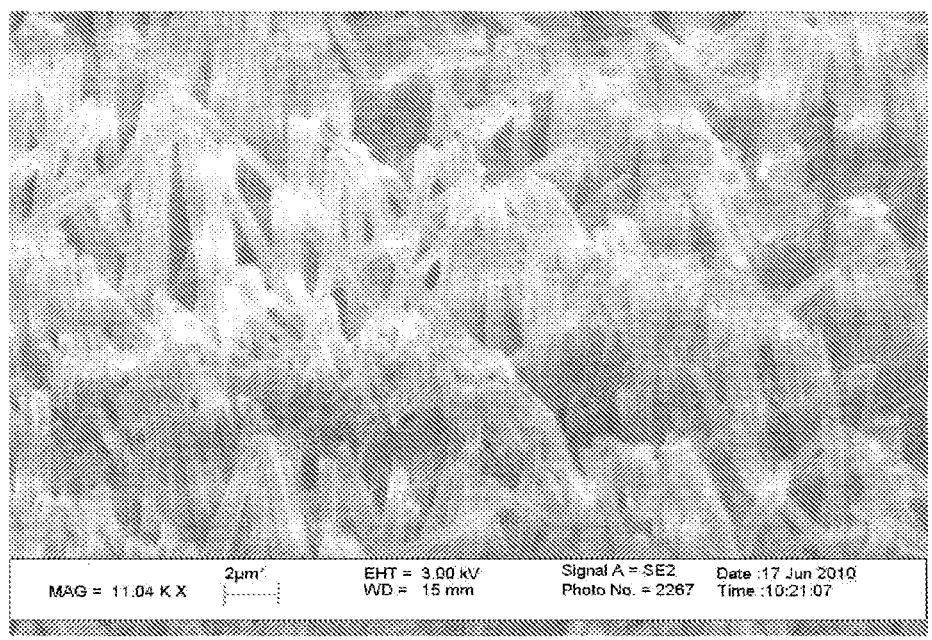
FIG. 33 is an SEM of a film including another nanopatterned surface.
Figure 34:
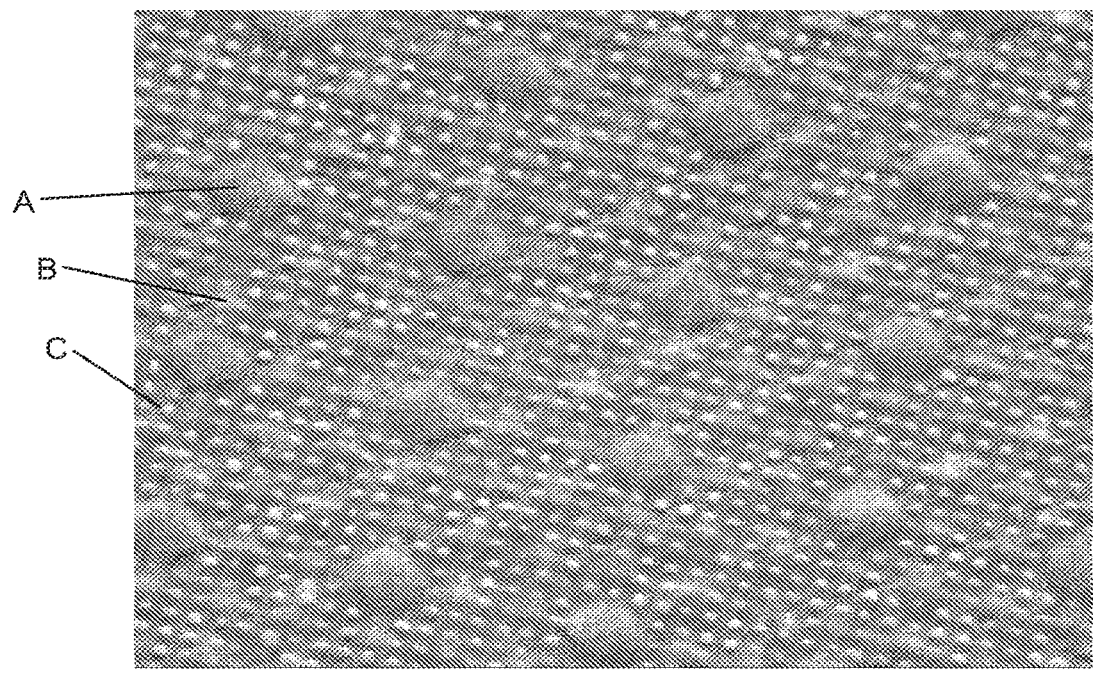
FIG. 34 is an SEM of a film including another nanopatterned surface.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 19-20, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 21-22, to break the seal previously formed between the release member 210 and the aperture (not shown) of the support 212. Thereafter, the second section 260 may be folded about a fold line "F" as shown by the directional arrow in FIG. 23 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 24).

The device may deliver an agent at a rate so as to be therapeutically useful. In accord with this goal, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a patch surface, a microneedle, and/or a substrate adjacent a microneedle, to create a convective flow which carries oppositely charged ionic species and/or neutral molecules toward or into the delivery site.

Flow of an agent may be manipulated by selection of the material forming the device surface. For example, one or more large grooves adjacent the tissue contacting surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

Agents as may be delivered by the device may be intended for the local area near the device or may be intended for wider distribution.

The nanotopography of the device may improve delivery of agents while minimizing foreign body and immune response.

As discussed, the device may increase permeability of a cellular layer, which may provide a route for delivery of compounds previously prevented from transdermal delivery such as protein therapeutics. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. Delivery of protein therapeutics has proven problematic in the past due to the natural barriers of the skin. In one embodiment, the device may be utilized in transdermal delivery of high molecular weight agents (e.g., agents defining a molecular weight greater than about 400 Da, greater than about 10 kDa, greater than about 20 kDa, or greater than about 100 kDa, e.g., about 150 kDa).

Even when considering delivery of small molecular weight agents, the device may provide increased efficiency and improved uptake due to increased permeability of the epithelial tissue.

There is no particular limitation to agents as may be delivered by use of the device. Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs regulating cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally Injecting Substances", the entire content of which is incorporated herein by reference. Vaccine formulations may include an antigen or antigenic composition capable of eliciting an immune response against a human pathogen or from other viral pathogens.

The present disclosure may be further understood with reference to the Examples provided below.

Example 1

Several different molds were prepared using photolithography techniques similar to those employed in the design and manufacture of electrical circuits. Individual process steps are generally known in the art and have been described.

Initially, silicon substrates were prepared by cleaning with acetone, methanol, and isopropyl alcohol, and then coated with a 258 nanometer layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 μC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm) He, 22 sccm $CF_4$, 20 sccm $C_4F_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm $Cl_2$ and 5 sccm Ar at 5 mTorr, 600 W coil, 50 W ME and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 W/cm$^2$. A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Several different nanotopography patterns were formed, schematic representations of which are illustrated in FIGS. 25A-25D. The nanotopography pattern illustrated in FIG. 25E was a surface of a flat substrate purchased from NTT Advanced Technology of Tokyo, Japan. The patterns were designated DN1 (FIG. 25A), DN2 (FIG. 25B), DN3 (FIG. 25C), DN4 (FIG. 25D) and NTTAT2 (FIG. 25E). SEM images of the molds are shown in FIGS. 25A, 25B, and 25C, and images of the films are shown in FIGS. 25D and 25E. FIG. 9 illustrates a nanopatterned film formed by use of the mold of FIG. 25A (DN1). In this particular film, the polymer features were drawn by temperature variation as previously discussed. The surface roughness of the pattern of FIG. 25E was found to be 34 nanometers.

The pattern illustrated in FIGS. 8C and 8D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described above in Example 1 including various different patterns and formed of either polystyrene (PS) or polypropylene (PP). The underlying substrate varied in thickness. Patterns utilized were either DN2, DN3, or DN4 utilizing formation processes as described in Example 1. The pattern molds were varied with regard to hole depth and feature spacing to form a variety of differently-sized features having the designated patterns. Sample no. 8 (designated BB 1) was formed by use of a 0.6 μm millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are illustrated in FIGS. 26-34 and characteristics of the formed films are summarized in Table 3, below.

For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from μMasch. The cantilever had a resonant frequency of 170 kHz, a spring constant of 40 N/m, a length of 230±5 μm, a width of 40±3 μm, and a thickness of 7.0±0.5 μm. The probe tip was an n-type phosphorous-doped silicon probe, with a typical probe tip radius of 10 nanometers, a full tip cone angle of 40°, a total tip height of 20-25 μm, and a bulk resistivity 0.01-0.05 ohm-cm.

The surface roughness value given in Table 3 is the arithmetical mean height of the surface areal roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

The fractal dimension may also be evaluated from 2D Fourier spectra by application of the Log Log function. If the surface is fractal the Log Log graph should be highly linear, with a negative slope (see, e.g., Fractal Surfaces, John C. Russ, Springer-Verlag New York, LLC, July, 2008).

Example 3

HaCaT human skin epithelial cells were grown in DMEM, 10% FBS, 1% penicillin/streptomycin at 37° C., 5% $CO_2$ for 24 hours at a concentration of 25,000 cell/$cm^2$ in 6 well plates. Plates either had polypropylene nanopatterned films formed as described above in Example 1 and designate DN1, DN2 (Sample 4 of Table 3), DN3 or untreated surface at the bottom of the well. Nanopatterned films were adhered in place with cyanoacrylate.

Cells were detached from the surfaces with 1 mL of trypsin per well for 10 minutes, quenched with 1 mL growth medium (same as above), then transferred to a microfuge tube and pelleted at 1200 rpm for 7 minutes.

RNA was isolated from pelleted cells using the RNeasy miniprep kit from Qiagen using the manufacturer's protocol. Briefly, cells were lysed, mixed with ethanol and spun down

TABLE 3

| Sample No. | FIG. | Pattern | Material | Film thickness (μm) | Pattern Feature[1] | Cross Section Dimension[2] | Feature height[3] | Aspect Ratio | Surface Roughness (nm) | Fractal Dimension | Water Contact Angle |
|---|---|---|---|---|---|---|---|---|---|---|---|
| 1 | 26 | DN3 | PS | 75 | A | 1100 nm | 520 nm | 0.47 | 150 | 2.0 | 100° |
|   |   |   |   |   | B | 400 nm | 560 nm | 1.4 |   |   |   |
|   |   |   |   |   | C | 200 nm | 680 nm | 3.4 |   |   |   |
| 2 | 27A, 27B | DN2 | PP | 5.0 | n/a | 200 nm | 100 nm | 0.5 | 16 | 2.15 | 91° |
| 3 | 28 | DN2 | PS | 75 | n/a | 200 nm | 1.0 μm | 5 | 64 | 2.2 | 110° |
| 4 | 29 | DN2 | PP | 25.4 | n/a | 200 nm | 300 nm | 1.5 | 38 | 1.94 | 118° |
| 5 | 30 | DN3 | PS | 75 | A | 1100 nm | 570 nm | 0.52 | 21.1 | 1.98 | 100° |
|   |   |   |   |   | B | 400 nm | 635 nm | 1.6 |   |   |   |
|   |   |   |   |   | C | 200 nm | — | — |   |   |   |
| 6 | 31 | DN4 | PS | 75 | n/a | 200 nm | — | — | 30.6 | 2.04 | 80° |
| 7 | 32 | DN4 | PP | 25.4 | n/a | 200 nm | — | — | 21.4 | 2.07 | 112° |
| 8 | 33 | BB1 | PP | 25.4 | n/a | 600 nm | 18 μm | 30 | 820 | 2.17 | 110° |
| 9 | 34 | DN3 | PP | 5 | A | 1100 nm | 165 nm | 0.15 | 50 | 2.13 | — |
|   |   |   |   |   | B | 400 nm | 80 nm | 0.2 |   |   |   |
|   |   |   |   |   | C | 200 nm | 34 nm | 0.17 |   |   |   |

[1] Pattern Features as shown on the figures.
[2] Cross sectional dimension values were derived from the mold and equated as an approximation of the maximum dimension of the structure, although it should be understood that the actual dimension of an individual structure may vary slightly as may be seen in the figures.
[3] Feature heights are provided as the average of several individually determined feature heights.

in a column. Lysates were then washed 3 times, treated with DNase and eluted in 40 μl volumes.

cDNA was created from the RNA isolated using the RT first strand kit from SA Biosciences. Briefly, RNA was treated with DNase again at 42° C. for 5 minutes. Random primers and reverse transcriptase enzyme was then added and incubated at 42° C. for 15 minutes, then incubated at 95° C. for 5 minutes to stop reaction.

qPCR was then performed on the cDNA samples using RT profiler custom PCR array from SA Biosciences with primers for IL1-β, IL6, IL8, IL10, IL1R1, TNFα, TGFβ-1, PDGFA, GAPDH, HDGC, RTC and PPC. Briefly, cDNA was mixed with SYBR green and water, and then added to a PCR plate pre-fixed with the correct sense and antisense primer pair for the gene of interest. The plate was then run on an ABI StepOnePlus PCR machine heated to 95° C. for 10 minutes, then for 45 cycles of: 15 seconds at 95° C. and 1 minute at 60° C.

Delta delta $C_T$ analysis was performed using GAPDH as the internal control. HDGC, RTC and PPC levels were used as additional internal controls for activity and genomic DNA contamination.

One-way ANOVA and Tukey's 2-point tests were then used to determine statistical significance in the differences between surfaces.

Table 4, below, presents the protein expressions obtained as the fold change in expression on nanoimprinted structures produced on polypropylene films versus expression on an unstructured film.

TABLE 4

| Mold | IL1-β | IL6 | IL8 | IL10 | IL1R1 | TNFα | TGFβ1 | PDGFA |
|------|-------|------|------|------|-------|------|-------|-------|
| DN1 | 2.24 | 3.33 | 0.36 | 1.17 | 0.6 | 0.57 | 0.37 | 1.37 |
| DN2 | 3.18 | 3.2 | 0.46 | 0.43 | 0.36 | 0.57 | 0.42 | 1.23 |
| DN3 | 3.36 | 2.7 | 0.47 | 5.83 | 1.6 | 0.37 | 0.35 | 0.64 |

Example 4

Methods as described in Example 3 were utilized to examine the expression level for several different cytokines from HaCaT human skin epithelial cells when the cells were allowed to develop on a variety of different polypropylene (PP) or polystyrene (PS) films, formed and patterned as described above. The expression level for each cytokine was compared to that from the same cell type cultured on standard tissue culture polystyrene (TCPS) and induced with lipopolysaccharide (LPS).

Cells developed on a polypropylene film nanopatterned with a DN2 pattern, as described above (Sample 4 of Table 3), were found to upregulate expression of IL-1β, IL-1ra, IL-10, and MIP-1β downregulate expression of IL-4, IL-13, MIG, KC, IL-2, MIP-1, TNF-α, IL-12, IL-16, and IL-1a as compared to TCPS.

Several other films were examined for effect on cellular expression of different cytokines. Films were designated as follows:
 1—DN2 pattern on a 75 μm polystyrene film (Sample 3 of Table 3)
 2—DN3 pattern on a 75 μm polystyrene film (Sample 1 of Table 3)
 3—DN4 pattern on a 75 μm polystyrene film (Sample 6 of Table 3)
 4—unimprinted 75 μm polystyrene film
 5—DN2 pattern on a 25.4 μm polypropylene film (Sample 4 of Table 3)
 6—DN4 pattern on a 25.4 μm polypropylene film (Sample 7 of Table 3)
 7—DN2 pattern on a 5 μm polypropylene film (Sample 2 of Table 3)
 8—BB1 polypropylene film (Sample 8 of Table 3)
 9—unimprinted 25.4 μm polypropylene film
 10—unimprinted 5 μm polypropylene film
 - - expression level was below the testing threshold
 — expression level was lower than that for TCPS
 = expression level was similar to that for TCPS
 + expression level was above that for TCPS, but below that when induced with LPS
 ++ expression level was similar to that for induction with LPS
 +++ expression level was above that for induction with LPS

TABLE 5

| Film | 1 | 2 | 3 | 4 | 5 | 6 | 7 | 8 | 9 | 10 |
|------|---|---|---|---|---|---|---|---|---|----|
| IL-1α | -- | -- | -- | -- | -- | -- | -- | -- | -- | -- |
| IL-1β | ++ | -- | -- | ++ | -- | -- | -- | -- | -- | -- |
| IL-12 | = | = | = | = | = | = | = | = | = | = |
| TNF-α | =+ | = | = | = | = | = | = | =+ | = | = |
| MCP-1 | =+ | = | = | = | = | = | = | =+ | = | = |
| IL-2 | = | =- | =+ | = | = | = | = | = | -- | = |
| KC | -- | -- | = | = | = | = | = | = | - | - |
| MIP-1α | -- | -- | -- | +++ | -- | -- | + | -- | +++ | +++ |
| MIP-1b | ++ | + | = | = | = | + | = | - | - | = |
| MIG | = | -- | = | + | = | - | -- | - | - | = |
| GM-CSI | -- | -- | -- | -- | -- | -- | -- | -- | -- | -- |
| IL-4 | -- | -- | -- | -- | -- | -- | -- | -- | -- | -- |
| IL-13 | -- | -- | -- | ++ | -- | -- | -- | -- | -- | -- |
| IL-10 | - | - | = | = | = | = | = | = | = | = |

Example 5

HaCaT human skin epithelial cells were grown in DMEM, 10% FBS, 1% penicillin/streptomycin at 37° C., 5% $CO_2$ for 24 hours at a concentration of 25,000 cell/cm$^2$ in 6 well plates. Plates either had a polypropylene film formed as described above in Example 1 with designation DN1, DN2 (Sample 4 of Table 3), DN3 or an untreated surface at the bottom of the well. Films were adhered in place with cyanoacrylate.

Media was collected from each well and analyzed for cytokine production with a Milliplex Map Kit from Millipore. Beads to detect IL-1β, IL-1ra, IL-6, IL-8, IL-10, PDGF-AA, PGGF-AB/BB and TNF-α were used. Readings were done on a BioRad BioPlex machine. Briefly, media was placed into microplate wells with filters. Primary beads were added and incubated at room temperature for 1 hour with shaking. The plates were then washed and incubated with detection antibodies for 30 minutes at room temperature with shaking. Strepavidin-phycoertythrin was then added and incubated at room temperature for an additional 30 minutes. Plates were then washed, beads were resuspended in assay buffer and median fluorescent intensity was analyzed on the BioPlex.

Example 6

The permeability effects of films patterned as described herein were determined on a monolayer of Caco-2 cells (human epithelial colorectal adenocarcinoma cells).

Films formed as described above in Example 1 were utilized including polypropylene (PP) or polystyrene (PS) films formed with patterns designated as DN2, DN3, and DN4. A fourth film, designated as BB1 (described in Example 2, above) was also used. The protocol was run with multiple examples of each film type.

The general protocol followed for each film was as follows:

Materials

Cell culture inserts 0.4 um pore size HDPET membrane (BD Falcon)

24 well plate (BD Falcon)

Caco-2 media

Nanostructured membranes as described above

IgG-FITC (Sigma Aldrich)

BSA-FITC (Sigma Aldrich)

Minimum Essential Medium no phenol red (Invitrogen)

TEER voltmeter

Warmed PBS

Black 96-well plate

Aluminum foil

Protocol

1. Seed Caco-2 cells on collagen coated well inserts 2 weeks before permeability assay is to be performed. Collagen coated plates are made by making a 1:1 volume of 100% ethanol to collagen. Dry surfaces in sterile hood overnight until dry.

2. Make 0.1 mg/mL solution of FITC-conjugated molecule (BSA, IgG, etc) of interest in phenol red free Alpha MEM media. Wrap in aluminum foil to protect from light.

3. Check for confluency of Caco-2 cells by measuring the resistance. Resistance should be above ~600 Ohms for confluency.

4. Aspirate old media from cell culture inserts on apical and basolateral sides. Rinse with PBS to remove any residual phenol-red dye.

5. Add 0.5 mL of FITC-conjugated solution on apical side of each insert.

6. In another 24 well plate with cell culture inserts, add 0.5 mL of warmed PBS.

7. Transfer inserts to the plate with PBS. Blot the bottom of the insert on a Kim wipe to remove residual phenol red.

8. t=0—time point: sample 75 μL from the basolateral side of insert and transfer to a black-bottom 96-well plate. Replace the volume with 75 μL of warmed PBS. Record the resistance of each well using the "chopstick" electrodes.

9. Carefully add the membrane to the appropriately labeled well. Controls are the unimprinted membranes and the cells alone. Check under a microscope that the membranes make direct contact to the cells. You should be able to see a sharp circle, indicating contact with the cells.

10. t=0 time point: repeat step 7 and then place in the incubator for 1 hour.

11. t=1 time point: repeat step 7 and then place in the incubator for 1 hour.

12. t=2 time point: repeat step 7.

13. Measure fluorescence signal using a spectrofluorometer plate reader. FITC (excitation=490 nm, emission=520 nm).

Results

Films utilized and results obtained are summarized in Table 6, below.

TABLE 6

| | Sample no. (see Table 3) | | | | | | |
|---|---|---|---|---|---|---|---|
| | 2 | 3 | 4 | 5 | 6 | 7 | 8 |
| Pattern | DN2 | DN2 | DN2 | DN3 | DN4 | DN4 | BB1 |
| Material | PP | PS | PP | PS | PS | PP | PP |
| Effective Compression Modulus (MPa) | 5.3 | 16.3 | 0.29 | 10.4 | 32.3 | 4.8 | 7.8 |
| Effective Shear Modulus (MPa) | 5.32 | 58.9 | 218 | 319 | 77.8 | 4.4 | 26.7 |
| BET Surface Area (m$^2$/g) | — | 0.11 | — | 0.44 | — | 4.15 | — |
| BSA permeability increase at 120 min. (MW 66 kDa) | — | 2 | 1.9 | 3.3 | 2 | 1.4 | 1 |
| IgG permeability increase at 120 min. (MW 150 kDa) | — | 1 | — | 1 | 3.5 | — | — |

Moduli were determined according to standard methods as are known in the art as described by Schubert, et al. (Sliding induced adhesion of stiff polymer microfiber arrays: 2. Microscale behavior, Journal Royal Society, Interface, Jan. 22, 2008. 10.1098/rsif.2007.1309)

The contact angles were measured by placing a drop of water on the surface according to standard practice. (See, e.g., Woodward, First Ten Angstroms, Portsmouth, Va.).

Figure 35:
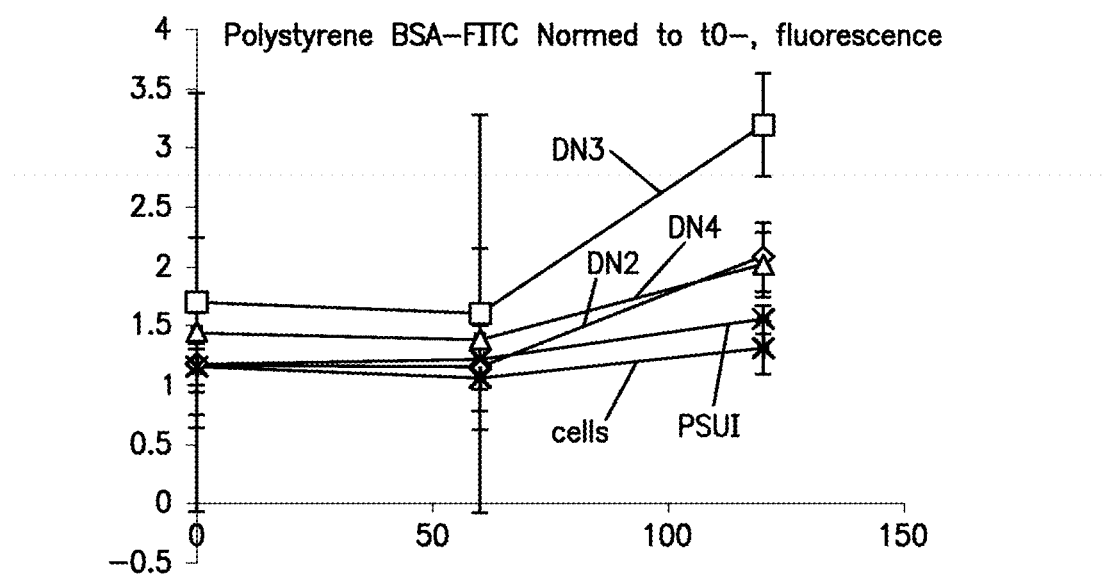
FIG. 35 graphically illustrates the effects on permeability to bovine serum albumin (BSA) in a monolayer of cells on polystyrene films patterned with nanopatterns as described herein.

FIG. 35 graphically illustrates the effects on permeability to bovine serum albumin (BSA) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned PS film (marked PSUI on FIG. 35) and a layer of cells with no adjacent film (marked 'cells' on FIG. 35). The results are illustrated as fold increase in permeability as a function of time measured in hours.

Figure 36A:
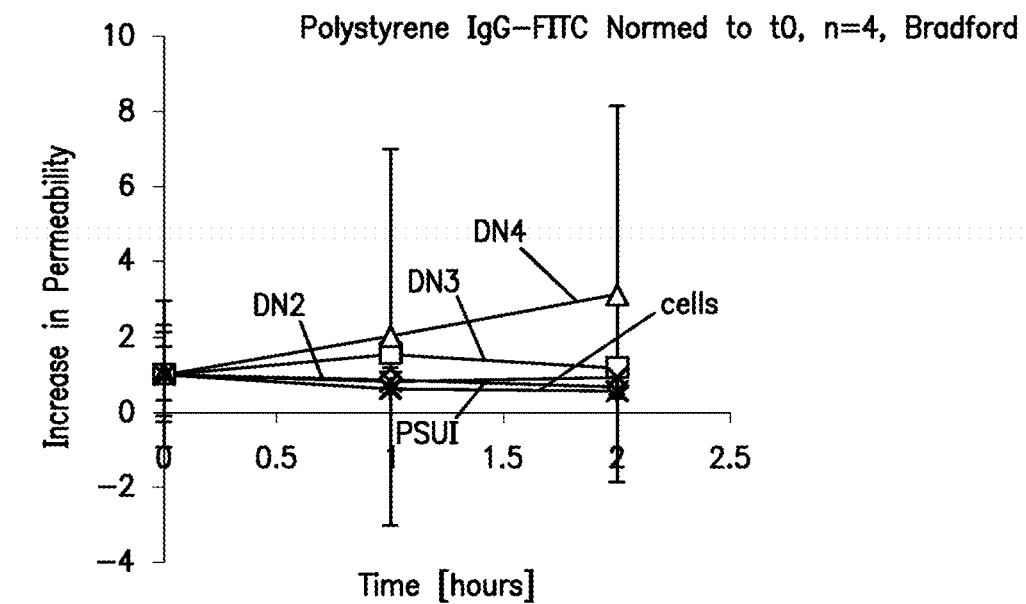
FIGS. 36A and 36B graphically illustrate the effects on permeability to immunoglobulin-G (IgG) in a monolayer of cells on polystyrene films patterned with nanopatterns as described herein.
Figure 36B:
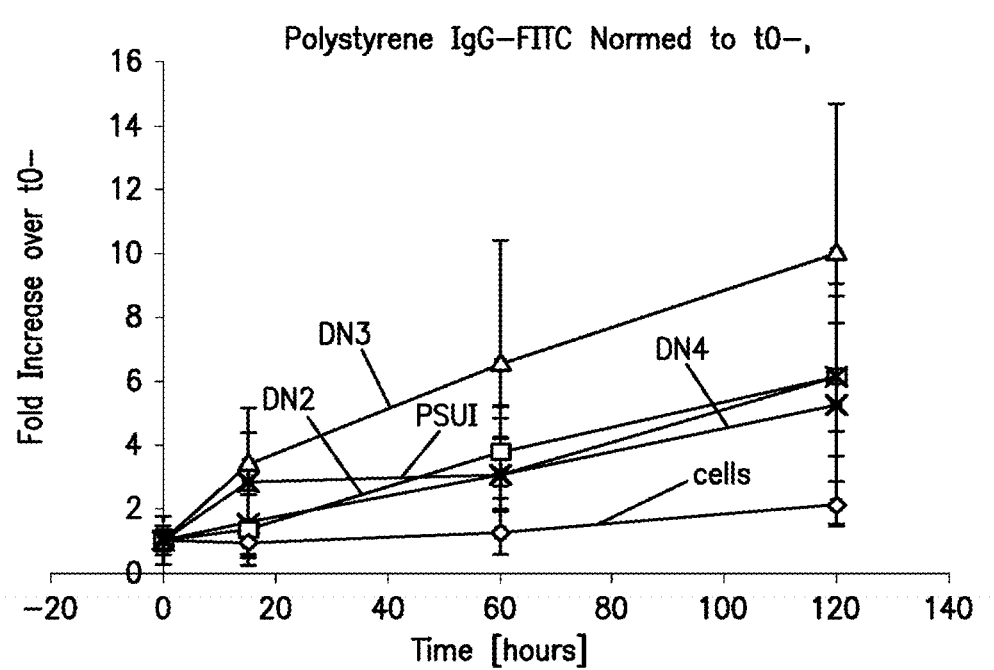

FIG. 36A and FIG. 36B graphically illustrate the effects on permeability to immunoglobulin-G (IgG) in a monolayer of cells on polystyrene films patterned with nanopatterns as described herein. The film patterns included a DN2 pattern (sample no. 3), a DN3 pattern (sample no. 5), and a DN4 pattern (sample no. 6), as indicated. Also shown are results for a non-patterned film (marked PSUI on FIGS. 36A and 36B) and a layer of cells with no adjacent film (marked 'cells' on FIGS. 36A and 36B). The two figures show the data over two different time scales.

The BSA signal was read on a fluorometer and the IgG signal was read on a spectrophotometer.

Figure 37A:
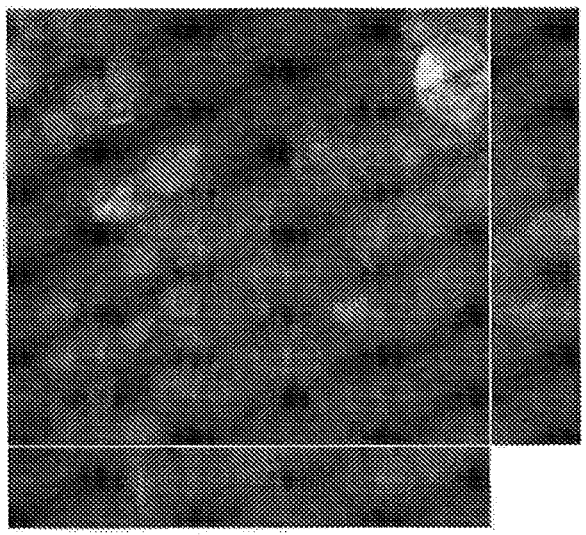
FIGS. 37A and 37B are 3D live/dead flourescein staining images showing paracellular and transcellular transport of IgG across a monolayer of cells on a polystyrene patterned surface as described herein.
Figure 37B:
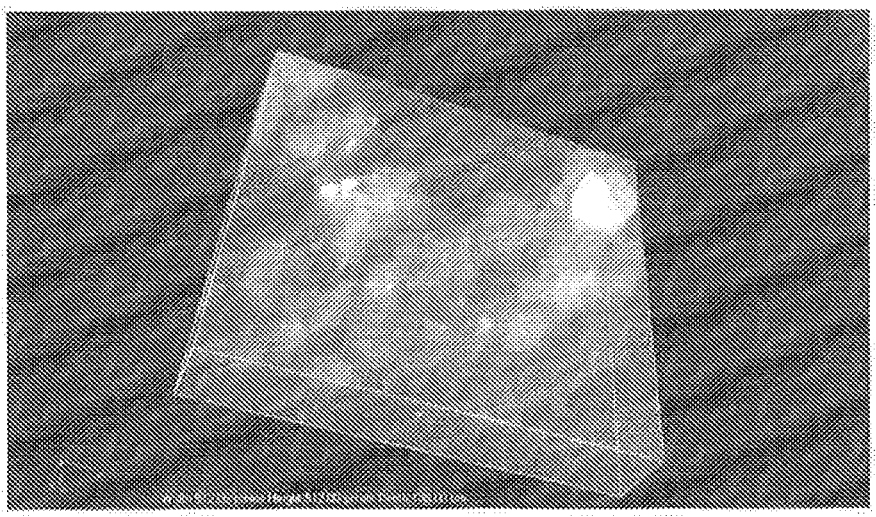

FIGS. 37A and 37B are 3D live/dead flourescein staining images showing paracellular and transcellular transport of IgG across a monolayer of cells on a polystyrene DN4 patterned surface (sample no. 6).

Figure 38:
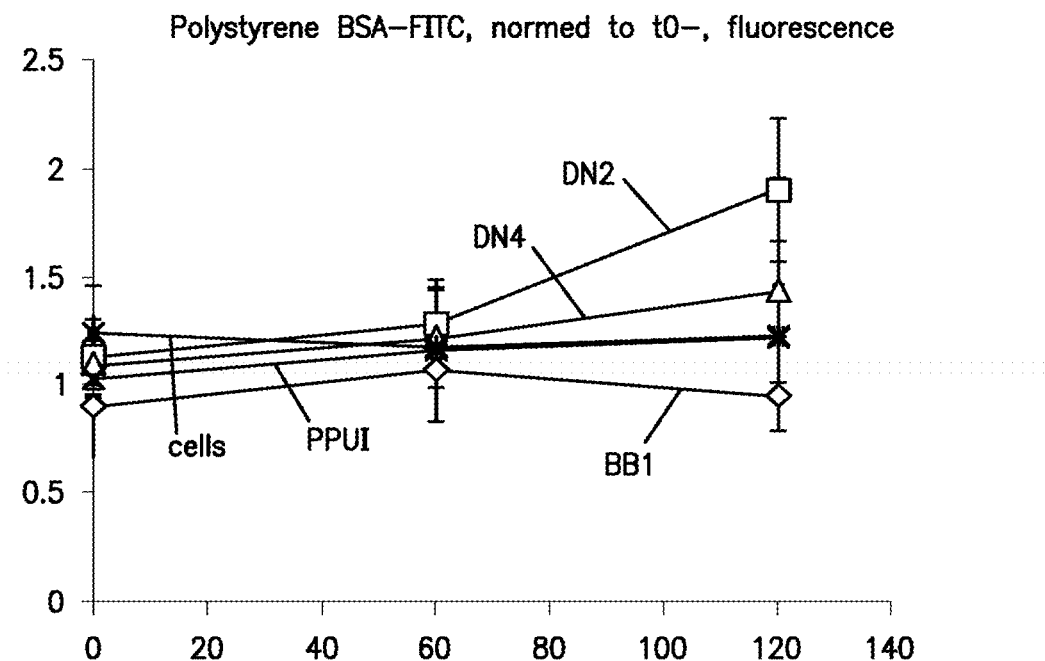
FIG. 38 graphically illustrates the effects on permeability to BSA in a monolayer of cells on polypropylene films patterned with nanopatterns as described herein.

FIG. 38 graphically illustrates the effects on permeability to BSA in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PPUI on FIG. 38) and a layer of cells with no adjacent film (marked 'cells' on FIG. 38).

Figure 39:
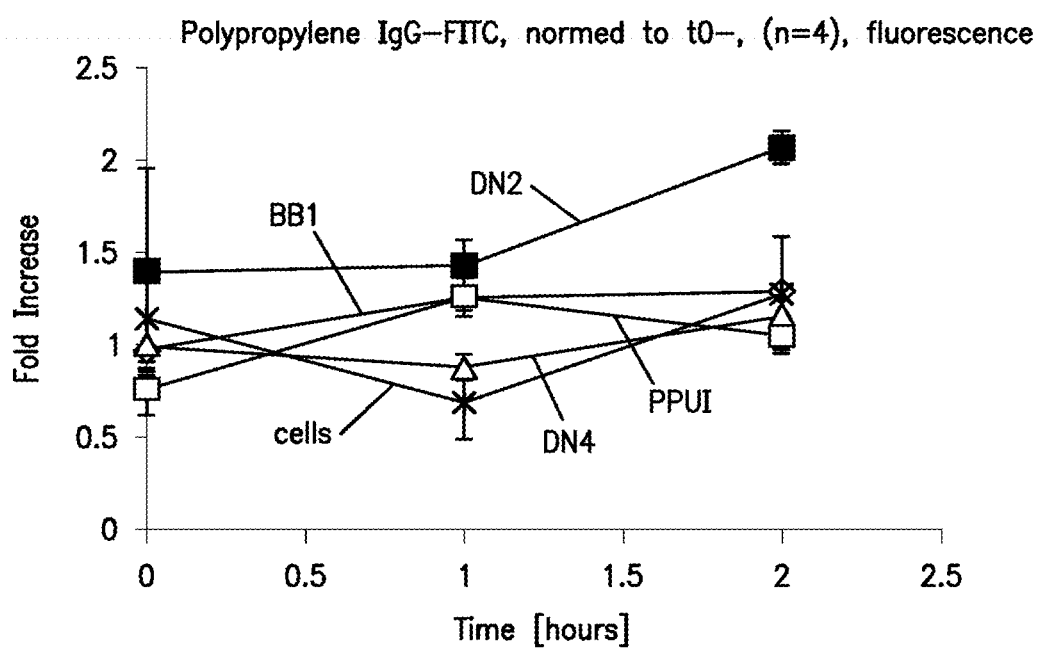
FIG. 39 graphically illustrates the effects on permeability to IgG in a monolayer of cells on polypropylene films patterned with nanopatterns as described herein.

FIG. 39 graphically illustrates the effects on permeability to IgG in a monolayer of cells on polypropylene films patterned with nanopatterns as described herein. Patterns included BB1 (sample no. 8), DN2 (sample no. 4), and DN4 (sample no. 7), as indicated. Also shown are results for a non-patterned film (marked PSUI on FIG. 39) and a layer of cells with no adjacent film (marked 'cells' on FIG. 39).

Figure 40A:
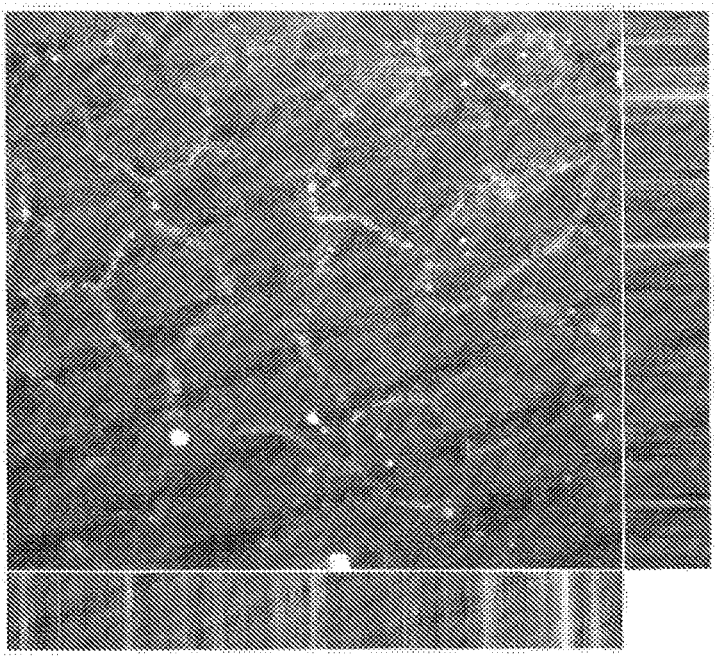
FIGS. 40A and 40B are 3D live/dead flourescein staining images showing paracellular transport of IgG across a monolayer of cells on a polypropylene patterned surface as described herein.
Figure 40B:
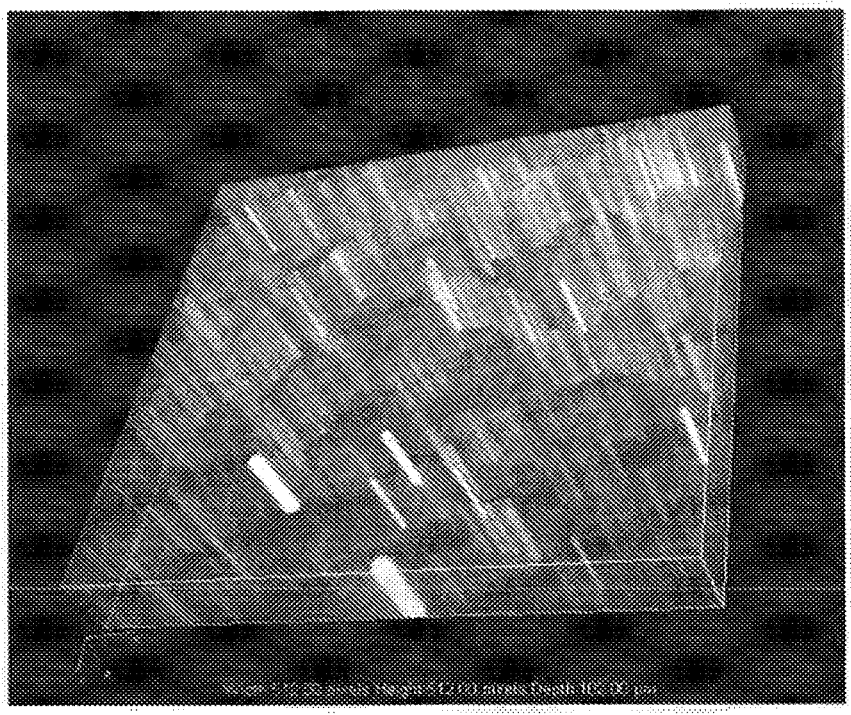

FIGS. 40A and 40B are 3D live/dead flourescein staining images showing paracellular transport of IgG across a monolayer of cells on a polypropylene DN2 patterned surface (sample no. 4).

FIGS. 41A-41F are scanning electron microscopy (SEM) images of Caco-2 cells cultured on nanopatterned surfaces. Specifically, FIGS. 41A and 29B illustrate Caco-2 cells on a flat polystyrene control film. FIGS. 41C and 41D illustrate Caco-2 cells on a polystyrene film patterned with a DN2 pattern (sample no. 3) as described above, and FIGS. 41E and 41F illustrate Caco-2 cells on a polystyrene film patterned with a DN3 pattern (sample no. 5) as described above.

Example 7

Figure 43:
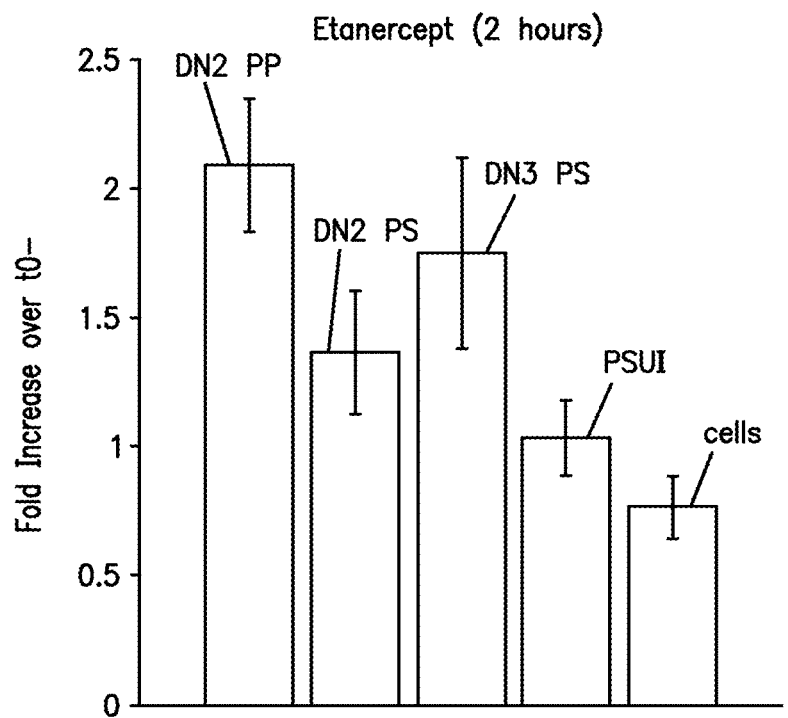
FIG. 43 illustrates the increase in permeability to etanercept of a cellular layer following two hours of contact with a polypropylene or polystyrene films patterns with nanopatterns as described herein.

A method as described in Example 6 was utilized to examine the permeability of a monolayer of Caco-2 cells to the fusion protein therapeutic etanercept (marketed under the trade name as Enbrel®). FIG. 42 graphically illustrates the results for cell layers grown on several different patterned substrates including both polypropylene (DN2 PP—Sample 4 of Table 3) and polystyrene (DN2 PS—Sample 3 of Table 3 and DN3 PS—Sample 1 of Table 3) as well as an unimprinted polystyrene membrane (PSUI) and a layer of cells with no membrane (cells). Results are shown as a fold change from initial permeability with time. FIG. 43 illustrates the fold increase in permeability from initial t=0 at two hours (t=2) following addition of the membrane to the well for the substrates and cellular layer of FIG. 42.

Example 8

An array of microneedles including a nanopatterned surface was formed. Initially, an array of microneedles as illustrated in FIG. 2 was formed on a silicon wafer via a photolithography process. Each needle included two oppositely placed side channels, aligned with one through-die hole in the base of the needle (not visible on FIG. 2).

Microneedles were formed according to a typical micromachining process on a silicon based wafer. The wafers were layered with resist and/or oxide layers followed by selective etching (oxide etching, DRIE etching, iso etching), resist stripping, oxide stripping, and lithography techniques (e.g., iso lithography, hole lithography, slit lithography) according to standard methods to form the array of microneedles.

Following formation of the microneedle array, a 5 µm polypropylene film including a DN2 pattern formed thereon as described above in Example 1 the characteristics of which are described at sample 2 in Table 3 was laid over the microneedle array. The wafer/film structure was held on a heated vacuum box (3 in. $H_2O$ vacuum) at elevated temperature (130° C.) for a period of one hour to gently pull the film over the surface of the microneedles while maintaining the nanopatterned surface of the film.

Figure 44:
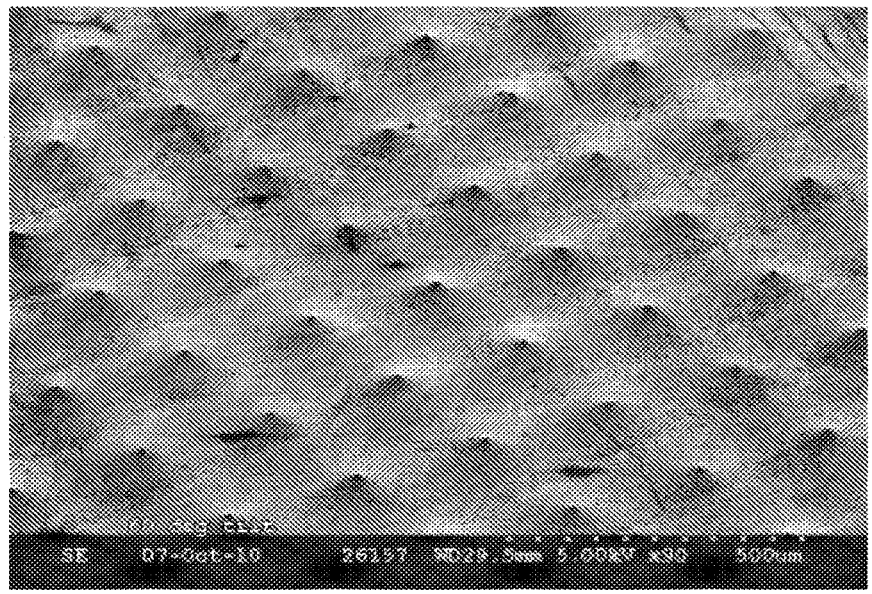
FIG. 44 is an array of microneedles including a surface layer defining a pattern of nanostructures thereon.
Figure 45:
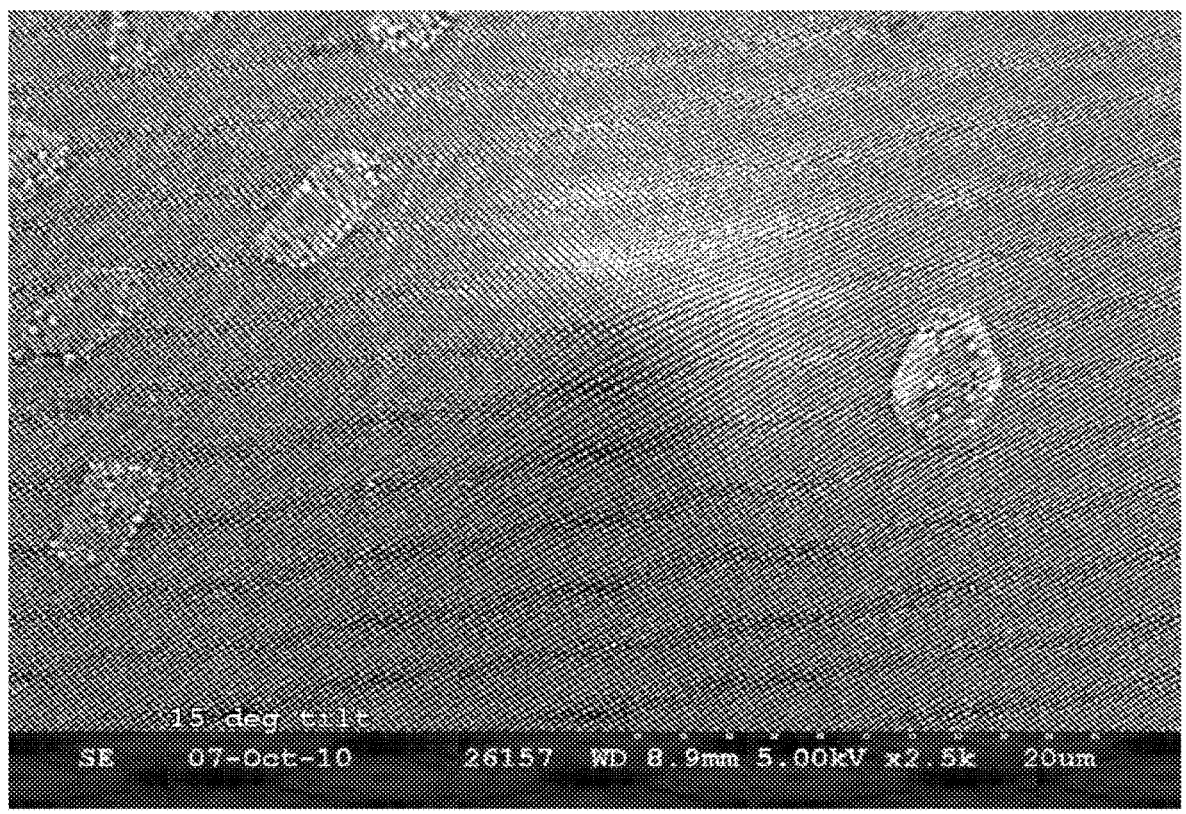
FIG. 45 is a single microneedle of the array of FIG. 44.

FIG. 44 illustrates the film over the top of the array of microneedles, and FIG. 45 is a closer view of a single needle of the array including the nanopatterned film overlaying the top of the needle.

Example 9

Transdermal patches including microneedle arrays formed as described in Example 8 were formed. Patches were formed with either a DN2 pattern or a DN3 pattern on the microneedle array. The films defining the patterns that were applied to the microneedles are described in Table 7, below. Film 1 is equivalent to sample no. 2 of Table 3 and Film 2 is equivalent to sample no. 9 of Table 3.

TABLE 7

| Property | Film 1 | Film 2 |
| --- | --- | --- |
| Pattern | DN2 | DN3 |
| Material | polypropylene | polypropylene |
| Film Thickness | 5 micrometers | 5 micrometers |
| Height of structures | 100 nm | 165 nm, 80 nm, 34 nm |
| Aspect ratio of structures | 0.5 | 0.18 |
| Average Surface Roughness $R_A$ | 16 nm | 50 nm |
| Fractal Dimension | 2.15 | 2.13 |

Control patches were also formed that had no pattern formed on the film subsequently applied to the array of microneedles. Transdermal and subcutaneous formulations of etanercept (Enbrel®) were prepared according to instructions from the drug supplier. The subcutaneous dose formulation (for the positive control) was prepared to facilitate a 4 mg/kg subcutaneous drug dose. The concentration of Enbrel® for transdermal delivery was adjusted such that an intended dosing of 200 mg/kg was achieved in a 24 hr period.

A total of 10 BALB/C mice (assigned designations #1-#10) were used in the study, 8 were transdermally dosed with Enbrel® (group 1) and 2 were subcutaneously dosed with Enbrel® (group 2) as described in Table 8, below. The transdermal patches were applied to shaved skin areas and holes formed near the microneedle tips upon application of the patch to the skin.

TABLE 8

| Group No. | Test Article | Drug | Dose Route | Dose Level | Dose volume | Blood Collection Time Points | Animal Number |
| --- | --- | --- | --- | --- | --- | --- | --- |
| 1 | Transdermal patch | Enbrel ® | Transdermal | 5 mg/ subject | 0.2 ml | Pre-patch | #1, #5 |
|  |  |  |  |  |  | 0.5 h | #2, #6 |
|  |  |  |  |  |  | 2 h | #3, #7 |
|  |  |  |  |  |  | 6 h | #4, #8 |
|  |  |  |  |  |  | 24 h | #2, #6 |
|  |  |  |  |  |  | 72 h | #3, #7 |
| 2 | subcutaneous delivery | Enbrel ® | Subcutaneous | 4 mg/kg | 0.1 ml | 24 h | #9, #10 |

Transdermal patches used included both those defining a nanotopography on the surface (DN2 and DN3 patterns, as described above), as well as patches with no pattern of nanotopography.

Samples of whole blood were collected at the time points indicated in Table 8. Approximately 100 to 2000 blood was taken via-mandibular bleeding and then centrifuged at approximately 1300 rpm for 10 minutes in a refrigerated centrifuge (set at 4° C.). The resulting serum was aspirated and transferred within 30 minutes of blood collection/centrifugation to appropriately labeled tubes. The tubes were frozen and stored in the dark at −70° C. until they were analyzed for levels of Enbrel® using Human sTNF-receptor ELISA kit (R&D Systems cat#DRT200). The space time between two blood samplings on the same subject was 24 hours, to prevent unnecessary stress placed on the subject.

Figure 46:
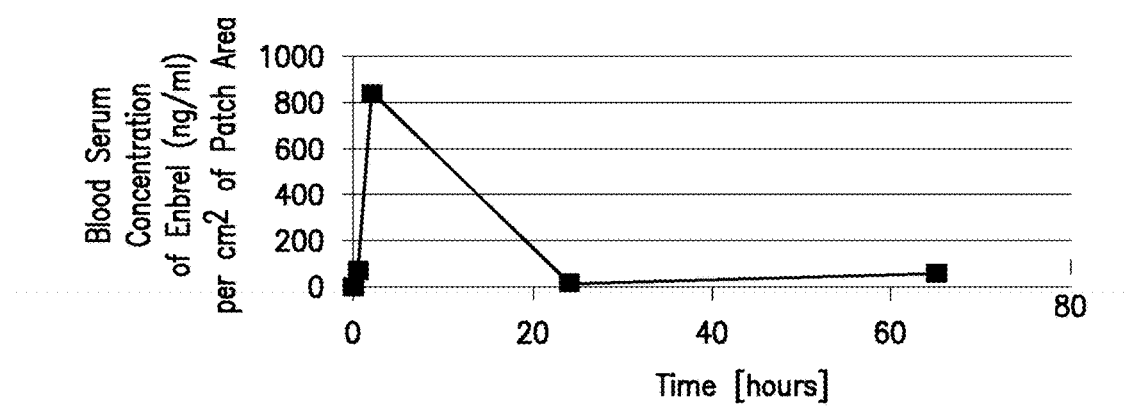
FIG. 46 graphically illustrates the PK profile of a protein therapeutic delivered with a device as described herein.

FIG. 46 graphically illustrates the average PK profile of the transdermal patches that defined a nanotopography thereon. An average of the results for all nanotopography-including patches were used to represent the overall effect of incorporating a nanotopography in conjunction with a microneedle transdermal patch. As may be seen, the blood serum level rose rapidly to over 800 ng/mL/cm$^2$ of patch area within the first two hours of attachment. Following, the blood serum level gradually declined to negligible within 24 hours of attachment. The data used to develop FIG. 46 is provided below in Table 9.

TABLE 9

| Time (hr) | Blood serum concentration (ng/ml) |
| --- | --- |
| 0 | 0 |
| 0.5 | 192.1 |
| 2 | 249.25 |
| 6 | 24.4 |
| 24 | 7.2 |
| 65 | 4.0875 |

Figure 47A:
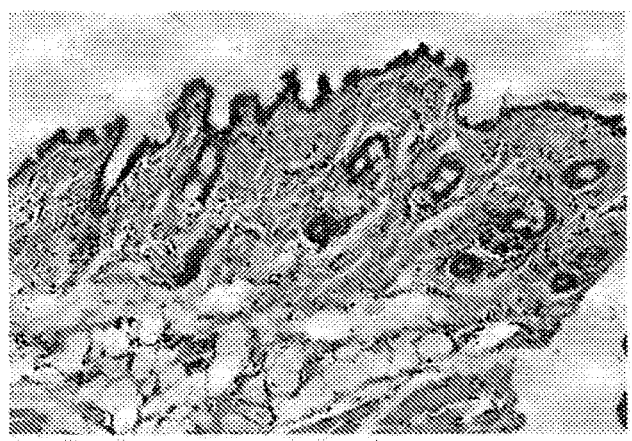
FIGS. 47A and 47B are cross sectional images of skin following transdermal delivery of a protein therapeutic across the skin.
Figure 47B:
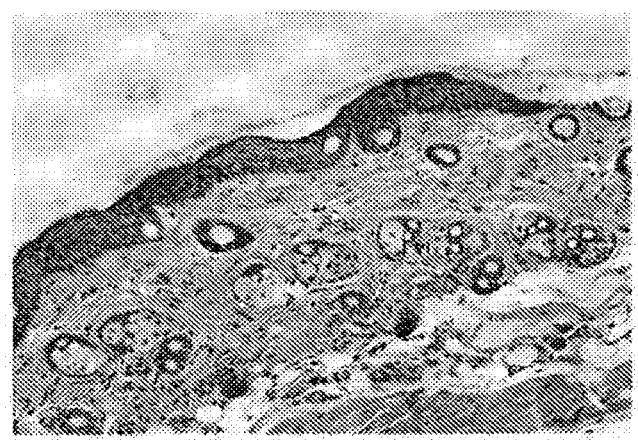

FIGS. 47A and 47B illustrate electron microscopy cross sectional views of the skin that was held in contact with the patches. The images were taken after the patches were removed (72 hours post-attachment). The sample of FIG. 47A was in contact with a patch including a nanotopography on the surface. Specifically, a DN2 pattern, as described above, was formed on the surface of the patch. The sample of FIG. 47B was held in contact with a transdermal patch that did not define a pattern of nanotopography on the surface. As may be seen, the sample of FIG. 47B shows signs of inflammation and a high density of macrophage presence.

Example 10

Transdermal patches including microneedle arrays formed as described in Example 8 were formed. Patches were formed with either a DN2 pattern or a DN3 pattern on the microneedle array as described in Table 7 of Example 9. Control patches were also formed that had no pattern formed on the film subsequently applied to the array of microneedles. Transdermal and subcutaneous formulations of etanercept (Enbrel®) were prepared according to instructions from the drug supplier.

Figure 48:
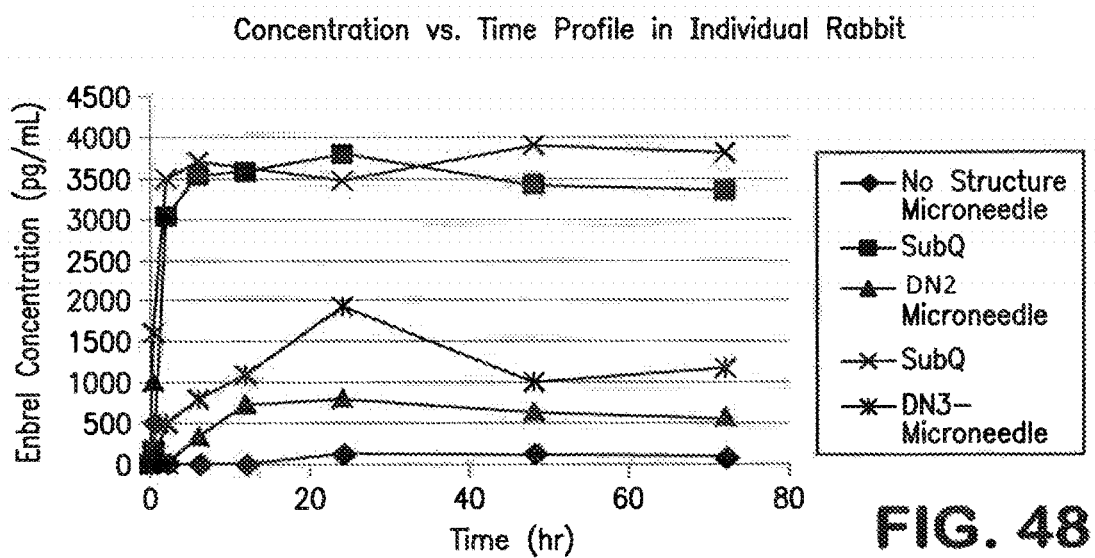
FIG. 48 graphically illustrates the blood serum concentration of a protein therapeutic delivered with a device as described herein.

Test subjects (rabbits) were transdermally dosed with Enbrel® or were subcutaneously (SubQ) dosed with Enbrel®. Results are illustrated graphically in FIG. 48, which provides the blood serum concentration in pg/ml as a function of time. The data used to develop FIG. 48 is provided below in Table 10, below.

TABLE 10

| Time | No structure microneedle | Subcutaneous | DN2 | Subcutaneous | DN3 |
| --- | --- | --- | --- | --- | --- |
| 0 | 0.00 | 0.00 | 0.00 | 0.00 | 0.00 |
| 0.5 | 0.00 | 157.49 | 0.00 | 1611.21 | 0.00 |
| 2 | 0.00 | 3029.07 | 0.00 | 3504.92 | 497.17 |
| 6 | 0.00 | 3545.14 | 338.23 | 3699.24 | 796.64 |
| 12 | 0.00 | 3577.13 | 731.22 | 3571.80 | 1080.60 |
| 24 | 116.78 | 3778.71 | 785.49 | 3464.70 | 1924.24 |
| 48 | 134.23 | 3416.73 | 638.18 | 3885.31 | 1006.95 |
| 72 | 88.68 | 3356.64 | 572.77 | 3803.42 | 1172.67 |

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for increasing permeability of a cellular layer of epithelial cells, the method comprising contacting the cellular layer with a nanostructured surface comprising a microneedle assembly including a plurality of microneedles and a plurality of nanostructures located on each microneedle of the plurality of microneedles, a fractal dimension of the plurality of nanostructures being greater than 1, wherein at least some of the nanostructures of the plurality of nanostructures have a height from about 10 nanometers to about 1 micrometer, and an aspect ratio from about 0.2 to about 5, and wherein the permeability of the cellular layer by a compound is increased as compared to the permeability of the cellular layer prior to contact with the surface.

2. The method according to claim 1, wherein a transepithelial electrical resistance of the cellular layer is reduced to less than 95% of the transepithelial electrical resistance of the cellular layer prior to contact with the surface.

3. The method according to claim 1, wherein at least a portion of the nanostructures have a cross-sectional dimension of less than 500 nanometers and greater than 5 nanometers.

4. The method according to claim 1, wherein the nanostructured surface further comprises microstructures, the plurality of nanostructures including first nanostructures having a cross-sectional dimension smaller than the microstructures.

5. The method according to claim 4, further comprising second nanostructures having a cross-sectional dimension less than the cross-sectional dimension of the microstructures and greater than the cross-sectional dimension of the first nanostructures.

6. The method according to claim 1, further comprising a film overlaying at least one microneedle of the microneedle assembly, the film having a first surface and a second surface, wherein the first surface of the film is adhered to the microneedle and at least partially conforms thereto, and wherein the second surface comprises the plurality of nanostructures, wherein the microneedle assembly and the film define a composite microneedle array.

7. The method according to claim 1, wherein at least one of the microneedles contains a channel along a length of the microneedle, and wherein the compound is configured to flow through the channel.

8. A method for increasing permeability of a cellular layer of epithelial cells, the method comprising:
contacting the cellular layer with a nanostructured surface comprising a microneedle assembly including a plurality of microneedles and a plurality of nanostructures located on each microneedle of the plurality of microneedles, a fractal dimension of the plurality of nanostructures being greater than 1, wherein at least some of the nanostructures of the plurality of nanostructures have a height from about 10 nanometers to about 1 micrometer, and an aspect ratio from about 0.2 to about 5, and, wherein
the permeability of the cellular layer to a compound having a molecular weight of greater than 400 Da is increased at least one-fold as compared to the permeability of the cellular layer prior to contact with the surface.

9. The method according to claim 8, wherein the fractal dimension of the plurality of nanostructures is about 2.5.

10. The method according to claim 8, wherein, subsequent to contact between the cellular layer of epithelial cells and the nanostructured surface, a transepithelial electrical resistance of the cellular layer is less than 85% of the transepithelial electrical resistance of the cellular layer prior to contact with the surface.

11. The method according to claim 8, wherein the interaction of the cellular layer and the nanostructured surface results in at least one of up-regulation of one or more anti-inflammatory cytokines and down-regulation of one or more pro-inflammatory cytokines.

12. The method according to claim 8, wherein the compound is a selected from a protein therapeutic and a polynucleotide.

13. The method according to claim 8, wherein the method for increasing the permeability of a layer of epithelial cells changes intercellular junction.

14. The method according to claim 13, wherein the intercellular junction is a tight junction.

* * * * *